(12) United States Patent
Louis et al.

(10) Patent No.: US 11,535,830 B2
(45) Date of Patent: Dec. 27, 2022

(54) THREONINE-PRODUCING YEAST

(71) Applicant: ADISSEO FRANCE S.A.S., Antony (FR)

(72) Inventors: Dominique Louis, Forges les Bains (FR); Karine Jaillardon, Saint Michel sur Orge (FR); Dominique Thomas, Gif sur Yvette (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

(21) Appl. No.: 16/630,586

(22) PCT Filed: Jul. 10, 2018

(86) PCT No.: PCT/EP2018/068718
§ 371 (c)(1),
(2) Date: Jan. 13, 2020

(87) PCT Pub. No.: WO2019/011946
PCT Pub. Date: Jan. 17, 2019

(65) Prior Publication Data
US 2021/0087594 A1 Mar. 25, 2021

(30) Foreign Application Priority Data
Jul. 11, 2017 (EP) ..................... 17305909

(51) Int. Cl.
| C12N 9/06 | (2006.01) |
| C12N 9/02 | (2006.01) |
| C12N 9/10 | (2006.01) |
| C12N 9/12 | (2006.01) |
| C12N 9/88 | (2006.01) |
| C12P 13/08 | (2006.01) |
| C12N 1/20 | (2006.01) |
| C12N 15/52 | (2006.01) |
| C12N 15/81 | (2006.01) |

(52) U.S. Cl.
CPC ......... *C12N 9/0008* (2013.01); *C12N 9/0014* (2013.01); *C12N 9/1025* (2013.01); *C12N 9/1096* (2013.01); *C12N 9/1217* (2013.01); *C12N 9/88* (2013.01); *C12N 15/52* (2013.01); *C12N 15/81* (2013.01); *C12P 13/08* (2013.01)

(58) Field of Classification Search
CPC ...... C12N 9/1025; C12N 9/0008; C12N 9/88; C12N 9/1217; C12N 9/0016; C12N 9/1096; C12P 13/08
See application file for complete search history.

(56) References Cited

U.S. PATENT DOCUMENTS

| 3,375,173 A | 3/1968 | Nishimura et al. |
| 4,996,147 A | 2/1991 | Furukawa et al. |
| 8,852,898 B2 | 10/2014 | Lee et al. |
| 10,889,842 B2 * | 1/2021 | Saville ..................... C12N 1/30 |
| 2005/0124048 A1 | 6/2005 | Akhverdian et al. |
| 2008/0286841 A1 | 11/2008 | Kroger et al. |
| 2009/0093030 A1 | 4/2009 | Park et al. |
| 2015/0197779 A1 | 7/2015 | Saville et al. |

FOREIGN PATENT DOCUMENTS

| WO | 2004/076659 A2 | 9/2004 |
| WO | 2005/014840 A1 | 2/2005 |
| WO | 2007/136133 A1 | 11/2007 |
| WO | 2008/013428 A1 | 1/2008 |
| WO | 2015/103497 A1 | 7/2015 |

OTHER PUBLICATIONS

Farfan. Enrichment of threonine content in *Saccharomyces cerevisiae* by pathway engineering. Enzyme and Microbial Technology 26 (2000) 763-770.*
Li. Current status on metabolic engineering for the production of L-aspartate family amino acids and derivatives. Bioresource Technology 245 (2017) 1588-1602. Published online on May 24, 2017.*
Peng. Coupling gene regulatory patterns to bioprocess conditions to optimize synthetic metabolic modules for improved sesquiterpene production in yeast. Biotechnol Biofuels (2017) 10:43. DOI 10.1186/s13068-017-0728-x. Published on Feb. 21, 2017.*
Xu. Mutagenesis of Key Residues in the Binding Center of l-Aspartate-β-Semialdehyde Dehydrogenase from *Escherichia coli* Enhances Utilization of the Cofactor NAD(H).Chembiochem. Jan. 1, 2016;17(1):56-64. Epub Dec. 10, 2015.*
Dong et al.; Metabolic engineering of *Escherichia coli* and Corynebacterium glutamicum for the production of L-threonine; Biotechnology Advances; 2011; pp. 11-23; vol. 29, No. 1.
Lee et al.; "Systems metabolic engineering of *Escherichia coli* for L-threonine production;" Molecular Systems Biology; 2007; pp. 1-8; vol. 3, No. 149.
Rees et al.; "The biosynthesis of threonine by mammalian cells: expression of a complete bacterial biosynthetic pathway in an animal cell;" Biochem. J.; 1995; pp. 999-1007; vol. 309, No. 3.
Gomes et al; "Production of L-methionine by submerged fermentation: A review;" Enzyme and Microbial Technology; 2005; pp. 3-18; vol. 37, No. 1.
Van Der Werf et al; "Environmental and physiological factors affecting the succinate product ratio during carbohydrate fermentation by *Actinobacillus* sp. 130Z;" Arch Microbiol; 1997; pp. 332-342; vol. 167.
Palmieri et al: "Threonine diffusion and threonine transport in Corynebacterium glutamicum and their role in threonine production;" Arch Microbiol; 1996; pp. 48-54; vol. 165.
Ravid et al.; "Degradation signal diversity in the ubiquitin-proteasome system;" Nat Rev Mol Cell Biol.; 2008; pp. 679-690; vol. 9, No. 9.

(Continued)

*Primary Examiner* — Yong D Pak
(74) *Attorney, Agent, or Firm* — Oliff PLC

(57) ABSTRACT

A method for the bio-production of threonine including genetically modified yeasts and a method in which they are used to produce threonine, as compared to the parent yeasts.

22 Claims, No Drawings
Specification includes a Sequence Listing.

(56) References Cited

OTHER PUBLICATIONS

Sagers et al.; "Acetate Formation in Clostridium Acidi-Urici Acetokinase;" J. Bacteriol; 1961; pp. 233-238; vol. 82.
Velculescu et al.; "Characterization of the Yeast Transcriptome;" Cell; 1997; pp. 243-251; vol. 88.
Wang et al; "Consequences of a Modified Putative Substrate-Activation Site on Catalysis by Yeast Pyruvate Decarboxylase;" Biochemistry; 2001; pp. 1755-1763; vol. 40.
Yagi et al.; "Aspartate: 2-Oxoglutarate Aminotransferase from Bakers' Yeast: Crystallization and Characterization;" J. Biochem. 1982; pp. 35-43; vol. 92.
Yamanishi et al; "A Genome-Wide Activity Assessment of Terminator Regions in Saccharomyces cerevisiae Provides a "Terminatome" Toolbox;" ACS Synthetic Biology; 2013; pp. 337-347; vol. 2, No. 6.
Yu et al.; "Pac-Man for biotechnology: co-opting degrons for targeted protein degradation to control and alter cell function;" Current Opinion in Biotechnology; 2015; pp. 199-204; vol. 36.
Bachmair et al.; "In Vivo Half-Life of a Protein Is a Function of Its Amino-Terminal Residue;" Science; 1986; pp. 179-186; vol. 234.
Bazaes et al.; "Comparative Kinetic Effects of Mn (II), Mg (II) and the ATP/ADP Ratio on Phosphoenolpyruvate Carboxykinases from Anaerobiospirillum succiniciproducens and Saccharomyces cerevisiae;" The Protein Journal; 2007; pp. 265-269; vol. 26, No. 4.
Chassagnole et al.; "Control of the threonine-synthesis pathway in Escherichia coli: a theoretical and experimental approach;" Biochem. J.; 2001; pp. 433-444; vol. 356.
Cho et al.; "A degron created by SMN2 exon 7 skipping is a principal contributor to spinal muscular aliophy severity;" Genes & Development; 2010; pp. 438-442; vol. 24.
Dicarlo et al.; "Genome engineering in Saccharomyces cerevisiae using CRISPR-Cas systems;" Nucleic Acids Research; 2013; pp. 4336-4343; vol. 41, No. 7.
Faehnle et al.; "A New Branch in the Family: Structure of Asparatate-β-semialdehyde Dehydrogenase from Methanococcus jannaschii;" J. Mol. Biol.; 2005; pp. 1055-1068; vol. 353.
Fischer et al.; "Catalytic properties of a bacterial acylating acetaldehyde dehydrogenase: Evidence for several active bligomeric states and coenzyme A activation upon binding;" Chemico-Biological Interactions; 2013; pp. 70-77; vol. 202.
Fortmann et al.; "A regulated, ubiquitin-independent degron in IκBα;" J Mol Biol. 2015; pp. 2748-2756; vol. 427, No. 17.
Ganzhorn et al.; "Kinetic Characterization of Yeast Alcohol Dehydrogenases;" The Journal of Biological Chemistry; 1987; pp. 3754-3761; vol. 262, No. 8.
Gerrard Wheeler et al.; "Identification of domains involved in the allosteric regulation of cytosolic Arabidopsis thaliana NADP-malic enzymes;" FEBS Journal; 2009; pp. 5665-5677; vol. 276.

He et al.; "Crystal structure of Saccharomyces cerevisiae 6-phosphogluconate dehydrogenase Gnd I;" BMC Structural Biology; 2007; pp. 1-9; vol. 7, No. 38.
Hochstrasser; "Ubiquitin-Dependent Protein Degradation;" Annu. Rev. Genet.; 1996; pp. 405-439; vol. 30.
Stadtman et al.; "Feed-back Inhibition and Repression of Aspartokinase Activity in Escherichia coli and Saccharomyces cerevisiae;" The Journal of Biological Chemistry; 1961; pp. 2033-2038; vol. 236, No. 7.
Keren et al.; "Promoters maintain their relative activity levels under different growth conditions;" Molecular Systems Biology; 2013; pp. 1-17; vol. 9, No. 701.
Koller et al.; "The CUP I promoter of Saccharomyces cerevisiae is inducible by copper in Pichia pastoris;" Yeast; 2000; pp. 651-656; vol. 16.
Kuby et al.; "Glucose 6-Phosphate Dehydrogenase (Crystalline) from Brewers' Yeast;" Dehydrogenases and Oxidases; 1966; pp. 116-125.
Ravanel et al.; "Methionine Biosynthesis in Higher Plants. I. Purification and Characterization of Cystathionine γ-Synthase from Spinach Chloroplasts;" Archives of Biochemistry and Biophysics; 1995; pp. 572-584; vol. 316, No. 1.
Susan-Resiga et al.; "Proton Donor in Yeast Pyruvate Kinase: Chemical and Kinetic Properties of the Active Site Thr 298 to Cys Mutant;" Biochemistry; 2004; pp. 15230-15245; vol. 43.
Yamagata; "Partial Purification and Some Properties of Homoserine O-Acetyltransferase of a Methionine Auxotroph of Saccharomyces cerevisiae;" Journal of Bacteriology; 1987; pp. 3458-3463; vol. 169, No. 8.
Noor et al.; "Allosteric NADP-glutamate dehydrogenase from aspergilli: purification, characterization and implications for metabolic regulation at the carbon-nitrogen interface;" Microbiology; 2005; pp. 1409-1419; vol. 151.
Castaño-Cerezo et al.; "An insight into the role of phosphotransacetylase (pta) and the acetate/acetyl-CoA node in Escherichia coli;" Microbial Cell Factories; 2009; pp. 1-19; vol. 8, No. 54.
Schildkraut et al.; "Threonine Synthetase-Catalyzed Conversion of Phosphohomoserine to α-Ketobutyrate in Bacillus subtilis;" Journal of Bacteriology; 1973; pp. 777-785; vol. 115, No. 3.
Mannhaupt et al.; "Yeast homoserine kinase: Characteristics of the corresponding gene, THR1, and the purified enzyme, and evolutionary relationships with other enzymes of threonine metabolism;" Eur. J. Biochem.; 1990; pp. 115-122; vol. 191.
Cahyanto et al.; "Regulation of aspartokinase, aspartate semialdehyde dehydrogenase, dihydrodipicolinate synthase and dihydrodipicolinate reductase in Lactobacillus plantarum;" Microbiology; 2006; pp. 105-112; vol. 152.
Sep. 3, 2018 Search Report issued in International Patent Application No. PCT/EP2018/068718.
Sep. 3, 2018 Written Opinion of the International Searching Authority issued in International Patent Application No. PCT/EP2018/068718.

* cited by examiner

SEQUENCE LISTING

<160> NUMBER OF SEQ ID NOS: 119

<210> SEQ ID NO 1
<211> LENGTH: 1098
<212> TYPE: DNA
<213> ORGANISM: Saccharomyces cerevisiae
<220> FEATURE:
<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 1

```
atggctggaa agaaaattgc tggtgttttg ggtgctactg gttccgttgg tcaacgtttc      60
attctgttgt tggcaaatca ccctcatttc gaactgaaag ttcttggtgc ctcttctaga     120
tcagctggca agaaatacgt tgacgctgtg aactggaagc aaaccgattt gctaccggaa     180
tctgctaccg atattattgt ttccgaatgt aaatctgaat ctttaaaga gtgtgacatc      240
gtcttttccg gattggatgc tgactatgct ggcgctatcg aaaaggaatt catggaagct     300
ggtatcgcca ttgtttccaa tgccaagaat tatagaagag aacaagatgt gccattgatt     360
gttcctgttg tcaatcctga gcatttggat attgtagctc aaaagcttga caccgccaag     420
gctcaaggta agccaagacc agggttcatt atctgtatt ccaattgttc cactgcaggt      480
ttggttgcac cattgaagcc tttgattgaa aaattcggtc ctattgatgc tttgaccact     540
actactttgc aagcaatctc aggtgctggt ttctccccag gtgtaccagg tattgatatt     600
ctagacaata ttattccata cattggtggt gaagaagaca gatggaatg ggagaccaag      660
aaaatcttgg ctccattagc agaagacaag acacacgtca aactattgac tccagaagaa     720
atcaaagtct ctgctcaatg taacagagtc gctgttttccg atgggcacac cgaatgtatc    780
tctttgaggt tcaagaacag acctgctcca tccgtcgagc aagtcaagac atgcctaaaa    840
gaatacgtct gcgatgccta caaattaggc tgtcattctg ctccaaagca aactattcat    900
gttttggaac aaccagacag acctcaacca aggttggaca ggaacagaga cagcggttac    960
ggtgtttccg ttggtagaat cagagaagac ccattgttag atttcaaat ggttgtcctt   1020
tcccacaaca ccattattgg tgccgctggt tctggtgtct tgattgccga atcttacta   1080
gcaagaaact tgatttaa                                                 1098
```

<210> SEQ ID NO 2
<211> LENGTH: 1098
<212> TYPE: DNA
<213> ORGANISM: Saccharomyces cerevisiae
<220> FEATURE:
<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 2

```
atggctggaa agaaaattgc tggtgttttg ggtgctactg gttccgttgg tcaacgtttc      60
attctgttgt tggcaaatca ccctcatttc gaactgaaag ttcttggtgc ctctgagaga     120
tcagctggca agaaatacgt tgacgctgtg aactggaagc aaaccgattt gctaccggaa     180
tctgctaccg atattattgt ttccgaatgt aaatctgaat ctttaaaga gtgtgacatc      240
gtcttttccg gattggatgc tgactatgct ggcgctatcg aaaaggaatt catggaagct     300
ggtatcgcca ttgtttccaa tgccaagaat tatagaagag aacaagatgt gccattgatt     360
gttcctgttg tcaatcctga gcatttggat attgtagctc aaaagcttga caccgccaag     420
gctcaaggta agccaagacc agggttcatt atctgtatt ccaattgttc cactgcaggt      480
```

-continued

```
ttggttgcac cattgaagcc tttgattgaa aaattcggtc ctattgatgc tttgaccact      540
actactttgc aagcaatctc aggtgctggt ttctccccag gtgtaccagg tattgatatc      600
ctagacaata ttattccata cattggtggt gaagaagaca agatggaatg ggagaccaag      660
aaaatcttgg ctccattagc agaagacaag acacacgtca aactattgac tccagaagaa      720
atcaaagtct ctgctcaatg taacagagtc gctgtttccg atgggcacac cgaatgtatc      780
tctttgaggt tcaagaacag acctgctcca tccgtcgagc aagtcaagac atgcctaaaa      840
gaatacgtct gcgatgccta caaattaggc tgtcattctg ctccaaagca aactattcat      900
gttttggaac aaccagacag acctcaacca aggttggaca ggaacagaga cagcggttac      960
ggtgtttccg ttggtagaat cagagaagac ccattgttag atttcaaaat ggttgtcctt     1020
tcccacaaca ccattattgg tgccgctggt tctggtgtct tgattgccga atcttacta      1080 gcaagaaact tgatttaa                                                   1098
```

<210> SEQ ID NO 3
<211> LENGTH: 365
<212> TYPE: PRT
<213> ORGANISM: Saccharomyces cerevisiae
<220> FEATURE:
<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 3

```
Met Ala Gly Lys Lys Ile Ala Gly Val Leu Ala Thr Gly Ser Val
1               5                   10                  15

Gly Gln Arg Phe Ile Leu Leu Ala Asn His Pro His Phe Glu Leu
                20                  25                  30

Lys Val Leu Gly Ala Ser Ser Arg Ser Ala Gly Lys Lys Tyr Val Asp
            35                  40                  45

Ala Val Asn Trp Lys Gln Thr Asp Leu Leu Pro Glu Ser Ala Thr Asp
50                  55                  60

Ile Ile Val Ser Glu Cys Lys Ser Glu Phe Phe Lys Glu Cys Asp Ile
65                  70                  75                  80

Val Phe Ser Gly Leu Asp Ala Asp Tyr Ala Gly Ala Ile Glu Lys Glu
                85                  90                  95

Phe Met Glu Ala Gly Ile Ala Ile Val Ser Asn Ala Lys Asn Tyr Arg
            100                 105                 110

Arg Glu Gln Asp Val Pro Leu Ile Val Pro Val Val Asn Pro Glu His
        115                 120                 125

Leu Asp Ile Val Ala Gln Lys Leu Asp Thr Ala Lys Ala Gln Gly Lys
130                 135                 140

Pro Arg Pro Gly Phe Ile Ile Cys Ile Ser Asn Cys Ser Thr Ala Gly
145                 150                 155                 160

Leu Val Ala Pro Leu Lys Pro Leu Ile Glu Lys Phe Gly Pro Ile Asp
                165                 170                 175

Ala Leu Thr Thr Thr Thr Leu Gln Ala Ile Ser Gly Ala Gly Phe Ser
            180                 185                 190

Pro Gly Val Pro Gly Ile Asp Ile Leu Asp Asn Ile Pro Tyr Ile
        195                 200                 205

Gly Gly Glu Glu Asp Lys Met Glu Trp Glu Thr Lys Lys Ile Leu Ala
    210                 215                 220

Pro Leu Ala Glu Asp Lys Thr His Val Lys Leu Leu Thr Pro Glu Glu
225                 230                 235                 240
```

Ile Lys Val Ser Ala Gln Cys Asn Arg Val Ala Val Ser Asp Gly His
              245                 250                 255

Thr Glu Cys Ile Ser Leu Arg Phe Lys Asn Arg Pro Ala Pro Ser Val
          260                 265                 270

Glu Gln Val Lys Thr Cys Leu Lys Glu Tyr Val Cys Asp Ala Tyr Lys
      275                 280                 285

Leu Gly Cys His Ser Ala Pro Lys Gln Thr Ile His Val Leu Glu Gln
  290                 295                 300

Pro Asp Arg Pro Gln Pro Arg Leu Asp Arg Asn Arg Asp Ser Gly Tyr
305                 310                 315                 320

Gly Val Ser Val Gly Arg Ile Arg Glu Asp Pro Leu Leu Asp Phe Lys
              325                 330                 335

Met Val Val Leu Ser His Asn Thr Ile Ile Gly Ala Ala Gly Ser Gly
              340                 345                 350

Val Leu Ile Ala Glu Ile Leu Leu Ala Arg Asn Leu Ile
              355                 360                 365

<210> SEQ ID NO 4
<211> LENGTH: 1074
<212> TYPE: DNA
<213> ORGANISM: Saccharomyces cerevisiae
<220> FEATURE:
<223> OTHER INFORMATION: HOMOSERINE KINASE (THR1)
<220> FEATURE:
<223> OTHER INFORMATION: HOMOSERINE KINASE (THR1)

<400> SEQUENCE: 4
atggttcgtg ccttcaaaat taaagttcca gcttcttccg ccaatatcgg ccctggttat      60
gatgttcttg gtgtcggtct ttctctattc ttggagttag atgtcaccat cgactccagc     120
caagctcagg aaacaaacga cgatcccaac aactgcaagc tgtcttacac taagaaagt     180 gaaggctatt ctacggtccc attgcgttct gatgctaacc tgattaccag gactgcgtta     240
tatgtgttgc gttgcaacaa tattagaaac ttcccctccg gaaccaaagt tcacgtctcc     300
aacccaatcc cacttggccg tggattgggt tcctctggtg cagcagttgt ggcaggtgtt     360
attttaggta acgaagtggc ccaattgggt ttctctaagc aacgtatgtt ggactactgt     420
ttgatgattg aacgtcatcc agacaacata accgctgcta tgatgggagg cttttgcggt     480
tcattcctaa gggacttgac cccacaagag gtggaaagac gtgagattcc attggctgag     540
gtgcttccag aaccttctgg tggtgaagat accggtctgg ttccccccatt acctcccacc     600 gatatcggta gacatgtcaa ataccaatgg aaccccgcca ttaaatgtat tgcgatcatc     660
ccacagttcg agttgtccac cgccgactcc agaggcgttc ttccaaaagc ctacccaacc     720
caggacttgg ttttcaatct acaaagattg gccgtcttga ccacagcttt gaccatggac     780
ccacctaatg ccgacttaat ctaccctgct atgcaagatc gtgtccacca accttataga     840
aagacattga tcccaggtct cacggaaatc ttatcatgtg tcaccccatc cacatacccct     900 ggcctattgg gtatctgctt gtcaggtgca ggcccaacta tcttggcttt ggccactgag     960
aatttcgaag aaatctctca agaaattatc aacaggttcg ccaaaaacgg catcaagtgc    1020
tcctggaaac tactgagcc tgcctacgat ggtgctagcg tcgaacagca atga           1074

<210> SEQ ID NO 5
<211> LENGTH: 357
<212> TYPE: PRT
<213> ORGANISM: Saccharomyces cerevisiae
<220> FEATURE:

<223> OTHER INFORMATION: HOMOSERINE KINASE (THR1)
<220> FEATURE:
<223> OTHER INFORMATION: HOMOSERINE KINASE (THR1)

<400> SEQUENCE: 5

```
Met Val Arg Ala Phe Lys Ile Lys Val Pro Ala Ser Ser Ala Asn Ile
1               5                   10                  15

Gly Pro Gly Tyr Asp Val Leu Gly Val Gly Leu Ser Leu Phe Leu Glu
            20                  25                  30

Leu Asp Val Thr Ile Asp Ser Ser Gln Ala Gln Glu Thr Asn Asp Asp
        35                  40                  45

Pro Asn Asn Cys Lys Leu Ser Tyr Thr Lys Glu Ser Glu Gly Tyr Ser
    50                  55                  60

Thr Val Pro Leu Arg Ser Asp Ala Asn Leu Ile Thr Arg Thr Ala Leu
65                  70                  75                  80

Tyr Val Leu Arg Cys Asn Asn Ile Arg Asn Phe Pro Ser Gly Thr Lys
                85                  90                  95

Val His Val Ser Asn Pro Ile Pro Leu Gly Arg Gly Leu Gly Ser Ser
            100                 105                 110

Gly Ala Ala Val Val Ala Gly Val Ile Leu Gly Asn Glu Val Ala Gln
        115                 120                 125

Leu Gly Phe Ser Lys Gln Arg Met Leu Asp Tyr Cys Leu Met Ile Glu
    130                 135                 140

Arg His Pro Asp Asn Ile Thr Ala Ala Met Met Gly Gly Phe Cys Gly
145                 150                 155                 160

Ser Phe Leu Arg Asp Leu Thr Pro Gln Glu Val Glu Arg Arg Glu Ile
                165                 170                 175

Pro Leu Ala Glu Val Leu Pro Glu Pro Ser Gly Gly Glu Asp Thr Gly
            180                 185                 190

Leu Val Pro Pro Leu Pro Pro Thr Asp Ile Gly Arg His Val Lys Tyr
        195                 200                 205

Gln Trp Asn Pro Ala Ile Lys Cys Ile Ala Ile Ile Pro Gln Phe Glu
    210                 215                 220

Leu Ser Thr Ala Asp Ser Arg Gly Val Leu Pro Lys Ala Tyr Pro Thr
225                 230                 235                 240

Gln Asp Leu Val Phe Asn Leu Gln Arg Leu Ala Val Leu Thr Thr Ala
                245                 250                 255

Leu Thr Met Asp Pro Pro Asn Ala Asp Leu Ile Tyr Pro Ala Met Gln
            260                 265                 270

Asp Arg Val His Gln Pro Tyr Arg Lys Thr Leu Ile Pro Gly Leu Thr
        275                 280                 285

Glu Ile Leu Ser Cys Val Thr Pro Ser Thr Tyr Pro Gly Leu Leu Gly
    290                 295                 300

Ile Cys Leu Ser Gly Ala Gly Pro Thr Ile Leu Ala Leu Ala Thr Glu
305                 310                 315                 320

Asn Phe Glu Glu Ile Ser Gln Glu Ile Ile Asn Arg Phe Ala Lys Asn
                325                 330                 335

Gly Ile Lys Cys Ser Trp Lys Leu Leu Glu Pro Ala Tyr Asp Gly Ala
            340                 345                 350

Ser Val Glu Gln Gln
        355
```

<210> SEQ ID NO 6
<211> LENGTH: 1545
<212> TYPE: DNA

<213> ORGANISM: Saccharomyces cerevisiae
<220> FEATURE:
<223> OTHER INFORMATION: HOMOSERINE KINASE (THR4)
<220> FEATURE:
<223> OTHER INFORMATION: HOMOSERINE KINASE (THR4)

<400> SEQUENCE: 6

```
atgcctaacg cttcccaagt ttacagatct accagatcca gctctccaaa gacaatctct      60
tttgaagagg ctatcattca aggtctggcc actgacggtg gtcttttcat tccaccaact     120
attccacaag tggaccaagc cactctttc aatgattggt caaagctctc cttccaagac     180
ttagcctttg ctatcatgag actatacatt gcccaagaag agattccaga tgctgatcta     240
aaggacttga tcaagagatc ttattctact ttccgttctg atgaagtcac ccccttggtg     300
caaaacgtca ctggtgacaa ggagaatttg cacattttag aattattcca cggtcctacc     360
tacgctttca agacgttgc tttacaattt gtcggtaatc ttttgaata cttcttacaa      420
agaaccaacg ccaatttacc tgaaggcgag aaaaagcaaa tcactgtggt cggtgctact     480
tccggtgaca ctggttctgc agccatctac ggtttaagag gcaaaaagga cgtttccgtt     540
ttcatcttat atccaaccgg tagaatttcc ccaattcaag aagaacaaat gaccaccgtt     600
ccagatgaaa acgtccagac tttgtctgtt accggtactt tcgacaactg tcaagatatc     660
gtcaaagcta ttttcggtga caaagaattc aactctaaac acaacgtcgg tgctgttaac     720
tccatcaact gggcaagaat cttggcccaa atgacctatt acttttattc attcttccaa     780
gccaccaacg gtaaggactc caagaaggtc aagttcgttg tgccaagtgg gaacttcggt     840
gatatattgg ccggttattt tgccaagaaa atgggtttgc ctattgaaaa actggccatc     900
gctaccaatg aaaacgacat tttggacaga ttttttgaaat ctggtctata cgaaagatca     960
gacaaggttc tgctgactttt atccccagca atggatatct taatctcttc taactttgaa    1020
agactactat ggtacctagc tcgtgaatac tagctaatg gtgatgattt gaaagccggt    1080
gaaatcgtca caattggtt ccaggaattg aagaccaacg gtaagttcca agttgacaaa     1140
tccatcattg aaggcgcatc aaaggacttt acatcagaaa gagtttccaa tgaagaaaca    1200
tctgaaacaa tcaagaagat ctacgaatca tctgtaaatc caaaacatta catcttagat    1260
cctcacacag ctgtcggtgt ttgcgccaca gaaagattga ttgcaaaaga taatgacaag    1320
tccatccaat acatttctct atctaccgct cacccagcta aatttgccga tgctgtaaac    1380
aatgcattgt ctggatttc caattattca tttgaaaagg atgttttgcc tgaggaattg    1440
aagaaactat ccacattaaa gaagaaatta aaattcatcg aaagagctga cgttgaattg    1500
gtcaaaaacg ctattgaaga agaacttgct aaaatgaaat ataa                     1545
```

<210> SEQ ID NO 7
<211> LENGTH: 514
<212> TYPE: PRT
<213> ORGANISM: Saccharomyces cerevisiae
<220> FEATURE:
<223> OTHER INFORMATION: HOMOSERINE KINASE (THR4)
<220> FEATURE:
<223> OTHER INFORMATION: HOMOSERINE KINASE (THR4)

<400> SEQUENCE: 7

```
Met Pro Asn Ala Ser Gln Val Tyr Arg Ser Thr Arg Ser Ser Ser Pro
1               5                   10                  15

Lys Thr Ile Ser Phe Glu Glu Ala Ile Ile Gln Gly Leu Ala Thr Asp
            20                  25                  30

Gly Gly Leu Phe Ile Pro Pro Thr Ile Pro Gln Val Asp Gln Ala Thr
```

```
            35                  40                  45
Leu Phe Asn Asp Trp Ser Lys Leu Ser Phe Gln Asp Leu Ala Phe Ala
 50                  55                  60

Ile Met Arg Leu Tyr Ile Ala Gln Glu Glu Ile Pro Asp Ala Asp Leu
 65                  70                  75                  80

Lys Asp Leu Ile Lys Arg Ser Tyr Ser Thr Phe Arg Ser Asp Glu Val
                 85                  90                  95

Thr Pro Leu Val Gln Asn Val Thr Gly Asp Lys Glu Asn Leu His Ile
            100                 105                 110

Leu Glu Leu Phe His Gly Pro Thr Tyr Ala Phe Lys Asp Val Ala Leu
        115                 120                 125

Gln Phe Val Gly Asn Leu Phe Glu Tyr Phe Leu Gln Arg Thr Asn Ala
    130                 135                 140

Asn Leu Pro Glu Gly Glu Lys Lys Gln Ile Thr Val Val Gly Ala Thr
145                 150                 155                 160

Ser Gly Asp Thr Gly Ser Ala Ala Ile Tyr Gly Leu Arg Gly Lys Lys
                165                 170                 175

Asp Val Ser Val Phe Ile Leu Tyr Pro Thr Gly Arg Ile Ser Pro Ile
            180                 185                 190

Gln Glu Glu Gln Met Thr Thr Val Pro Asp Glu Asn Val Gln Thr Leu
        195                 200                 205

Ser Val Thr Gly Thr Phe Asp Asn Cys Gln Asp Ile Val Lys Ala Ile
    210                 215                 220

Phe Gly Asp Lys Glu Phe Asn Ser Lys His Asn Val Gly Ala Val Asn
225                 230                 235                 240

Ser Ile Asn Trp Ala Arg Ile Leu Ala Gln Met Thr Tyr Tyr Phe Tyr
                245                 250                 255

Ser Phe Phe Gln Ala Thr Asn Gly Lys Asp Ser Lys Lys Val Lys Phe
            260                 265                 270

Val Val Pro Ser Gly Asn Phe Gly Asp Ile Leu Ala Gly Tyr Phe Ala
        275                 280                 285

Lys Lys Met Gly Leu Pro Ile Glu Lys Leu Ala Ile Ala Thr Asn Glu
    290                 295                 300

Asn Asp Ile Leu Asp Arg Phe Leu Lys Ser Gly Leu Tyr Glu Arg Ser
305                 310                 315                 320

Asp Lys Val Ala Ala Thr Leu Ser Pro Ala Met Asp Ile Leu Ile Ser
                325                 330                 335

Ser Asn Phe Glu Arg Leu Leu Trp Tyr Leu Ala Arg Glu Tyr Leu Ala
            340                 345                 350

Asn Gly Asp Asp Leu Lys Ala Gly Glu Ile Val Asn Asn Trp Phe Gln
        355                 360                 365

Glu Leu Lys Thr Asn Gly Lys Phe Gln Val Asp Lys Ser Ile Ile Glu
    370                 375                 380

Gly Ala Ser Lys Asp Phe Thr Ser Glu Arg Val Ser Asn Glu Glu Thr
385                 390                 395                 400

Ser Glu Thr Ile Lys Lys Ile Tyr Glu Ser Ser Val Asn Pro Lys His
                405                 410                 415

Tyr Ile Leu Asp Pro His Thr Ala Val Gly Val Cys Ala Thr Glu Arg
            420                 425                 430

Leu Ile Ala Lys Asp Asn Asp Lys Ser Ile Gln Tyr Ile Ser Leu Ser
        435                 440                 445

Thr Ala His Pro Ala Lys Phe Ala Asp Ala Val Asn Asn Ala Leu Ser
    450                 455                 460
```

```
Gly Phe Ser Asn Tyr Ser Phe Glu Lys Asp Val Leu Pro Glu Glu Leu
465                 470                 475                 480

Lys Lys Leu Ser Thr Leu Lys Lys Lys Leu Lys Phe Ile Glu Arg Ala
                485                 490                 495

Asp Val Glu Leu Val Lys Asn Ala Ile Glu Glu Glu Leu Ala Lys Met
            500                 505                 510

Lys Leu

<210> SEQ ID NO 8
<211> LENGTH: 1583
<212> TYPE: DNA
<213> ORGANISM: Saccharomyces cerevisiae
<220> FEATURE:
<223> OTHER INFORMATION: ASPARTOKINASE (HOM3)
<220> FEATURE:
<223> OTHER INFORMATION: ASPARTOKINASE (HOM3)

<400> SEQUENCE: 8
```

| | | | | | |
|---|---|---|---|---|---|
| atgccaatgg | atttccaacc | tacatcaagt | cattcgaact | gggtcgtgca | aaagttcggt | 60 |
| ggtacatctg | tcggtaaatt | tcccgtccaa | atagtggatg | acattgtgaa | gcactattct | 120 |
| aaacctgacg | gcccaaacaa | taatgtcgct | gtcgtttgtt | ccgcccgttc | ttcatacacc | 180 |
| aaggctgaag | gtaccacttc | tcgtcttttg | aaatgttgtg | atttggcttc | gcaagaatct | 240 |
| gaatttcaag | acattatcga | agttatcaga | caagaccata | tcgataatgc | cgaccgcttc | 300 |
| attctcaatc | ctgccttgca | agccaagtta | gtggatgata | ccaataaaga | acttgaactg | 360 |
| gtcaagaaat | atttaaatgc | ttcaaaagtt | ttgggtgaag | tgagttcacg | tacagtagat | 420 |
| ctggtgatgt | catgtggtga | aagttgagt | tgtttgttca | tgactgcttt | atgtaatgac | 480 |
| cgtggctgta | aggccaaata | tgtggatttg | agccacattg | ttccctctga | tttcagtgcc | 540 |
| agcgctttgg | ataacagttt | ctacactttc | ctggttcaag | cattgaaaga | aaaattggcc | 600 |
| ccctttgtaa | gtgctaaaga | gcgtatcgtt | ccagtcttta | cagggttttt | tggtttagtt | 660 |
| ccaactggtc | ttctgaatgg | tgttggtcgt | ggctataccg | atttatgtgc | cgctttgata | 720 |
| gcagttgctg | taaatgctga | tgaactacaa | gtttggaagg | aagttgatgg | tatatttact | 780 |
| gctgatcctc | gtaaggttcc | tgaagcacgt | ttgctagaca | gtgttactcc | agaagaagct | 840 |
| tctgaattaa | catattatgg | ttccgaagtt | atacatcctt | ttacgatgga | acaagttatt | 900 |
| agggctaaga | ttcctattag | aatcaagaat | gttcaaaatc | cattaggtaa | cggtaccatt | 960 |
| atctacccag | ataatgtagc | aaagaagggg | aatctactc | caccacatcc | tcctgagaac | 1020 |
| ttatcctcat | ctttctatga | aaagagaaag | agaggtgcca | ctgctatcac | caccaaaaat | 1080 |
| gacattttcg | tcatcaacat | tcattccaat | aagaaaaccc | tatcccatgg | tttcctagct | 1140 |
| caaatattta | ccatcctgga | taagtacaag | ttagtcgtag | atttaatatc | tacttctgaa | 1200 |
| gttcatgttt | cgatggcttt | gcccattcca | gatgcagact | cattaaaatc | tctgagacaa | 1260 |
| gctgaggaaa | aattgagaat | tttaggttct | gttgatatca | caagaagtt | gtctattgtt | 1320 |
| tcattagttg | gtaaacatat | gaaacaatac | atcggcattg | ctggtaccat | gtttactact | 1380 |
| cttgctgaag | aaggcatcaa | cattgaaatg | atttctcaag | gggcaaatga | aataaacata | 1440 |
| tcctgcgtta | tcaatgaatc | tgactccata | aaagcgctac | aatgtattca | tgccaagtta | 1500 |
| ctaagtgagc | ggacaaatac | ttcaaaccaa | tttgaacatg | ccattgatga | acgtttagaa | 1560 |
| caattgaaaa | gacttggaat | taa | | | | 1583 |

```
<210> SEQ ID NO 9
<211> LENGTH: 526
<212> TYPE: PRT
<213> ORGANISM: Saccharomyces cerevisiae
<220> FEATURE:
<223> OTHER INFORMATION: ASPARTOKINASE (HOM3)
<220> FEATURE:
<223> OTHER INFORMATION: ASPARTOKINASE (HOM3)

<400> SEQUENCE: 9
```

Pro Met Asp Phe Gln Pro Thr Ser Ser His Ser Asn Trp Val Val Gln
1               5                   10                  15

Lys Phe Gly Gly Thr Ser Val Gly Lys Phe Pro Val Gln Ile Val Asp
            20                  25                  30

Asp Ile Val Lys His Tyr Ser Lys Pro Asp Gly Pro Asn Asn Asn Val
        35                  40                  45

Ala Val Val Cys Ser Ala Arg Ser Ser Tyr Thr Lys Ala Glu Gly Thr
    50                  55                  60

Thr Ser Arg Leu Leu Lys Cys Cys Asp Leu Ala Ser Gln Glu Ser Glu
65                  70                  75                  80

Phe Gln Asp Ile Ile Glu Val Ile Arg Gln Asp His Ile Asp Asn Ala
                85                  90                  95

Asp Arg Phe Ile Leu Asn Pro Ala Leu Gln Ala Lys Leu Val Asp Asp
            100                 105                 110

Thr Asn Lys Glu Leu Glu Leu Val Lys Lys Tyr Leu Asn Ala Ser Lys
        115                 120                 125

Val Leu Gly Glu Val Ser Ser Arg Thr Val Asp Leu Val Met Ser Cys
    130                 135                 140

Gly Glu Lys Leu Ser Cys Leu Phe Met Thr Ala Leu Cys Asn Asp Arg
145                 150                 155                 160

Gly Cys Lys Ala Lys Tyr Val Asp Leu Ser His Ile Val Pro Ser Asp
                165                 170                 175

Phe Ser Ala Ser Ala Leu Asp Asn Ser Phe Tyr Thr Phe Leu Val Gln
            180                 185                 190

Ala Leu Lys Glu Lys Leu Ala Pro Phe Val Ser Ala Lys Glu Arg Ile
        195                 200                 205

Val Pro Val Phe Thr Gly Phe Phe Gly Leu Val Pro Thr Gly Leu Leu
    210                 215                 220

Asn Gly Val Gly Arg Gly Tyr Thr Asp Leu Cys Ala Ala Leu Ile Ala
225                 230                 235                 240

Val Ala Val Asn Ala Asp Glu Leu Gln Val Trp Lys Glu Val Asp Gly
                245                 250                 255

Ile Phe Thr Ala Asp Pro Arg Lys Val Pro Glu Ala Arg Leu Leu Asp
            260                 265                 270

Ser Val Thr Pro Glu Glu Ala Ser Glu Leu Thr Tyr Tyr Gly Ser Glu
        275                 280                 285

Val Ile His Pro Phe Thr Met Glu Gln Val Ile Arg Ala Lys Ile Pro
    290                 295                 300

Ile Arg Ile Lys Asn Val Gln Asn Pro Leu Gly Asn Gly Thr Ile Ile
305                 310                 315                 320

Tyr Pro Asp Asn Val Ala Lys Lys Gly Glu Ser Thr Pro Pro His Pro
                325                 330                 335

Pro Glu Asn Leu Ser Ser Ser Phe Tyr Glu Lys Arg Lys Arg Gly Ala
            340                 345                 350

Thr Ala Ile Thr Thr Lys Asn Asp Ile Phe Val Ile Asn Ile His Ser
        355                 360                 365

```
Asn Lys Lys Thr Leu Ser His Gly Phe Leu Ala Gln Ile Phe Thr Ile
    370                 375                 380
Leu Asp Lys Tyr Lys Leu Val Val Asp Leu Ile Ser Thr Ser Glu Val
385                 390                 395                 400
His Val Ser Met Ala Leu Pro Ile Pro Asp Ala Asp Ser Leu Lys Ser
                405                 410                 415
Leu Arg Gln Ala Glu Glu Lys Leu Arg Ile Leu Gly Ser Val Asp Ile
            420                 425                 430
Thr Lys Lys Leu Ser Ile Val Ser Leu Val Gly Lys His Met Lys Gln
        435                 440                 445
Tyr Ile Gly Ile Ala Gly Thr Met Phe Thr Thr Leu Ala Glu Glu Gly
    450                 455                 460
Ile Asn Ile Glu Met Ile Ser Gln Gly Ala Asn Glu Ile Asn Ile Ser
465                 470                 475                 480
Cys Val Ile Asn Glu Ser Asp Ser Ile Lys Ala Leu Gln Cys Ile His
                485                 490                 495
Ala Lys Leu Leu Ser Glu Arg Thr Asn Thr Ser Asn Gln Phe Glu His
            500                 505                 510
Ala Ile Asp Glu Arg Leu Glu Gln Leu Lys Arg Leu Gly Ile
        515                 520                 525

<210> SEQ ID NO 10
<211> LENGTH: 1215
<212> TYPE: DNA
<213> ORGANISM: Bacillus subtilis
<220> FEATURE:
<223> OTHER INFORMATION: ASPARTATE KINASE (AK)
<220> FEATURE:
<223> OTHER INFORMATION: ASPARTATE KINASE (AK)

<400> SEQUENCE: 10
atggctatta tcgtccaaaa attcggagga actagcgtta aggatgacaa agggagaaag      60
ttggccttag gcacattaa ggaggcaatt tcagagggtt ataaggtggt tgtagttgta     120
tcggctatgg gtagaaaagg ggaccccctac gcgacggact cactattggg tttactttac     180
ggggatcaat cagcaatcag cccaagagag caggatctgc tgctatcatg tggagaaacc     240
atatcctcgg ttgtgttcac cagcatgtta ttagataatg gagtaaaagc agcagccctg     300
acgggagccc aggctggttt tttaaccaac gatcagcata ctaatgcaaa aattatagag     360
atgaagcctg aacgtctttt cagtgttctt gcaaaccacg acgcagttgt cgtcgctgga     420
tttcagggcg ctaccgagaa aggagatact accacaatcg gtagaggtgg ctcggacacg     480
tcagctgcag ccctaggtgc tgctgttgat gcagagtaca tagatatctt tactgacgta     540 gaagggggtga tgaccgcaga tccaagagta gtagaaaatg caaagccact accagtggta     600
acttataccg aaatctgcaa cttggcttac caaggtgcta aggtaatatc tccaagagct     660
gtggaaattg ctatgcaagc aaaggttcct atccgtgtta ggagtactta ttcaaacgat     720
aaaggtacgt tagtaactag tcatcatagt tccaaagttg gctctgacgt ctttgaaagg     780
ttaatcactg gtatcgcaca tgttaaagac gtcactcaat tcaaggtccc ggcgaaaata     840
ggtcaatata acgttcaaac agaagtgttt aaagcgatgg cgaatgccgg tatatctgtc     900
gatttcttta atattacacc ctctgaaata gtatatacag tcgcgggtaa taagactgaa     960
acagctcaaa ggattttgat ggatatgggc tatgatccta tggtcacaag aaattgtgcc    1020
aaggtgtctg ccgtgggtgc tggcattatg ggtgtcccag gtgtgacatc gaaaattgtt    1080
```

-continued

```
tctgccttat ctgaaaaaga aattccgatt ttgcaatctg ctgattccca tacaacaatt    1140
tgggttttgg ttcatgaagc cgatatggtt cctgctgtta atgccttgca cgaagttttt    1200
gaattgtcca aataa                                                      1215
```

<210> SEQ ID NO 11
<211> LENGTH: 404
<212> TYPE: PRT
<213> ORGANISM: Bacillus subtilis
<220> FEATURE:
<223> OTHER INFORMATION: ASPARTATE KINASE (AK)
<220> FEATURE:
<223> OTHER INFORMATION: ASPARTATE KINASE (AK)

<400> SEQUENCE: 11

```
Met Ala Ile Ile Val Gln Lys Phe Gly Gly Thr Ser Val Lys Asp Asp
1               5                   10                  15

Lys Gly Arg Lys Leu Ala Leu Gly His Ile Lys Glu Ala Ile Ser Glu
                20                  25                  30

Gly Tyr Lys Val Val Val Val Ser Ala Met Gly Arg Lys Gly Asp
                35                  40                  45

Pro Tyr Ala Thr Asp Ser Leu Leu Gly Leu Leu Tyr Gly Asp Gln Ser
    50                  55                  60

Ala Ile Ser Pro Arg Glu Gln Asp Leu Leu Leu Ser Cys Gly Glu Thr
65                  70                  75                  80

Ile Ser Ser Val Val Phe Thr Ser Met Leu Leu Asp Asn Gly Val Lys
                85                  90                  95

Ala Ala Ala Leu Thr Gly Ala Gln Ala Gly Phe Leu Thr Asn Asp Gln
            100                 105                 110

His Thr Asn Ala Lys Ile Ile Glu Met Lys Pro Glu Arg Leu Phe Ser
        115                 120                 125

Val Leu Ala Asn His Asp Ala Val Val Val Ala Gly Phe Gln Gly Ala
    130                 135                 140

Thr Glu Lys Gly Asp Thr Thr Thr Ile Gly Arg Gly Gly Ser Asp Thr
145                 150                 155                 160

Ser Ala Ala Ala Leu Gly Ala Ala Val Asp Ala Glu Tyr Ile Asp Ile
                165                 170                 175

Phe Thr Asp Val Glu Gly Val Met Thr Ala Asp Pro Arg Val Val Glu
            180                 185                 190

Asn Ala Lys Pro Leu Pro Val Val Thr Tyr Thr Glu Ile Cys Asn Leu
        195                 200                 205

Ala Tyr Gln Gly Ala Lys Val Ile Ser Pro Arg Ala Val Glu Ile Ala
    210                 215                 220

Met Gln Ala Lys Val Pro Ile Arg Val Arg Ser Thr Tyr Ser Asn Asp
225                 230                 235                 240

Lys Gly Thr Leu Val Thr Ser His His Ser Ser Lys Val Gly Ser Asp
                245                 250                 255

Val Phe Glu Arg Leu Ile Thr Gly Ile Ala His Val Lys Asp Val Thr
            260                 265                 270

Gln Phe Lys Val Pro Ala Lys Ile Gly Gln Tyr Asn Val Gln Thr Glu
        275                 280                 285

Val Phe Lys Ala Met Ala Asn Ala Gly Ile Ser Val Asp Phe Phe Asn
    290                 295                 300

Ile Thr Pro Ser Glu Ile Val Tyr Thr Val Ala Gly Asn Lys Thr Glu
305                 310                 315                 320

Thr Ala Gln Arg Ile Leu Met Asp Met Gly Tyr Asp Pro Met Val Thr
```

```
              325                 330                 335
Arg Asn Cys Ala Lys Val Ser Ala Val Gly Ala Gly Ile Met Gly Val
            340                 345                 350

Pro Gly Val Thr Ser Lys Ile Val Ser Ala Leu Ser Glu Lys Glu Ile
            355                 360                 365

Pro Ile Leu Gln Ser Ala Asp Ser His Thr Thr Ile Trp Val Leu Val
370                 375                 380

His Glu Ala Asp Met Val Pro Ala Val Asn Ala Leu His Glu Val Phe
385                 390                 395                 400

Glu Leu Ser Lys

<210> SEQ ID NO 12
<211> LENGTH: 1257
<212> TYPE: DNA
<213> ORGANISM: Saccharomyces cerevisiae
<220> FEATURE:
<223> OTHER INFORMATION: ASPARTATE TRANSAMINASE (AAT2)
<220> FEATURE:
<223> OTHER INFORMATION: ASPARTATE TRANSAMINASE (AAT2)

<400> SEQUENCE: 12
atgtctgcca ctctgttcaa taacatcgaa ttgctgcccc ctgatgccct ttttggtatt      60
aagcaaaggt acgggcaaga tcaacgtgct accaaggtcg acttgggtat cggggcctac    120
agagacgaca acgtaaaacc atgggtcttg ccaagtgtta aagccgccga aaagctaatt    180
cataacgaca gctcctacaa ccatgaatac ctcggtatta ccggtctgcc aagtttgaca    240
tctaacgccg ccaagatcat cttcggtacg caatccgatg cctttcagga agacagagta    300
atctcagtac aatcactgtc tggtacgggt gctcttcata tatctgcgaa gttttttttca    360 aaattcttcc cagataaact ggtctatttg tctaagccta cttgggccaa ccacatggcc    420 attttgaga tcaaggctt gaaaacggcg acttaccctt actgggccaa cgaaactaag    480
tctttggacc taaacggctt tctaaatgct attcaaaaag ctccagaggg ctccattttc    540
gttctgcact cttgcgccca taacccaact ggtctggacc ctactagtga acaatgggtt    600
caaatcgttg atgctatcgc ctcaaagaac cacatcgcct atttgacac cgcctaccaa    660 gggtttgcca ctggagattt ggacaaggat gcctatgctg tgcgtctagg tgtggagaag    720 cttttcaacgg tctctcccgt cttttgtctgt cagtcctttg ccaagaacgc cggtatgtac    780
ggtgagcgtg taggttgttt ccatctagca cttacaaaac aagctcaaaa caaaactata    840
aagcctgctg ttacatctca attggccaaa atcattcgta gtgaagtgtc caacccaccc    900
gcctacggcg ctaagattgt cgctaaactg ttggaaacgc cagaattaac ggaacagtgg    960
cacaaggata tggttaccat gtcctccaga attacgaaaa tgaggcacgc attaagagac   1020
catttagtca agttgggcac tcctggcaac tgggatcata tagtaaatca atgcgggatg   1080
ttctccttta cagggttgac tcctcaaatg gttaaacgac ttgaagaaac ccacgcagtt   1140
tacttggttg cctcaggtag agcttctatt gctggattga atcaaggaaa cgtggaatac   1200
gtggctaaag ccattgatga agtggtgcgc ttctatacta ttgaagctaa attgtaa     1257

<210> SEQ ID NO 13
<211> LENGTH: 418
<212> TYPE: PRT
<213> ORGANISM: Saccharomyces cerevisiae
<220> FEATURE:
<223> OTHER INFORMATION: ASPARTATE TRANSAMINASE (AAT2)
<220> FEATURE:
<223> OTHER INFORMATION: ASPARTATE TRANSAMINASE (AAT2)
```

<400> SEQUENCE: 13

```
Met Ser Ala Thr Leu Phe Asn Asn Ile Glu Leu Leu Pro Pro Asp Ala
1               5                   10                  15

Leu Phe Gly Ile Lys Gln Arg Tyr Gly Gln Asp Gln Arg Ala Thr Lys
            20                  25                  30

Val Asp Leu Gly Ile Gly Ala Tyr Arg Asp Asp Asn Gly Lys Pro Trp
        35                  40                  45

Val Leu Pro Ser Val Lys Ala Glu Lys Leu Ile His Asn Asp Ser
    50                  55                  60

Ser Tyr Asn His Glu Tyr Leu Gly Ile Thr Gly Leu Pro Ser Leu Thr
65                  70                  75                  80

Ser Asn Ala Ala Lys Ile Ile Phe Gly Thr Gln Ser Asp Ala Phe Gln
                85                  90                  95

Glu Asp Arg Val Ile Ser Val Gln Ser Leu Ser Gly Thr Gly Ala Leu
            100                 105                 110

His Ile Ser Ala Lys Phe Phe Ser Lys Phe Pro Asp Lys Leu Val
        115                 120                 125

Tyr Leu Ser Lys Pro Thr Trp Ala Asn His Met Ala Ile Phe Glu Asn
130                 135                 140

Gln Gly Leu Lys Thr Ala Thr Tyr Pro Tyr Trp Ala Asn Glu Thr Lys
145                 150                 155                 160

Ser Leu Asp Leu Asn Gly Phe Leu Asn Ala Ile Gln Lys Ala Pro Glu
                165                 170                 175

Gly Ser Ile Phe Val Leu His Ser Cys Ala His Asn Pro Thr Gly Leu
            180                 185                 190

Asp Pro Thr Ser Glu Gln Trp Val Gln Ile Val Asp Ala Ile Ala Ser
        195                 200                 205

Lys Asn His Ile Ala Leu Phe Asp Thr Ala Tyr Gln Gly Phe Ala Thr
    210                 215                 220

Gly Asp Leu Asp Lys Asp Ala Tyr Ala Val Arg Leu Gly Val Glu Lys
225                 230                 235                 240

Leu Ser Thr Val Ser Pro Val Phe Val Cys Gln Ser Phe Ala Lys Asn
                245                 250                 255

Ala Gly Met Tyr Gly Glu Arg Val Gly Cys Phe His Leu Ala Leu Thr
            260                 265                 270

Lys Gln Ala Gln Asn Lys Thr Ile Lys Pro Ala Val Thr Ser Gln Leu
        275                 280                 285

Ala Lys Ile Ile Arg Ser Glu Val Ser Asn Pro Pro Ala Tyr Gly Ala
    290                 295                 300

Lys Ile Val Ala Lys Leu Leu Glu Thr Pro Glu Leu Thr Glu Gln Trp
305                 310                 315                 320

His Lys Asp Met Val Thr Met Ser Ser Arg Ile Thr Lys Met Arg His
                325                 330                 335

Ala Leu Arg Asp His Leu Val Lys Leu Gly Thr Pro Gly Asn Trp Asp
            340                 345                 350

His Ile Val Asn Gln Cys Gly Met Phe Ser Phe Thr Gly Leu Thr Pro
        355                 360                 365

Gln Met Val Lys Arg Leu Glu Thr His Ala Val Tyr Leu Val Ala
    370                 375                 380

Ser Gly Arg Ala Ser Ile Ala Gly Leu Asn Gln Gly Asn Val Glu Tyr
385                 390                 395                 400

Val Ala Lys Ala Ile Asp Glu Val Val Arg Phe Tyr Thr Ile Glu Ala
```

```
                    405            410            415

Lys Leu

<210> SEQ ID NO 14
<211> LENGTH: 1317
<212> TYPE: DNA
<213> ORGANISM: Entodinium caudatum
<220> FEATURE:
<223> OTHER INFORMATION: GLUTAMATE DESHYDROGENASE (GDH)
<220> FEATURE:
<223> OTHER INFORMATION: GLUTAMATE DESHYDROGENASE (GDH)

<400> SEQUENCE: 14
atgatagatt tagaagcgag aaaccctgct caacccgaat tcattcaagc cagtagagaa      60
gtaatcgaat cgatcattga tgttgttaat agcaatccga aatacctgga aaacaaaatt     120
ttggagagaa ttacggaacc aaacctaatt cacgaattca agtcgaatg ggagaatgac      180 aagcacgaaa tcatggtgaa caaaggttat cgtattcagt tcaataatgc gataggtccc     240
tataagggag gcctaaggtt tcacagagca gtcactctag gtactctgaa attccttggt     300
tttgaacaga tatttaagaa ttccttgaca ggattaccta tgggaggtgg caaaggtggt     360
tcagattttg atcctagagg taaatcagat gccgagattt taagattctg taggtctttt     420
atgacttcgt tgttcaaata tattgggcca gagatagatg ttcctgctgg agatataggt     480
gtcggaggta gggaaattgg ttacttgttt ggccaataca aaagactgac ccaacaacat     540
gaaggagttc taactggtaa gggtcttaac tggggtggct ctcttgttag acctgaagcc     600
acaggttttg aacgatgta ttttgctaac gaagtcttac atgcacatgg tgacgacatc      660
aaggggaaaa ccattgccat atccggattt ggtaatgttg cctttggtgc tgtcttaaaa     720
gcgaaacaat taggcgctaa ggtagtcact atatctggcc cagatggtta catttatgac     780
gagaatggga taaacaccga cgagaaaatc aactacatgt tggaattaag agcctcaaat     840
aatgatgtgg ttgcgccatt tgcagagaag tttggtgcaa aattcatacc agggaagaag     900
ccatgggaag ttccagtgga tatggctttt ccctgtgcca ttcagaacga attgaatgcc     960
gaagatgctg ccacttttaca taagaatgga gtgaaatatg tgatcgagac atccaatatg    1020
ggctgtacag cagatgctgt gcaatacttc attaagaacc gtattgtttt cgctccgggt    1080
aaagcagcta atgctggtgg tgttgcagta tctgggttgg aaatgagcca aaactcaatg    1140
aagttgaact ggacagctga agaagttgac gctaaattga agaatatcat gaccaatatt    1200
catgcaagtt gcgtaaagga aggaaaagag agtgacgggt atatcaatta cgttaaaggc    1260
gcaaatatag caggcttcaa gaaagtagct gatgcaatgg tagatcttgg ctattaa       1317

<210> SEQ ID NO 15
<211> LENGTH: 438
<212> TYPE: PRT
<213> ORGANISM: Entodinium caudatum
<220> FEATURE:
<223> OTHER INFORMATION: GLUTAMATE DESHYDROGENASE (GDH)
<220> FEATURE:
<223> OTHER INFORMATION: GLUTAMATE DESHYDROGENASE (GDH)

<400> SEQUENCE: 15

Met Ile Asp Leu Glu Ala Arg Asn Pro Ala Gln Pro Glu Phe Ile Gln
1               5                   10                  15

Ala Ser Arg Glu Val Ile Glu Ser Ile Ile Asp Val Val Asn Ser Asn
            20                  25                  30

Pro Lys Tyr Leu Glu Asn Lys Ile Leu Glu Arg Ile Thr Glu Pro Asn
```

```
            35                  40                  45
Leu Ile His Glu Phe Lys Val Glu Trp Glu Asn Asp Lys His Glu Ile
 50                  55                  60
Met Val Asn Lys Gly Tyr Arg Ile Gln Phe Asn Asn Ala Ile Gly Pro
 65                      70                  75                  80
Tyr Lys Gly Gly Leu Arg Phe His Arg Ala Val Thr Leu Gly Thr Leu
                     85                  90                  95
Lys Phe Leu Gly Phe Glu Gln Ile Phe Lys Asn Ser Leu Thr Gly Leu
                    100                 105                 110
Pro Met Gly Gly Gly Lys Gly Ser Asp Phe Asp Pro Arg Gly Lys
                    115                 120                 125
Ser Asp Ala Glu Ile Leu Arg Phe Cys Arg Ser Phe Met Thr Ser Leu
130                 135                 140
Phe Lys Tyr Ile Gly Pro Glu Ile Asp Val Pro Ala Gly Asp Ile Gly
145                 150                 155                 160
Val Gly Gly Arg Glu Ile Gly Tyr Leu Phe Gly Gln Tyr Lys Arg Leu
                    165                 170                 175
Thr Gln Gln His Glu Gly Val Leu Thr Gly Lys Gly Leu Asn Trp Gly
                    180                 185                 190
Gly Ser Leu Val Arg Pro Glu Ala Thr Gly Phe Gly Thr Met Tyr Phe
            195                 200                 205
Ala Asn Glu Val Leu His Ala His Gly Asp Asp Ile Lys Gly Lys Thr
210                 215                 220
Ile Ala Ile Ser Gly Phe Gly Asn Val Ala Phe Gly Ala Val Leu Lys
225                 230                 235                 240
Ala Lys Gln Leu Gly Ala Lys Val Val Thr Ile Ser Gly Pro Asp Gly
                    245                 250                 255
Tyr Ile Tyr Asp Glu Asn Gly Ile Asn Thr Asp Glu Lys Ile Asn Tyr
                    260                 265                 270
Met Leu Glu Leu Arg Ala Ser Asn Asn Asp Val Val Ala Pro Phe Ala
            275                 280                 285
Glu Lys Phe Gly Ala Lys Phe Ile Pro Gly Lys Lys Pro Trp Glu Val
            290                 295                 300
Pro Val Asp Met Ala Phe Pro Cys Ala Ile Gln Asn Glu Leu Asn Ala
305                 310                 315                 320
Glu Asp Ala Ala Thr Leu His Lys Asn Gly Val Lys Tyr Val Ile Glu
                    325                 330                 335
Thr Ser Asn Met Gly Cys Thr Ala Asp Ala Val Gln Tyr Phe Ile Lys
                    340                 345                 350
Asn Arg Ile Val Phe Ala Pro Gly Lys Ala Ala Asn Ala Gly Gly Val
            355                 360                 365
Ala Val Ser Gly Leu Glu Met Ser Gln Asn Ser Met Lys Leu Asn Trp
            370                 375                 380
Thr Ala Glu Glu Val Asp Ala Lys Leu Lys Asn Ile Met Thr Asn Ile
385                 390                 395                 400
His Ala Ser Cys Val Lys Glu Gly Lys Glu Ser Asp Gly Tyr Ile Asn
                    405                 410                 415
Tyr Val Lys Gly Ala Asn Ile Ala Gly Phe Lys Lys Val Ala Asp Ala
                    420                 425                 430
Met Val Asp Leu Gly Tyr
            435

<210> SEQ ID NO 16
```

<211> LENGTH: 1080
<212> TYPE: DNA
<213> ORGANISM: Saccharomyces cerevisiae
<220> FEATURE:
<223> OTHER INFORMATION: HOMOSERINE DESHYDROGENASE (HOM6)
<220> FEATURE:
<223> OTHER INFORMATION: HOMOSERINE DESHYDROGENASE (HOM6)

<400> SEQUENCE: 16

```
atgagcacta aagttgttaa tgttgccgtt atcggtgccg gtgttgttgg ttcagctttc      60
ttggatcaat tgttagccat gaagtctacc attacttaca atctagttct tttggctgaa     120
gctgagcgtt ctttaatctc caaggacttt tctccattaa atgttggttc tgattggaag     180
gctgctttag cagcctccac tactaaaacg ttgccttttgg atgatttaat tgctcatttg    240
aagacttcac ctaagccagt cattttggtt gataacactt ccagcgctta cattgctggt    300
ttttacacta agtttgtcga aaatggtatt tccattgcta ctccaaacaa gaaggccttt    360
tcctctgatt tggctacctg gaaggctctt ttctcaaata agccaactaa cggttttgtc    420
tatcatgaag ctaccgtcgg tgctggtttg cctatcatca gtttcttaag agaaattat    480
caaaccggtg acgaagttga aaaaattgaa ggtatcttct ctggtactct atcttatatt    540
ttcaacgagt tctccactag tcaagctaac gacgtcaaat tctctgatgt tgtcaaagtt    600
gctaaaaaat tgggttatac tgaaccagat ccaagagatg atttgaatgg ttggatgtt    660
gctagaaagg ttaccattgt tggtaggata tctggtgtgg aagttgaatc tccaacttcc    720
ttccctgtcc agtctttgat tccaaaacca ttggaatctg tcaagtctgc tgatgaattc    780
ttggaaaaat tatctgatta cgataaagat ttgactcaat tgaagaagga agctgccact    840
gaaaataagg tattgagatt cattggtaaa gtcgatgttg ccaccaaatc tgtgtctgta    900
ggaattgaaa agtacgatta ctcacaccca ttcgcatcat tgaagggatc agataacgtt    960
atttccatca agactaagcg ttacaccaat cctgttgtca ttcaaggtgc cggtgccggt   1020
gctgccgtta ctgccgctgg tgttttgggt gatgttatca agattgctca aagactttaa  1080
```

<210> SEQ ID NO 17
<211> LENGTH: 308
<212> TYPE: PRT
<213> ORGANISM: Saccharomyces cerevisiae
<220> FEATURE:
<223> OTHER INFORMATION: HOMOSERINE DESHYDROGENASE (HOM6)
<220> FEATURE:
<223> OTHER INFORMATION: HOMOSERINE DESHYDROGENASE (HOM6)

<400> SEQUENCE: 17

```
Met Ser Thr Lys Val Val Asn Val Ala Val Ile Gly Ala Gly Val Val
1               5                   10                  15

Gly Ser Ala Phe Leu Asp Gln Leu Leu Ala Met Lys Ser Thr Ile Thr
            20                  25                  30

Tyr Asn Leu Val Leu Leu Ala Glu Ala Glu Arg Ser Leu Ile Ser Lys
        35                  40                  45

Asp Phe Ser Pro Leu Asn Val Gly Ser Asp Trp Lys Ala Ala Leu Ala
    50                  55                  60

Ala Ser Thr Thr Lys Thr Leu Pro Leu Asp Asp Leu Ile Ala His Leu
65                  70                  75                  80

Lys Thr Ser Pro Lys Pro Val Ile Leu Val Asp Asn Thr Ser Ser Ala
                85                  90                  95

Tyr Ile Ala Gly Phe Tyr Thr Lys Phe Val Glu Asn Gly Ile Ser Ile
            100                 105                 110
```

```
Ala Thr Pro Asn Lys Lys Ala Phe Ser Ser Asp Leu Ala Thr Trp Lys
            115                 120                 125

Ala Leu Phe Ser Asn Lys Pro Thr Asn Gly Phe Val Tyr His Glu Ala
        130                 135                 140

Thr Val Gly Ala Gly Leu Pro Ile Ile Ser Phe Leu Arg Glu Ile Ile
145                 150                 155                 160

Gln Thr Gly Asp Glu Val Glu Lys Ile Glu Gly Ile Phe Ser Gly Thr
                165                 170                 175

Leu Ser Tyr Ile Phe Asn Glu Phe Ser Thr Ser Gln Ala Asn Asp Val
            180                 185                 190

Lys Phe Ser Asp Val Val Lys Val Ala Lys Lys Leu Gly Tyr Thr Glu
        195                 200                 205

Pro Asp Pro Arg Asp Asp Leu Asn Gly Leu Asp Val Ala Arg Lys Val
210                 215                 220

Thr Ile Val Gly Arg Ile Ser Gly Val Glu Val Glu Ser Pro Thr Ser
225                 230                 235                 240

Phe Pro Val Gln Ser Leu Ile Pro Lys Pro Leu Glu Ser Val Lys Ser
                245                 250                 255

Ala Asp Glu Phe Leu Glu Lys Leu Ser Asp Tyr Asp Lys Asp Leu Thr
            260                 265                 270

Gln Leu Lys Lys Glu Ala Ala Thr Glu Asn Lys Val Leu Arg Phe Ile
        275                 280                 285

Gly Lys Val Asp Val Ala Thr Lys Ser Val Ser Val Gly Ile Glu Lys
290                 295                 300

Tyr Asp Tyr Ser
305

<210> SEQ ID NO 18
<211> LENGTH: 1461
<212> TYPE: DNA
<213> ORGANISM: Saccharomyces cerevisiae
<220> FEATURE:
<223> OTHER INFORMATION: HOMOSERINE O-ACETYLTRANSFERASE (MET2)
<220> FEATURE:
<223> OTHER INFORMATION: HOMOSERINE O-ACETYLTRANSFERASE (MET2)

<400> SEQUENCE: 18
atgtcgcata ctttaaaatc gaaaacgctc caagagctgg acattgagga gattaaggaa        60
actaacccat tgctcaaact agttcaaggg cagaggatta ttcaagttcc ggaactagtg       120
cttgagtctg gcgtggtcat aaataatttc cctattgctt ataagacgtg gggtacactg       180
aatgaagctg tgataatgt tctggtaatt tgtcatgcct tgactgggtc cgcagatgtt        240
gctgactggt ggggccctct tctgggtaac gacttagcat tcgacccatc aaggttttt        300 atcatatgtt taaactctat gggctctcca tatgggtctt tttcgccatt aacgataaat       360
gaggagacgg gcgttagata tggacccgaa ttcccattat gtactgtgcg cgatgacgtt       420
agagctcaca gaattgttct ggattctctg gagtaaagt caatagcctg tgttattggt        480
ggctctatgg ggggatgct gagtttggaa tgggctgcca tgtatggtaa ggaatatgtg       540
aagaatatgg ttgctctggc gacatcagca agacattctg cctggtgcat atcgtggtct       600
gaggctcaaa gacaatcgat ttactcagat cccaactact tggacgggta ctatccggta       660
gaggagcaac ctgtggccgg actatcggct gcacgtatgt ctgcattgtt gacgtacagg       720
acaagaaaca gtttcgagaa caaattctcc agaagatctc cttcaatagc acaacaacaa       780
aaagctcaaa gggaggagac acgcaaacca tctactgtca gcgaacactc cctacaaatc       840
```

```
cacaatgatg ggtataaaac aaaagccagc actgccatcg ctggcatttc tgggcaaaaa      900
ggtcaaagcg tggtgtccac cgcatcttct tcggattcat tgaattcttc aacatcgatg      960
acttcggtaa gttctgtaac gggtgaagtg aaggacataa agcctgcgca gacgtatttt     1020
tctgcacaaa gttacttgag gtaccagggc acaaagttca tcaataggtt cgacgccaat     1080
tgttacattg ccatcacacg taaactggat acgcacgatt tggcaagaga cagagtagat     1140
gacatcactg aggtccttc taccatccaa caaccatccc tgatcatcgg tatccaatct      1200
gatggactgt tcacatattc agaacaagaa ttttggctg agcacatacc gaagtcgcaa      1260
ttagaaaaaa ttgaatctcc cgaaggccac gatgccttcc tattggagtt taagctgata     1320
aacaaactga tagtacaatt tttaaaaacc aactgcaagg ccattaccga tgccgctcca     1380
agagcttggg gaggtgacgt tggtaacgat gaaacgaaga cgtctgtctt tggtgaggcc     1440
gaagaagtta ccaactggta g                                               1461
```

<210> SEQ ID NO 19
<211> LENGTH: 486
<212> TYPE: PRT
<213> ORGANISM: Saccharomyces cerevisiae
<220> FEATURE:
<223> OTHER INFORMATION: HOMOSERINE O-ACETYLTRANSFERASE (MET2)
<220> FEATURE:
<223> OTHER INFORMATION: HOMOSERINE O-ACETYLTRANSFERASE (MET2)

<400> SEQUENCE: 19

```
Met Ser His Thr Leu Lys Ser Lys Thr Leu Gln Glu Leu Asp Ile Glu
1               5                   10                  15

Glu Ile Lys Glu Thr Asn Pro Leu Leu Lys Leu Val Gln Gly Gln Arg
            20                  25                  30

Ile Val Gln Val Pro Glu Leu Val Leu Glu Ser Gly Val Val Ile Asn
        35                  40                  45

Asn Phe Pro Ile Ala Tyr Lys Thr Trp Gly Thr Leu Asn Glu Ala Gly
    50                  55                  60

Asp Asn Val Leu Val Ile Cys His Ala Leu Thr Gly Ser Ala Asp Val
65                  70                  75                  80

Ala Asp Trp Trp Gly Pro Leu Leu Gly Asn Asp Leu Ala Phe Asp Pro
                85                  90                  95

Ser Arg Phe Phe Ile Ile Cys Leu Asn Ser Met Gly Ser Pro Tyr Gly
            100                 105                 110

Ser Phe Ser Pro Leu Thr Ile Asn Glu Glu Thr Gly Val Arg Tyr Gly
        115                 120                 125

Pro Glu Phe Pro Leu Cys Thr Val Arg Asp Asp Val Arg Ala His Arg
    130                 135                 140

Ile Val Leu Asp Ser Leu Gly Val Lys Ser Ile Ala Cys Val Ile Gly
145                 150                 155                 160

Gly Ser Met Gly Gly Met Leu Ser Leu Glu Trp Ala Ala Met Tyr Gly
                165                 170                 175

Lys Glu Tyr Val Lys Asn Met Val Ala Leu Ala Thr Ser Ala Arg His
            180                 185                 190

Ser Ala Trp Cys Ile Ser Trp Ser Glu Ala Gln Arg Gln Ser Ile Tyr
        195                 200                 205

Ser Asp Pro Asn Tyr Leu Asp Gly Tyr Tyr Pro Val Glu Glu Gln Pro
    210                 215                 220

Val Ala Gly Leu Ser Ala Ala Arg Met Ser Ala Leu Leu Thr Tyr Arg
225                 230                 235                 240
```

| | | | | | | | | | | | |
|---|---|---|---|---|---|---|---|---|---|---|---|
|Thr|Arg|Asn|Ser|Phe|Glu|Asn|Lys|Phe|Ser|Arg|Ser|Pro|Ser|Ile|
| | |245| | | |250| | | |255| |

Thr Arg Asn Ser Phe Glu Asn Lys Phe Ser Arg Ser Pro Ser Ile
          245                 250                 255

Ala Gln Gln Lys Ala Gln Arg Glu Thr Arg Lys Pro Ser Thr
      260                 265                 270

Val Ser Glu His Ser Leu Gln Ile His Asn Asp Gly Tyr Lys Thr Lys
          275                 280                 285

Ala Ser Thr Ala Ile Ala Gly Ile Ser Gly Gln Lys Gly Gln Ser Val
      290                 295                 300

Val Ser Thr Ala Ser Ser Ser Asp Ser Leu Asn Ser Ser Thr Ser Met
305                 310                 315                 320

Thr Ser Val Ser Ser Val Thr Gly Glu Val Lys Asp Ile Lys Pro Ala
              325                 330                 335

Gln Thr Tyr Phe Ser Ala Gln Ser Tyr Leu Arg Tyr Gln Gly Thr Lys
              340                 345                 350

Phe Ile Asn Arg Phe Asp Ala Asn Cys Tyr Ile Ala Ile Thr Arg Lys
              355                 360                 365

Leu Asp Thr His Asp Leu Ala Arg Asp Arg Val Asp Asp Ile Thr Glu
      370                 375                 380

Val Leu Ser Thr Ile Gln Gln Pro Ser Leu Ile Ile Gly Ile Gln Ser
385                 390                 395                 400

Asp Gly Leu Phe Thr Tyr Ser Glu Gln Glu Phe Leu Ala Glu His Ile
              405                 410                 415

Pro Lys Ser Gln Leu Glu Lys Ile Glu Ser Pro Glu Gly His Asp Ala
              420                 425                 430

Phe Leu Leu Glu Phe Lys Leu Ile Asn Lys Leu Ile Val Gln Phe Leu
              435                 440                 445

Lys Thr Asn Cys Lys Ala Ile Thr Asp Ala Ala Pro Arg Ala Trp Gly
      450                 455                 460

Gly Asp Val Gly Asn Asp Glu Thr Lys Thr Ser Val Phe Gly Glu Ala
465                 470                 475                 480

Glu Glu Val Thr Asn Trp
              485

```
<210> SEQ ID NO 20
<211> LENGTH: 1335
<212> TYPE: DNA
<213> ORGANISM: Saccharomyces cerevisiae
<220> FEATURE:
<223> OTHER INFORMATION: HOMOCYSTEINE/CYSTEINE SYNTHASE (MET17)
<220> FEATURE:
<223> OTHER INFORMATION: HOMOCYSTEINE/CYSTEINE SYNTHASE (MET17)

<400> SEQUENCE: 20
atgccatctc atttcgatac tgttcaacta cacgccggcc aagagaaccc tggtgacaat       60
gctcacagat ccagagctgt accaatttac gccaccactt cttatgtttt cgaaaactct      120
aagcatggtt cgcaattgtt tggtctagaa gttccaggtt acgtctattc ccgtttccaa      180
aacccaacca gtaatgtttt ggaagaaaga attgctgctt agaaggtgg tgctgctgct      240 ttggctgttt cctccggtca agccgctcaa acccttgcca tccaaggttt ggcacacact      300
ggtgacaaca tcgtttccac ttcttactta tacggtggta cttataacca gttcaaaatc      360
tcgttcaaaa gatttggtat cgaggctaga tttgttgaag gtgacaatcc agaagaattc      420
gaaaaggtct ttgatgaaag aaccaaggct gtttatttgg aaaccattgg taatccaaag      480
tacaatgttc cggattttga aaaaattgtt gcaattgctc acaaacacgg tattccagtt      540
gtcgttgaca cacatttggg tgccggtggt tacttctgtc agccaattaa atacggtgct      600
```

```
gatattgtaa cacattctgc taccaaatgg attggtggtc atggtactac tatcggtggt    660
attattgttg actctggtaa gttcccatgg aaggactacc cagaaaagtt ccctcaattc    720
tctcaacctg ccgaaggata tcacggtact atctacaatg aagcctacgg taacttggca    780
tacatcgttc atgttagaac tgaactatta agagatttgg gtccattgat gaacccattt    840
gcctctttct tgctactaca aggtgttgaa acattatctt tgagagctga aagacacggt    900
gaaaatgcat gaagttagc caaatggtta gaacaatccc catacgtatc ttgggtttca    960 tacccctggtt tagcatctca ttctcatcat gaaaatgcta agaagtatct atctaacggt   1020 ttcggtggt tcttatcttt cggtgtaaaa gacttaccaa atgccgacaa ggaaactgac   1080
ccattcaaac tttctggtgc tcaagttgtt gacaatttaa agcttgcctc taacttggcc   1140
aatgttggtg atgccaagac cttagtcatt gctccatact tcactaccca caaacaatta   1200
aatgacaaag aaaagttggc atctggtgtt accaaggact taattcgtgt ctctgttggt   1260
atcgaattta ttgatgacat tattgcagac ttccagcaat cttttgaaac tgttttcgct   1320
ggccaaaaac catga                                                    1335
```

```
<210> SEQ ID NO 21
<211> LENGTH: 444
<212> TYPE: PRT
<213> ORGANISM: Saccharomyces cerevisiae
<220> FEATURE:
<223> OTHER INFORMATION: HOMOCYSTEINE/CYSTEINE SYNTHASE (MET17)
<220> FEATURE:
<223> OTHER INFORMATION: HOMOCYSTEINE/CYSTEINE SYNTHASE (MET17)

<400> SEQUENCE: 21
```

Met Pro Ser His Phe Asp Thr Val Gln Leu His Ala Gly Gln Glu Asn
1               5                   10                  15

Pro Gly Asp Asn Ala His Arg Ser Arg Ala Val Pro Ile Tyr Ala Thr
            20                  25                  30

Thr Ser Tyr Val Phe Glu Asn Ser Lys His Gly Ser Gln Leu Phe Gly
        35                  40                  45

Leu Glu Val Pro Gly Tyr Val Tyr Ser Arg Phe Gln Asn Pro Thr Ser
50                  55                  60

Asn Val Leu Glu Glu Arg Ile Ala Ala Leu Glu Gly Ala Ala Ala
65                  70                  75                  80

Leu Ala Val Ser Ser Gly Gln Ala Ala Gln Thr Leu Ala Ile Gln Gly
                85                  90                  95

Leu Ala His Thr Gly Asp Asn Ile Val Ser Thr Ser Tyr Leu Tyr Gly
            100                 105                 110

Gly Thr Tyr Asn Gln Phe Lys Ile Ser Phe Lys Arg Phe Gly Ile Glu
        115                 120                 125

Ala Arg Phe Val Glu Gly Asp Asn Pro Glu Glu Phe Glu Lys Val Phe
    130                 135                 140

Asp Glu Arg Thr Lys Ala Val Tyr Leu Glu Thr Ile Gly Asn Pro Lys
145                 150                 155                 160

Tyr Asn Val Pro Asp Phe Glu Lys Ile Val Ala Ile Ala His Lys His
                165                 170                 175

Gly Ile Pro Val Val Asp Asn Thr Phe Gly Ala Gly Gly Tyr Phe
            180                 185                 190

Cys Gln Pro Ile Lys Tyr Gly Ala Asp Ile Val Thr His Ser Ala Thr
        195                 200                 205

Lys Trp Ile Gly Gly His Gly Thr Thr Ile Gly Gly Ile Ile Val Asp

```
Ser Gly Lys Phe Pro Trp Lys Asp Tyr Pro Glu Lys Phe Pro Gln Phe
225                 230                 235                 240

Ser Gln Pro Ala Glu Gly Tyr His Gly Thr Ile Tyr Asn Glu Ala Tyr
            245                 250                 255

Gly Asn Leu Ala Tyr Ile Val His Val Arg Thr Glu Leu Leu Arg Asp
        260                 265                 270

Leu Gly Pro Leu Met Asn Pro Phe Ala Ser Phe Leu Leu Leu Gln Gly
    275                 280                 285

Val Glu Thr Leu Ser Leu Arg Ala Glu Arg His Gly Glu Asn Ala Leu
290                 295                 300

Lys Leu Ala Lys Trp Leu Glu Gln Ser Pro Tyr Val Ser Trp Val Ser
305                 310                 315                 320

Tyr Pro Gly Leu Ala Ser His Ser His His Glu Asn Ala Lys Lys Tyr
            325                 330                 335

Leu Ser Asn Gly Phe Gly Gly Val Leu Ser Phe Gly Val Lys Asp Leu
        340                 345                 350

Pro Asn Ala Asp Lys Glu Thr Asp Pro Phe Lys Leu Ser Gly Ala Gln
    355                 360                 365

Val Val Asp Asn Leu Lys Leu Ala Ser Asn Leu Ala Asn Val Gly Asp
370                 375                 380

Ala Lys Thr Leu Val Ile Ala Pro Tyr Phe Thr Thr His Lys Gln Leu
385                 390                 395                 400

Asn Asp Lys Glu Lys Leu Ala Ser Gly Val Thr Lys Asp Leu Ile Arg
            405                 410                 415

Val Ser Val Gly Ile Glu Phe Ile Asp Asp Ile Ile Ala Asp Phe Gln
        420                 425                 430

Gln Ser Phe Glu Thr Val Phe Ala Gly Gln Lys Pro
    435                 440

<210> SEQ ID NO 22
<211> LENGTH: 554
<212> TYPE: DNA
<213> ORGANISM: Saccharomyces cerevisiae
<220> FEATURE:
<223> OTHER INFORMATION: pTDH3
<220> FEATURE:
<223> OTHER INFORMATION: pTDH3

<400> SEQUENCE: 22
ccaaaatagg gggcgggtta cacagaatat ataacatcgt aggtgtctgg gtgaacagtt      60
tattcctggc atccactaaa tataatggag cccgcttttt aagctggcat ccagaaaaaa     120
aaagaatccc agcaccaaaa tattgttttc ttcaccaacc atcagttcat aggtccattc     180
tcttagcgca actacagaga acaggggcac aaacaggcaa aaacgggca caacctcaat      240 ggagtgatgc aacctgcctg gagtaaatga tgacacaagg caattgaccc acgcatgtat     300
ctatctcatt ttcttacacc ttctattacc ttctgctctc tctgatttgg aaaaagctga     360
aaaaaaaggt tgaaaccagt tccctgaaat tattccccta cttgactaat aagtatataa     420
agacggtagg tattgattgt aattctgtaa atctatttct taaacttctt aaattctact     480
tttatagtta gtcttttttt tagttttaaa acaccaagaa cttagtttcg aataaacaca     540
cataaacaaa caaa                                                        554

<210> SEQ ID NO 23
<211> LENGTH: 550
```

```
<212> TYPE: DNA
<213> ORGANISM: Saccharomyces cerevisiae
<220> FEATURE:
<223> OTHER INFORMATION: pENO2
<220> FEATURE:
<223> OTHER INFORMATION: pENO2

<400> SEQUENCE: 23
cgctcagcat ctgcttcttc ccaaagatga acgcggcgtt atgtcactaa cgacgtgcac    60
caacttgcgg aaagtggaat cccgttccaa aactggcatc cactaattga tacatctaca   120
caccgcacgc cttttttctg aagcccactt tcgtggactt tgccatatgc aaaattcatg   180
aagtgtgata ccaagtcagc atacacctca ctagggtagt ttctttggtt gtattgatca   240
tttggttcat cgtggttcat taattttttt tctccattgc tttctggctt tgatcttact   300
atcatttgga tttttgtcga aggttgtaga attgtatgtg acaagtggca ccaagcatat   360
ataaaaaaaa aaagcattat cttcctacca gagttgattg ttaaaaacgt atttatagca   420
aacgcaattg taattaattc ttattttgta tcttttcttc ccttgtctca atctttttatt  480 tttattttat ttttcttttc ttagtttctt tcataacacc aagcaactaa tactataaca   540
tacaataata                                                          550

<210> SEQ ID NO 24
<211> LENGTH: 419
<212> TYPE: DNA
<213> ORGANISM: Saccharomyces cerevisiae
<220> FEATURE:
<223> OTHER INFORMATION: pTEF Kl
<220> FEATURE:
<223> OTHER INFORMATION: pTEF Kl

<400> SEQUENCE: 24
ctctctcgca ataacaatga acactgggtc aatcatagcc tacacaggtg aacagagtag    60
cgtttataca gggtttatac ggtgattcct acggcaaaaa ttttcattt ctaaaaaaaa    120 aaagaaaaat ttttctttcc aacgctagaa ggaaaagaaa aatctaatta aattgatttg   180
gtgattttct gagagttccc ttttcatat atcgaatttt gaatataaaa ggagatcgaa    240
aaaatttttc tattcaatct gttttctggt tttatttgat agttttttttg tgtattatta   300 ttatggatta gtactggttt atatgggttt ttctgtataa cttcttttta ttttagtttg   360
tttaatctta ttttgagtta cattatagtt ccctaactgc aagagaagta acattaaaa   419

<210> SEQ ID NO 25
<211> LENGTH: 598
<212> TYPE: DNA
<213> ORGANISM: Saccharomyces cerevisiae
<220> FEATURE:
<223> OTHER INFORMATION: pTEF3
<220> FEATURE:
<223> OTHER INFORMATION: pTEF3

<400> SEQUENCE: 25
ggctgataat agcgtataaa caatgcatac tttgtacgtt caaaatacaa tgcagtagat    60
atatttatgc atattacata taatacatat cacataggaa gcaacaggcg cgttggactt   120
ttaattttcg aggaccgcga atccttacat cacacccaat cccccacaag tgatccccca   180
cacaccatag cttcaaaatg tttctactcc ttttttactc ttccagattt tctcggactc   240
cgcgcatcgc cgtaccactt caaaacaccc aagcacagca tactaaattt ccctctcttc   300
ttcctctagg gtgtcgttaa ttacccgtac taaaggtttg gaaaagaaaa aagagaccgc   360
```

```
ctcgtttctt tttcttcgtc gaaaaaggca ataaaaattt ttatcacgtt tctttttctt    420
gaaaattttt ttttttgatt tttttctctt tcgatgacct cccattgata tttaagttaa    480
taaacggtct tcaatttctc aagtttcagt ttcattttc ttgttctatt acaactttt     540 ttacttcttg ctcattagaa agaaagcata gcaatctaat ctaagtttta attacaaa     598
```

<210> SEQ ID NO 26
<211> LENGTH: 383
<212> TYPE: DNA
<213> ORGANISM: Saccharomyces cerevisiae
<220> FEATURE:
<223> OTHER INFORMATION: pTEF1
<220> FEATURE:
<223> OTHER INFORMATION: pTEF1

<400> SEQUENCE: 26

```
gtttagcttg cctcgtcccc gccgggtcac ccggccagcg acatggaggc ccagaatacc     60
ctccttgaca gtcttgacgt gcgcagctca ggggcatgat gtgactgtcg cccgtacatt    120
tagcccatac atccccatgt ataatcattt gcatccatac attttgatgg ccgcacggcg    180
cgaagcaaaa attacggctc ctcgctgcag acctgcgagc agggaaacgc tcccctcaca    240
gacgcgttga attgtcccca cgccgcgccc ctgtagagaa atataaaagg ttaggatttg    300
ccactgaggt tcttctttca tatacttcct tttaaaatct tgctacgata cagttctcac    360
atcacatccg aacataaaca acc                                           383
```

<210> SEQ ID NO 27
<211> LENGTH: 700
<212> TYPE: DNA
<213> ORGANISM: Saccharomyces cerevisiae
<220> FEATURE:
<223> OTHER INFORMATION: pADH1
<220> FEATURE:
<223> OTHER INFORMATION: pADH1

<400> SEQUENCE: 27

```
gggtgtacaa tatggacttc ctcttttctg gcaaccaaac ccatacatcg ggattcctat     60
aataccttcg ttggtctccc taacatgtag gtggcggagg ggagatatac aatagaacag    120
ataccagaca agacataatg ggctaaacaa gactacacca attacactgc ctcattgatg    180
gtggtacata cgaactaat actgtagccc tagacttgat agccatcatc atatcgaagt     240
ttcactaccc ttttccatt tgccatctat tgaagtaata ataggcgcat gcaacttctt    300
ttcttttttt ttcttttctc tctccccgt tgttgtctca ccatatccgc aatgacaaaa    360
aaatgatgga agacactaaa ggaaaaaatt aacgacaaag acagcaccaa cagatgtcgt    420
tgttccagag ctgatgaggg gtatctcgaa gcacacgaaa cttttttcctt ccttcattca    480 cgcacactac tctctaatga gcaacggtat acggccttcc ttccagttac ttgaatttga    540
aataaaaaaa agtttgctgt cttgctatca agtataaata gacctgcaat tattaatctt    600
ttgtttcctc gtcattgttc tcgttccctt tcttccttgt ttcttttttct gcacaatatt    660 tcaagctata ccaagcatac aatcaactat ctcatataca                         700
```

<210> SEQ ID NO 28
<211> LENGTH: 549
<212> TYPE: DNA
<213> ORGANISM: Saccharomyces cerevisiae
<220> FEATURE:
<223> OTHER INFORMATION: pGPM 1
<220> FEATURE:
<223> OTHER INFORMATION: pGPM 1

<400> SEQUENCE: 28

```
gccaaacttt tcggttaaca catgcagtga tgcacgcgcg atggtgctaa gttacatata    60
tatatatata tatatatata tatatatata gccatagtga tgtctaagta acctttatgg   120
tatatttctt aatgtggaaa gatactagcg cgcgcaccca cacacaagct tcgtcttttc   180
ttgaagaaaa gaggaagctc gctaaatggg attccacttt ccgttccctg ccagctgatg   240
gaaaaaggtt agtggaacga tgaagaataa aagagagat ccactgaggt gaaatttcag    300
ctgacagcga gtttcatgat cgtgatgaac aatggtaacg agttgtggct gttgccaggg   360
agggtggttc tcaacttta atgtatggcc aaatcgctac ttgggtttgt tatataacaa    420
agaagaaata atgaactgat tctcttcctc cttcttgtcc tttcttaatt ctgttgtaat   480
taccttcctt tgtaattttt tttgtaatta ttcttcttaa taatccaaac aaacacacat   540
attacaata                                                           549
```

<210> SEQ ID NO 29
<211> LENGTH: 650
<212> TYPE: DNA
<213> ORGANISM: Saccharomyces cerevisiae
<220> FEATURE:
<223> OTHER INFORMATION: pFBA1
<220> FEATURE:
<223> OTHER INFORMATION: pFBA1

<400> SEQUENCE: 29

```
acgcaagccc taagaaatga ataacaatac tgacagtact aaataattgc ctacttggct    60
tcacatacgt tgcatacgtc gatatagata ataatgataa tgacagcagg attatcgtaa   120
tacgtaatag ttgaaaatct caaaaatgtg tgggtcatta cgtaaataat gataggaatg   180
ggattcttct atttttcctt tttccattct agcagccgtc gggaaaacgt ggcatcctct   240
ctttcgggct caattggagt cacgctgccg tgagcatcct ctctttccat atctaacaac   300
tgagcacgta accaatggaa aagcatgagc ttagcgttgc tccaaaaaag tattggatgg   360
ttaataccat ttgtctgttc tcttctgact ttgactcctc aaaaaaaaaa aatctacaat   420
caacagatcg cttcaattac gccctcacaa aaactttttt ccttcttctt cgcccacgtt   480
aaatttatc cctcatgttg tctaacggat ttctgcactt gatttattat aaaaagacaa    540
agacataata cttctctatc aatttcagtt attgttcttc cttgcgttat tcttctgttc   600
ttcttttct tttgtcatat ataaccataa ccaagtaata catattcaaa                650
```

<210> SEQ ID NO 30
<211> LENGTH: 700
<212> TYPE: DNA
<213> ORGANISM: Saccharomyces cerevisiae
<220> FEATURE:
<223> OTHER INFORMATION: pPDC1
<220> FEATURE:
<223> OTHER INFORMATION: pPDC1

<400> SEQUENCE: 30

```
ttatttacct atctctaaac ttcaacacct tatatcataa ctaatatttc ttgagataag    60
cacactgcac ccataccttc cttaaaaacg tagcttccag ttttggtgg ttccggcttc    120
cttcccgatt ccgcccgcta aacgcatatt tttgttgcct ggtggcattt gcaaaatgca   180
taacctatgc atttaaaaga ttatgtatgc tcttctgact tttcgtgtga tgaggctcgt   240
ggaaaaaatg aataatttat gaatttgaga acaatttgt gttgttacgg tattttacta   300
```

```
tggaataatc aatcaattga ggattttatg caaatatcgt ttgaatattt ttccgaccct    360
ttgagtactt ttcttcataa ttgcataata ttgtccgctg ccccttttc tgttagacgg     420 tgtcttgatc tacttgctat cgttcaacac caccttattt tctaactatt tttttttag    480 ctcatttgaa tcagcttatg gtgatggcac attttgcat aaacctagct gtcctcgttg    540
aacataggaa aaaaaatat ataaacaagg ctctttcact ctccttgcaa tcagatttgg     600
gtttgttccc tttatttca tatttcttgt catattcctt tctcaattat tattttctac    660
tcataacctc acgcaaaata acacagtcaa atcaatcaaa                          700

<210> SEQ ID NO 31
<211> LENGTH: 998
<212> TYPE: DNA
<213> ORGANISM: Saccharomyces cerevisiae
<220> FEATURE:
<223> OTHER INFORMATION: pCCW12
<220> FEATURE:
<223> OTHER INFORMATION: pCCW12

<400> SEQUENCE: 31
aaccagggca aagcaaaata aaagaaactt aatacgttat gccgtaatga agggctacca    60
aaaacgataa tctcaactgt aaacaggtac aatgcggacc ttttgccac aaaacataca    120 tcattcattg ccggaaaaag aaagaagtga agacagcagt gcagccagcc atgttgcgcc    180
aatctaatta tagatgctgg tgccctgagg atgtatctgg agccagccat ggcatcatgc    240
gctaccgccg gatgtaaaat ccgacacgca aagaaaacc ttcgaggttg cgcacttcgc    300
ccacccatga accacacggt tagtccaaaa ggggcagttc agattccaga tgcgggaatt    360
agcttgctgc caccctcacc tcactaacgc tgcggtgtgc ggatacttca tgctatttat    420
agacgcgcgt gtcggaatca gcacgcgcaa gaaccaaatg ggaaaatcgg aatgggtcca    480
gaactgcttt gagtgctggc tattggcgtc tgatttccgt tttgggaatc ctttgccgcg    540
cgcccctctc aaaactccgc acaagtccca gaaagcggga agaaataaa acgccaccaa    600 aaaaaaaaat aaaagccaat cctcgaagcg tgggtggtag gccctggatt atcccgtaca    660
agtatttctc aggagtaaaa aaaccgtttg ttttggaatt ccccatttcg cggccaccta    720
cgccgctatc tttgcaacaa ctatctgcga taactcagca aattttgcat attcgtgttg    780
cagtattgcg ataatgggag tcttacttcc aacataacgg cagaaagaaa tgtgagaaaa    840
ttttgcatcc tttgcctccg ttcaagtata taagtcggc atgcttgata atctttcttt    900
ccatcctaca ttgttctaat tattcttatt ctcctttatt ctttcctaac ataccaagaa    960
attaatcttc tgtcattcgc ttaaacacta tatcaata                            998

<210> SEQ ID NO 32
<211> LENGTH: 700
<212> TYPE: DNA
<213> ORGANISM: Saccharomyces cerevisiae
<220> FEATURE:
<223> OTHER INFORMATION: pGK1
<220> FEATURE:
<223> OTHER INFORMATION: pGK1

<400> SEQUENCE: 32
gtgagtaagg aaagagtgag gaactatcgc atacctgcat ttaaagatgc cgatttgggc    60
gcgaatcctt tattttggct tcaccctcat actattatca gggccagaaa aaggaagtgt    120
ttccctcctt cttgaattga tgttaccctc ataaagcacg tggcctctta tcgagaagaa    180
aattaccgtc gctcgtgatt tgtttgcaaa aagaacaaaa ctgaaaaaac ccagacacgc    240
```

```
tcgacttcct gtcttcctat tgattgcagc ttccaatttc gtcacacaac aaggtcctag    300
cgacggctca caggttttgt aacaagcaat cgaaggttct ggaatggcgg gaaagggttt    360
agtaccacat gctatgatgc ccactgtgat ctccagagca aagttcgttc gatcgtactg    420
ttactctctc tctttcaaac agaattgtcc gaatcgtgtg acaacaacag cctgttctca    480
cacactcttt tcttctaacc aagggggtgg tttagtttag tagaacctcg tgaaacttac    540
atttacatat atataaactt gcataaattg gtcaatgcaa gaaatacata tttggtcttt    600
tctaattcgt agttttttcaa gttcttagat gctttctttt tctctttttt acagatcatc   660
aaggaagtaa ttatctactt tttacaacaa atataaaaca                          700

<210> SEQ ID NO 33
<211> LENGTH: 913
<212> TYPE: DNA
<213> ORGANISM: Saccharomyces cerevisiae
<220> FEATURE:
<223> OTHER INFORMATION: pMDH2
<220> FEATURE:
<223> OTHER INFORMATION: pMDH2

<400> SEQUENCE: 33
ccttcgctaa ataataaacc tgaactgtac ttagcgaagc cttcatagca cctacgtaca     60
cgtatatata gacattttac gtaatggaga aactgaggtt tttgttttca cttttttttct  120 ttctttttca ctattgctcg aaccgcctgc gatgagctaa gaaaaaaaag tgaaagaaat   180
catagaaagc aaaaatgaga ttatatagcc cagagccctc ttctggcgcc tgtcccaagg   240
cggaccaaca acaacacttg cccaaaccta agaaaatccc ctcatacttt tccgtttgta   300
tctcctactt tcttacttcc ttttttttctt ctttatttgc ttggtttacc attgaagtcc   360 attttttacta cagacaatag ctagtcattc gctatcttcc gtttgtcact ttttttcaaa   420
tttctcatct atatagcgaa gtacggaaaa gatgtcactt gccggcatct cggccttccc    480
cggccaaatg gactcatcat ctacgatacg gccccttttaa tccgcaatta ctttgcccat   540
tcggccgtag ccgttctaaa gccgcgtgc cttgccccca atactcccct aatgatccgg    600
gaagttccgg ttttttttcct tgtttagtg gcatttttgtg ttgcccaagg ttgggaaggt   660
ccgatttgac tttaaggaac tacggaaggt atctaaggtt tctaaaaaca atatacacgc    720
gcgtgcgtag atatataaag ataaagattt atcgatatga gataaagatt gctgcatgat    780
tctccttctg attctttttc cctgtatata ttttctcccc ttctgtataa atcgtacagt    840
cagaagtagt ccagaatata gtgctgcaga ctattacaaa agttcaatac aatatcataa    900
aagttatagt aac                                                       913

<210> SEQ ID NO 34
<211> LENGTH: 406
<212> TYPE: DNA
<213> ORGANISM: Saccharomyces cerevisiae
<220> FEATURE:
<223> OTHER INFORMATION: pURA3
<220> FEATURE:
<223> OTHER INFORMATION: pURA3

<400> SEQUENCE: 34
ggtacccaaa ccgaagttat ctgatgtaga aaaggattaa agatgctaag agatagtgat     60
gatatttcat aaataatgta attctatata tgttaattac cttttttgcg aggcatattt    120
atggtgaagg ataagttttg accatcaaag aaggttaatg tggctgtggt ttcagggtcc    180
```

```
ataaagcttt tcaattcatc ttttttttt ttgttctttt ttttgattcc ggtttctttg    240
aaattttttt gattcggtaa tctccgagca gaaggaagaa cgaaggaagg agcacagact    300
tagattggta tatatacgca tatgtggtgt tgaagaaaca tgaaattgcc cagtattctt    360
aacccaactg cacagaacaa aaacctgcag gaaacgaaga taaatc                   406

<210> SEQ ID NO 35
<211> LENGTH: 535
<212> TYPE: DNA
<213> ORGANISM: Saccharomyces cerevisiae
<220> FEATURE:
<223> OTHER INFORMATION: pRPLA1
<220> FEATURE:
<223> OTHER INFORMATION: pRPLA1

<400> SEQUENCE: 35
tcaagttgga tactgatctg atctctccgc cctactacca gggaccctca tgattaccgc     60
tcgaatgcga cgtttcctgc ctcataaaac tggcttgaaa atatttattc gctgaacagt    120
agcctagctt ataaaaattt catttaatta atgtaatatg aaaactcaca tgccttctgt    180
ttctaaaatt gtcacagcaa gaaataacat taccatacgt gatcttatta aactctagta    240
tcttgtctaa tacttcattt aaaagaagcc ttaaccctgt agcctcatct atgtctgcta    300
catatcgtga ggtacgaata tcgtaagatg ataccacgca actttgtaat gattttttt     360 tttcattt ttaaagaatg cctttacatg gtatttgaaa aaaatatctt tataaagttt      420
gcgatctctt ctgttctgaa taattttttag taaagaaat caaaagaata agaaatagt     480 ccgctttgtc caatacaaca gcttaaaccg attatctcta aaataacaag aagaa          535

<210> SEQ ID NO 36
<211> LENGTH: 400
<212> TYPE: DNA
<213> ORGANISM: Saccharomyces cerevisiae
<220> FEATURE:
<223> OTHER INFORMATION: pSAM4
<220> FEATURE:
<223> OTHER INFORMATION: pSAM4

<400> SEQUENCE: 36
agattttggt gttagatggt actcttgcat atgtaacctt taataaattt tgcaaatcga     60
attcctttgt aacgtgcaaa gcattttata gcctggcgct cgcattgtta agcaacaggc    120
ggtgcggcaa cgttgaaatg tttcacgcag gttttttac gtactgcacg gcattctgga    180
gtgaaaaaaa atgaaaagta cagctcgaag tttttttgtcc atcggttgta ctttgcagag   240
tattagtcat ttttgatatc agagtactac tatcgaagca ttttttacgct tgaataactt   300 gaatattatt gaaagcttag ttcaaccaag ctgaaaagaa ccattattca acataattgg    360
aaatcatttc gttactaaat cgtccgaaaa ttgcagaaaa                          400

<210> SEQ ID NO 37
<211> LENGTH: 505
<212> TYPE: DNA
<213> ORGANISM: Saccharomyces cerevisiae
<220> FEATURE:
<223> OTHER INFORMATION: pCUP1-1
<220> FEATURE:
<223> OTHER INFORMATION: pCUP1-1

<400> SEQUENCE: 37
cggcaaactt caacgatttc tatgatgcat tttataatta gtaagccgat cccattaccg     60
acatttgggc gctatacgtg catatgttca tgtatgtatc tgtatttaaa acacttttgt    120
```

```
attattttc ctcatatatg tgtataggtt tatacggatg atttaattat tacttcacca    180 cccttttattt caggctgata tcttagcctt gttactagtg agaaaaagac attttttgctg   240 tcagtcactg tcaagagatt cttttgctgg catttcttcc agaagcaaaa agagcgatgc   300
gtcttttccg ctgaaccgtt ccagcaaaaa agactaccaa cgcaatatgg attgtcagaa   360
tcatataaaa gagaagcaaa taactccttg tcttgtatca attgcattat aatatcttct   420
tgttagtgca atatcatata gaagtcatcg aaatagatat aagaaaaac aaactgtaca   480 atcaatcaat caatcatcac ataaa                                        505
```

<210> SEQ ID NO 38
<211> LENGTH: 500
<212> TYPE: DNA
<213> ORGANISM: Candida glabrata
<220> FEATURE:
<223> OTHER INFORMATION: pCUP1.Cgla
<220> FEATURE:
<223> OTHER INFORMATION: pCUP1.Cgla

<400> SEQUENCE: 38

```
cacaccacac aaccgtcagc accccggctg tacgtctgtg aaggctgcgg tatagacacg    60
gactgcgata cagaactcat gacttatatc tgtagactcc tctgcttcaa tgcgaactcc   120
aggatcaccg aatagcatgc gatgagctgt tgattcttat atataattat ctattgcatt   180 tttttttaa tgctgcatgg gggggcctag taaatcaccc gtacaagtca cgcgtgagag   240
aaagagaagg gcccttcgt cgtggaagcg tggatcgtga gcgacctgtt tctaaatata   300
gcttttgggt aggatattat attaagtgaa attttattag agggtaaatg tatgtgaaag   360
ttatgtataa tatgttgcta aattagcgat cgtgaatgca tagaatctaa tcgttataga   420
aaaccgcaac ttgtgctgtt ttgttgtgtt ttcttgtcgt tttttatat tatttatcta   480 gtattttgct ttagttgtta                                               500
```

<210> SEQ ID NO 39
<211> LENGTH: 425
<212> TYPE: DNA
<213> ORGANISM: Saccharomyces bayanus
<220> FEATURE:
<223> OTHER INFORMATION: pCUP1.Sba
<220> FEATURE:
<223> OTHER INFORMATION: pCUP1.Sba

<400> SEQUENCE: 39

```
agaaggagg gtcctattac caatacttgg acgctatacg tgcatatgta catgtacgta    60
tctgtattta aacacttttg tattattttc tttatatatg tgtataggtt tacatggttg   120
acttttatca ttgtttgtgc acatttgcaa tggccatttt tttgttttg agaaaggtat   180 tattgctgtc actattcgag atgcttttgc tgacattcct cctagaagcc aaaaggccga   240 tgcgttttt ccgctgagag gataccagca aaaaagcta ccagtacaag atgggacggc   300
aaaagcgtat aaaagaagaa gcaaaatgac cagatatgct ttcaatttca tcaatgtttc   360
tttctccctg ttatgatcca gaagaataat caaaagcaaa acatctattc aatcaatctc   420
ataaa                                                               425
```

<210> SEQ ID NO 40
<211> LENGTH: 741
<212> TYPE: DNA
<213> ORGANISM: Artificial Sequence
<220> FEATURE:

<223> OTHER INFORMATION: pACU1
<220> FEATURE:
<223> OTHER INFORMATION: pACU1

<400> SEQUENCE: 40

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg atttttattc caacactaag aaataaattc gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tcgaaaaaga cattttttgct gtcagtcact gtcaagagat tcttttgctg catttcttc    420
cagaagcaaa aagagcgatg cgtcttttcc gctgaaccgt tccagcaaaa aagactacca     480
acgaattcta attaagttag tcaaggcgcc atcctcatga aaactgtgta acataataac     540
cgaagtgtcg aaaaggtggc accttgtcca attgaacacg ctcgatgaaa aaataagat     600
atatataagg ttaagtaaag cgtctgttag aaaggaagtt tttcctttt cttgctctct     660
tgtcttttca tctactattt ccttcgtgta atacagggtc gtcagataca tagatacaat     720
tctattaccc ccatccatac a                                              741
```

<210> SEQ ID NO 41
<211> LENGTH: 757
<212> TYPE: DNA
<213> ORGANISM: Artificial Sequence
<220> FEATURE:
<223> OTHER INFORMATION: pACU2
<220> FEATURE:
<223> OTHER INFORMATION: pACU2

<400> SEQUENCE: 41

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg atttttattc caacactaag aaataaattc gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccgaatt cgaaaaagac attttttgctg tcagtcactg    360
tcaagagatt cttttgctgg catttcttcc agaagcaaaa agagcgatgc gtcttttccg     420
ctgaaccgtt ccagcaaaaa agactaccaa cgaattccac gtgaagctgt cgatattggg     480
gaactgtggt ggttggcaaa tgactaatta agttagtcaa ggcgccatcc tcatgaaaac     540
tgtgtaacat aataaccgaa gtgtcgaaaa ggtggcacct tgtccaattg aacacgctcg     600
atgaaaaaaa taagatatat ataaggttaa gtaaagcgtc tgttagaaag gaagttttc    660
ctttttcttg ctctcttgtc ttttcatcta ctatttcctt cgtgtaatac agggtcgtca     720
gatacataga tacaattcta ttaccccat ccataca                              757
```

<210> SEQ ID NO 42
<211> LENGTH: 498
<212> TYPE: DNA
<213> ORGANISM: Artificial Sequence
<220> FEATURE:
<223> OTHER INFORMATION: pACU3p
<220> FEATURE:
<223> OTHER INFORMATION: pACU3p

<400> SEQUENCE: 42

```
ttatattgaa ttttcaaaaa ttcttacttt tttttttggat ggacgcaaag aagtttaata    60
atcatattac atggcattac caccatatac atatccatat ctaatcttac ttatatgttg   120
tggaaatgta aagagcccga attcgaaaaa gacattttttg ctgtcagtca ctgtcaagag   180
attcttttgc tggcatttct tccagaagca aaaagagcga tgcgtctttt ccgctgaacc   240
gttccagcaa aaagactac caacgaattc ggatgataat gcgattagtt ttttagcctt   300
atttctgggg taattaatca gcgaagcgat gattttttgat ctattaacag atatataaat   360
ggaaaagctg cataaccact ttaactaata ctttcaacat tttcagtttg tattacttct   420
tattcaaatg tcataaaagt atcaacaaaa aattgttaat atacctctat actttaacgt   480
caaggagaaa aaactata                                                  498
```

<210> SEQ ID NO 43
<211> LENGTH: 498
<212> TYPE: DNA
<213> ORGANISM: Artificial Sequence
<220> FEATURE:
<223> OTHER INFORMATION: pACU4p
<220> FEATURE:
<223> OTHER INFORMATION: pACU4p

<400> SEQUENCE: 43

```
ttatattgaa ttttcaaaaa ttcttacttt tttttttggat ggacgcaaag aagtttaata    60
atcatattac atggcattac caccatatac atatccatat ctaatcttac ttatatgttg   120
tggaaatgta aagagcccga attcgttggt agtctttttt gctggaacgg ttcagcggaa   180
aagacgcatc gctcttttttg cttctggaag aaatgccagc aaaagaatct cttgacagtg   240
actgacagca aaaatgtctt tttcgaattc ggatgataat gcgattagtt ttttagcctt   300
atttctgggg taattaatca gcgaagcgat gattttttgat ctattaacag atatataaat   360
ggaaaagctg cataaccact ttaactaata ctttcaacat tttcagtttg tattacttct   420
tattcaaatg tcataaaagt atcaacaaaa aattgttaat atacctctat actttaacgt   480
caaggagaaa aaactata                                                  498
```

<210> SEQ ID NO 44
<211> LENGTH: 530
<212> TYPE: DNA
<213> ORGANISM: Artificial Sequence
<220> FEATURE:
<223> OTHER INFORMATION: pACU5
<220> FEATURE:
<223> OTHER INFORMATION: pACU5

<400> SEQUENCE: 44

```
ggaggacgaa acaaaaaagt gaaaaaaaat gaaaattttt ttggaaaacc aagaaatgaa    60
ttatatttcc gtgtgagacg acatcgtcga atatgattca gggtaacagt attgatgtaa   120
tcaatttcct acctgaatct aaaattcccg gaattcgaaa aagacatttt tgctgtcagt   180
cactgtcaag agattctttt gctggcattt cttccagaag caaaaagagc gatgcgtctt   240
ttccgctgaa ccgttccagc aaaaaagact accaacgaat tccagcagaa tccgccaggc   300
gtgtatatat agcgtggatg gccaggcaac tttagtgctg acacatacag gcatatatat   360
atgtgtgcga cgacacatga tcatatggca tgcatgtgct ctgtatgtat ataaaactct   420
tgtttttcttc ttttctctaa atattctttc cttatacatt aggacctttg cagcataaat   480
```
tactatactt ctatagacac acaaacacaa atacacacac taaattaata        530

<210> SEQ ID NO 45
<211> LENGTH: 867
<212> TYPE: DNA
<213> ORGANISM: Artificial Sequence
<220> FEATURE:
<223> OTHER INFORMATION: pACU6
<220> FEATURE:
<223> OTHER INFORMATION: pACU6

<400> SEQUENCE: 45
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg atttttattc caacactaag aaataatttc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tcgaaaaaga cattttttgct gtcagtcact gtcaagagat tcttttgctg gcatttcttc    420
cagaagcaaa aagagcgatg cgtcttttcc gctgaaccgt tccagcaaaa aagactacca    480
acgaattcga aaagacatt tttgctgtca gtcactgtca agagattctt ttgctggcat    540
ttcttccaga agcaaaaaga gcgatgcgtc ttttccgctg aaccgttcca gcaaaaaga    600 ctaccaacga attctaatta agttagtcaa ggcgccatcc tcatgaaaac tgtgtaacat    660
aataaccgaa gtgtcgaaaa ggtggcacct tgtccaattg aacacgctcg atgaaaaaaa    720
taagatatat ataaggttaa gtaaagcgtc tgttagaaag gaagtttttc cttttttcttg    780 ctctcttgtc ttttcatcta ctatttcctt cgtgtaatac agggtcgtca gatacataga    840
tacaattcta ttaccccccat ccataca                                      867

<210> SEQ ID NO 46
<211> LENGTH: 867
<212> TYPE: DNA
<213> ORGANISM: Artificial Sequence
<220> FEATURE:
<223> OTHER INFORMATION: pACU7
<220> FEATURE:
<223> OTHER INFORMATION: pACU7

<400> SEQUENCE: 46
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg atttttattc caacactaag aaataatttc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tcgttggtag tcttttttgc tggaacggtt cagcggaaaa gacgcatcgc tcttttttgct    420 tctggaagaa atgccagcaa aagaatctct tgacagtgac tgacagcaaa aatgtctttt    480
tcgaattcgt tggtagtctt ttttgctgga acggttcagc ggaaaagacg catcgctctt    540
tttgcttctg gaagaaatgc cagcaaaaga atctcttgac agtgactgac agcaaaaatg    600 tcttttttcga attctaatta agttagtcaa ggcgccatcc tcatgaaaac tgtgtaacat    660
aataaccgaa gtgtcgaaaa ggtggcacct tgtccaattg aacacgctcg atgaaaaaaa    720

| taagatatat ataaggttaa gtaaagcgtc tgttagaaag gaagtttttc cttttttcttg | 780 |
| ctctcttgtc ttttcatcta ctatttcctt cgtgtaatac agggtcgtca gatacataga | 840 |
| tacaattcta ttaccccat ccataca | 867 |

<210> SEQ ID NO 47
<211> LENGTH: 1119
<212> TYPE: DNA
<213> ORGANISM: Artificial Sequence
<220> FEATURE:
<223> OTHER INFORMATION: pACU8
<220> FEATURE:
<223> OTHER INFORMATION: pACU8

<400> SEQUENCE: 47

| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg atttttattc caacactaag aaataatttc gccatttctt gaatgtattt | 180 |
| aaagatattt aatgctataa tagacattta aatccaattc ttccaacata caatgggagt | 240 |
| ttggccgagt ggtttaaggc gtcagattta ggtggattta acctctaaaa tctctgatat | 300 |
| cttcggatgc aagggttcga atcccttagc tctcattatt ttttgctttt tctcttgaat | 360 |
| tcgaaaaaga cattttttgct gtcagtcact gtcaagagat tcttttgctg gcatttcttc | 420 |
| cagaagcaaa aagagcgatg cgtcttttcc gctgaaccgt tccagcaaaa aagactacca | 480 |
| acgaattcga aaaagacatt tttgctgtca gtcactgtca agagattctt ttgctggcat | 540 |
| ttcttccaga agcaaaaaga gcgatgcgtc ttttccgctg aaccgttcca gcaaaaaaga | 600 |
| ctaccaacga attcgaaaaa gacattttttg ctgtcagtca ctgtcaagag attcttttgc | 660 |
| tggcatttct tccagaagca aaaagagcga tgcgtctttt ccgctgaacc gttccagcaa | 720 |
| aaagactac caacgaattc gaaaagaca tttttgctgt cagtcactgt caagagattc | 780 |
| ttttgctggc atttcttcca gaagcaaaaa gagcgatgcg tcttttccgc tgaaccgttc | 840 |
| cagcaaaaaa gactaccaac gaattctaat taagttagtc aaggcgccat cctcatgaaa | 900 |
| actgtgtaac ataataaccg aagtgtcgaa aaggtggcac cttgtccaat tgaacacgct | 960 |
| cgatgaaaaa aataagatat atataaggtt aagtaaagcg tctgttagaa aggaagtttt | 1020 |
| tccttttttct tgctctcttg tcttttcatc tactatttcc ttcgtgtaat acagggtcgt | 1080 |
| cagatacata gatacaattc tattaccccc atccataca | 1119 |

<210> SEQ ID NO 48
<211> LENGTH: 624
<212> TYPE: DNA
<213> ORGANISM: Artificial Sequence
<220> FEATURE:
<223> OTHER INFORMATION: pACU9
<220> FEATURE:
<223> OTHER INFORMATION: pACU9

<400> SEQUENCE: 48

| tatagttttt tctccttgac gttaaagtat agaggtatat taacaatttt ttgttgatac | 60 |
| ttttatgaca ttttgaataag aagtaataca aactgaaaat gttgaaagta ttagttaaag | 120 |
| tggttatgca gcttttccat ttatatatct gttaatagat caaaaatcat cgcttcgctg | 180 |
| attaattacc ccagaaataa ggctaaaaaa ctaatcgcat tatcatccga attcgaaaaa | 240 |
| gacatttttg ctgtcagtca ctgtcaagag attcttttgc tggcatttct tccagaagca | 300 |

| | |
|---|---|
| aaaagagcga tgcgtctttt ccgctgaacc gttccagcaa aaaagactac caacgaattc | 360 |
| gaaaaagaca tttttgctgt cagtcactgt caagagattc ttttgctggc atttcttcca | 420 |
| gaagcaaaaa gagcgatgcg tcttttccgc tgaaccgttc cagcaaaaaa gactaccaac | 480 |
| gaattcgggc tctttacatt tccacaacat ataagtaaga ttagatatgg atatgtatat | 540 |
| ggtggtaatg ccatgtaata tgattattaa acttctttgc gtccatccaa aaaaaaagta | 600 |
| agaattttttg aaaattcaat ataa | 624 |

<210> SEQ ID NO 49
<211> LENGTH: 876
<212> TYPE: DNA
<213> ORGANISM: Artificial Sequence
<220> FEATURE:
<223> OTHER INFORMATION: pACU10p
<220> FEATURE:
<223> OTHER INFORMATION: pACU10p

<400> SEQUENCE: 49

| | |
|---|---|
| ttatattgaa ttttcaaaaa ttcttacttt tttttttggat ggacgcaaag aagtttaata | 60 |
| atcatattac atggcattac caccatatac atatccatat ctaatcttac ttatatgttg | 120 |
| tggaaatgta aagagcccga attggttggt agtcttttttt gctggaacgg ttcagcggaa | 180 |
| aagacgcatc gctcttttttg cttctggaag aaatgccagc aaaagaatct cttgacagtg | 240 |
| actgacagca aaaatgtctt tttcgaattc gttggtagtc ttttttgctg aacggttca | 300 |
| gcggaaaaga cgcatcgctc ttttttgcttc tggaagaaat gccagcaaaa gaatctcttg | 360 |
| acagtgactg acagcaaaaa tgtctttttc gaattcgttg gtagtctttt ttgctggaac | 420 |
| ggttcagcgg aaaagacgca tcgctctttt tgcttctgga gaaatgcca gcaaaagaat | 480 |
| ctcttgacag tgactgacag caaaaatgtc ttttttcgaat tcgttggtag tctttttttgc | 540 |
| tggaacggtt cagcggaaaa gacgcatcgc tctttttgct tctggaagaa atgccagcaa | 600 |
| aagaatctct tgacagtgac tgacagcaaa aatgtctttt tccaattcgg atgataatgc | 660 |
| gattagttttt ttagccttat ttctggggta attaatcagc gaagcgatga ttttttgatct | 720 |
| attaacagat atataaatgg aaaagctgca taaccacttt aactaatact ttcaacattt | 780 |
| tcagtttgta ttacttctta tcaaatgtc ataaagtat caacaaaaaa ttgttaatat | 840 |
| acctctatac tttaacgtca aggagaaaaa actata | 876 |

<210> SEQ ID NO 50
<211> LENGTH: 633
<212> TYPE: DNA
<213> ORGANISM: Artificial Sequence
<220> FEATURE:
<223> OTHER INFORMATION: pACU11
<220> FEATURE:
<223> OTHER INFORMATION: pACU11

<400> SEQUENCE: 50

| | |
|---|---|
| gctcagcatc tgcttcttcc caagatgaa cgcggcgtta tgtcactaac gacgtgcacc | 60 |
| aacttgcggg aattcgaaaa agacattttt gctgtcagtc actgtcaaga gattcttttg | 120 |
| ctggcatttc ttccagaagc aaaaagagcg atgcgtcttt tccgctgaac cgttccagca | 180 |
| aaaaagacta ccaacgaatt ccaccgcacg cctttttttct gaagcccact tcgtggact | 240 |
| ttgccatata tgcaaaattc atgaagtgtg ataccaagtc agcatacacc tcactagggt | 300 |
| agtttctttg gttgtattga tcatttggtt catcgtggtt cattaatttt ttttctccat | 360 |
| tgctttctgg ctttgatctt actatcattt ggatttttgt cgaaggttgt agaattgtat | 420 |

```
gtgacaagtg gcaccaagca tatataaaaa aaaaaagcat tatcttccta ccagagttga    480
ttgttaaaaa cgtatttata gcaaacgcaa ttgtaattaa ttcttatttt gtatcttttc    540
ttcccttgtc tcaatctttt atttttattt tatttttctt ttcttagttt ctttcataac    600
accaagcaac taatactata acatacaata ata                                 633

<210> SEQ ID NO 51
<211> LENGTH: 1119
<212> TYPE: DNA
<213> ORGANISM: Artificial Sequence
<220> FEATURE:
<223> OTHER INFORMATION: pACU12
<220> FEATURE:
<223> OTHER INFORMATION: pACU12

<400> SEQUENCE: 51
ttacattatc aatccttgcg tttcagcttc cactaattta gatgactatt tctcatcatt    60
tgcgtcatct tctaacaccg tatatgataa tatactagta acgtaaatac tagttagtag    120
atgatagttg atttttattc caacactaag aaataaattc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tggttggtag tcttttttgc tggaacggtt cagcggaaaa gacgcatcgc tcttttttgct    420 tctggaagaa atgccagcaa agaatctct tgacagtgac tgacagcaaa aatgtctttt    480
tcgaattcgt tggtagtctt ttttgctgga acggttcagc ggaaaagacg catcgctctt    540
tttgcttctg gaagaaatgc cagcaaaaga atctcttgac agtgactgac agcaaaaatg    600 tcttttttcga attcgttggt agtctttttt gctggaacgg ttcagcggaa aagacgcatc    660 gctcttttg cttctggaag aaatgccagc aaaagaatct cttgacagtg actgacagca    720
aaaatgtctt tttcgaattc gttggtagtc ttttttgctg gaacggttca gcggaaaaga    780
cgcatcgctc ttttgcttc tggaagaaat gccagcaaaa gaatctcttg acagtgactg    840
acagcaaaaa tgtcttttt caattctaat taagttagtc aaggcgccat cctcatgaaa    900
actgtgtaac ataataaccg aagtgtcgaa aaggtggcac cttgtccaat tgaacacgct    960
cgatgaaaaa aataagatat ataaggtt aagtaaagcg tctgttagaa aggaagtttt    1020 tccttttttct tgctctcttg tcttttcatc tactatttcc ttcgtgtaat acagggtcgt    1080
cagatacata gatacaattc tattaccccc atccataca                           1119

<210> SEQ ID NO 52
<211> LENGTH: 1497
<212> TYPE: DNA
<213> ORGANISM: Artificial Sequence
<220> FEATURE:
<223> OTHER INFORMATION: pACU13
<220> FEATURE:
<223> OTHER INFORMATION: pACU13

<400> SEQUENCE: 52
ttacattatc aatccttgcg tttcagcttc cactaattta gatgactatt tctcatcatt    60
tgcgtcatct tctaacaccg tatatgataa tatactagta acgtaaatac tagttagtag    120
atgatagttg atttttattc caacactaag aaataaattc gccatttctt gaatgtattt    180
aaagatattt aatgctataa tagacattta aatccaattc ttccaacata caatgggagt    240
```

```
ttggccgagt ggtttaaggc gtcagattta ggtggattta acctctaaaa tctctgatat        300
cttcggatgc aagggttcga atcccttagc tctcattatt ttttgctttt tctcttgaat        360
tggttggtag tcttttttgc tggaacggtt cagcggaaaa gacgcatcgc tcttttttgct       420 tctggaagaa atgccagcaa aagaatctct tgacagtgac tgacagcaaa aatgtctttt       480
tcgaattcgt tggtagtctt ttttgctgga acggttcagc ggaaaagacg catcgctctt        540
tttgcttctg gaagaaatgc cagcaaaaga atctcttgac agtgactgac agcaaaaatg       600 tcttttcga attcgttggt agtcttttt gctggaacgg ttcagcggaa aagacgcatc         660
gctctttttg cttctggaag aaatgccagc aaaagaatct cttgacagtg actgacagca       720
aaaatgtctt tttcgaattc gttggtagtc ttttttgctg gaacggttca gcggaaaaga       780
cgcatcgctc tttttgcttc tggaagaaat gccagcaaaa gaatctcttg acagtgactg       840
acagcaaaaa tgtcttttc gaattcgttg gtagtctttt ttgctggaac ggttcagcgg        900
aaaagacgca tcgctctttt tgcttctgga agaaatgcca gcaaaagaat ctcttgacag       960
tgactgacag caaaaatgtc ttttttcgaat tcgttggtag tcttttttgc tggaacggtt     1020
cagcggaaaa gacgcatcgc tcttttttgct tctggaagaa atgccagcaa aagaatctct     1080
tgacagtgac tgacagcaaa aatgtctttt tcgaattcgt tggtagtctt ttttgctgga      1140
acggttcagc ggaaaagacg catcgctctt tttgcttctg gaagaaatgc cagcaaaaga     1200
atctcttgac agtgactgac agcaaaaatg tcttttccca attctaatta gttagtcaa      1260 ggcgccatcc tcatgaaaac tgtgtaacat aataaccgaa gtgtcgaaaa ggtggcacct     1320
tgtccaattg aacacgctcg atgaaaaaaa taagatatat ataaggttaa gtaaagcgtc    1380
tgttagaaag gaagttttc ctttttcttg ctctcttgtc ttttcatcta ctatttcctt     1440
cgtgtaatac agggtcgtca gatacataga tacaattcta ttaccccat ccataca        1497
```

<210> SEQ ID NO 53
<211> LENGTH: 1011
<212> TYPE: DNA
<213> ORGANISM: Artificial Sequence
<220> FEATURE:
<223> OTHER INFORMATION: pACU14
<220> FEATURE:
<223> OTHER INFORMATION: pACU14

<400> SEQUENCE: 53

```
gctcagcatc tgcttcttcc caaagatgaa cgcggcgtta tgtcactaac gacgtgcacc         60
aacttgcggg aattggaaaa agacattttt gctgtcagtc actgtcaaga gattcttttg        120
ctggcatttc ttccagaagc aaaaagagcg atgcgtcttt tccgctgaac cgttccagca       180
aaaaagacta ccaacgaatt cgaaaaagac atttttgctg tcagtcactg tcaagagatt       240
cttttgctgg catttcttcc agaagcaaaa agagcgatgc gtcttttccg ctgaaccgtt       300
ccagcaaaaa agactaccaa cgaattcgaa aaagacattt tgctgtcag tcactgtcaa       360 gagattcttt tgctggcatt tcttccagaa gcaaaaagag cgatgcgtct tttccgctga      420
accgttccag caaaaagac taccaacgaa ttcgaaaaag acattttgc tgtcagtcac        480 tgtcaagaga ttcttttgct ggcatttctt ccagaagcaa aaagagcgat gcgtcttttc       540
cgctgaaccg ttcagcaaa aaagactacc aaccaattcc accgcacgcc tttttctga       600 agcccacttt cgtggacttt gccatatatg caaaattcat gaagtgtgat accaagtcag      660
catacacctc actagggtag tttctttggt tgtattgatc atttggttca tcgtggttca      720
ttaatttttt ttctccattg ctttctggct ttgatcttac tatcatttgg atttttgtcg      780
```

```
aaggttgtag aattgtatgt gacaagtggc accaagcata tataaaaaaa aaaagcatta      840
tcttcctacc agagttgatt gttaaaaacg tatttatagc aaacgcaatt gtaattaatt      900
cttattttgt atcttttctt cccttgtctc aatcttttat ttttatttta tttttctttt      960
cttagtttct ttcataacac caagcaacta atactataac atacaataat a              1011

<210> SEQ ID NO 54
<211> LENGTH: 398
<212> TYPE: DNA
<213> ORGANISM: Artificial Sequence
<220> FEATURE:
<223> OTHER INFORMATION: pACU15
<220> FEATURE:
<223> OTHER INFORMATION: pACU15

<400> SEQUENCE: 54
tatagttttt tctccttgac gttaaagtat agaggtatat taacaatttt ttgttgatac       60
ttttatgaca tttgaataag aagtaataca aactgaaaat gttgaaagta ttagttaaag      120
tggttatgca gcttttccat ttatatatct gttaatagat caaaaatcat cgcttcgctg      180
attaattacc ccagaaataa ggctaaaaaa ctaatcgcat tatcatccga attcgttggt      240 agtcttttt gctggaacgg ttcagcggaa aagacgcatc gctcttttg cttctggaag       300 aaatgccagc aaaagaatct cttgacagtg actgacagca aaaatgtctt tttcgaattc      360
gggctcttta catttccaca acatataagt aagattag                              398

<210> SEQ ID NO 55
<211> LENGTH: 428
<212> TYPE: DNA
<213> ORGANISM: Artificial Sequence
<220> FEATURE:
<223> OTHER INFORMATION: pGAL/CUP1p
<220> FEATURE:
<223> OTHER INFORMATION: pGAL/CUP1p

<400> SEQUENCE: 55
ttatattgaa ttttcaaaaa ttcttacttt tttttggat ggacgcaaag aagtttaata       60
atcatattac atggcattac caccatatac atatccatat ctaatcttac ttatatgttg      120
tggaaatgta aagagcccga attcgaaaaa gacattttg ctgtcagtca ctgtcaagag       180
attcttttgc tggcatttct tccagaagca aaaagagcga tgcgtctttt ccgctgaacc      240
gttccagcaa aaaagactac caacgcaata tggattgtca gaatcatata aaagagaagc      300
aaataactcc ttgtcttgta tcaattgcat tataatatct tcttgttagt gcaatatcat      360
atagaagtca tcgaaataga tattaagaaa acaaactgt acaatcaatc aatcaatcat       420
cacataaa                                                              428

<210> SEQ ID NO 56
<211> LENGTH: 518
<212> TYPE: DNA
<213> ORGANISM: Saccharomyces cerevisiae
<220> FEATURE:
<223> OTHER INFORMATION: pCRS5
<220> FEATURE:
<223> OTHER INFORMATION: pCRS5

<400> SEQUENCE: 56
gtggacgaaa agacataact gcagaagtac agctgccttt atttcttgtg gtcatttatt       60
gcttttattt tcaagtcaga tatacaagaa aatcaaatcc catcgtcaac gtcacgtata      120
```

| | |
|---|---|
| aacgattaat ttacagtaat accatactct accaacatta ttttagtccg acgttcagtc | 180 |
| ctgtaggtgt tccaaatcct tctggcattg acttctgtgc agaaacccct caaaatgagt | 240 |
| tccactttac gtcagatcgc ataacaaccg gtcatatatt ttttctttt gctaaacccc | 300 |
| ctactgcaag cacttttaag aaaaagaaca ataaatgcgt ctttattgct gtgtggaagt | 360 |
| gattttgtc tttcggacaa aaaaaggata gggatgcgag agggctgtga agtagtgatc | 420 |
| aagcggggcc tatataagaa gggcgcacat cgtccccct aagaatagcg aagcgatatt | 480 |
| acactgaaca ctacaatgtc aaatagtact caataaat | 518 |

<210> SEQ ID NO 57
<211> LENGTH: 510
<212> TYPE: DNA
<213> ORGANISM: Saccharomyces cerevisiae
<220> FEATURE:
<223> OTHER INFORMATION: pCHA1
<220> FEATURE:
<223> OTHER INFORMATION: pCHA1

<400> SEQUENCE: 57

| | |
|---|---|
| gatctctgct gacgttgtat ccacagatct aattgcaaga tagcctcttg cgaccttatt | 60 |
| aaaagcctct ccgtgatatc ctctagggct tgggttgcca ttaatcgatg tgtccttgtt | 120 |
| tccttatgcg agctgtttct tatctatctt atggtcccat tctttactgc actgtttaca | 180 |
| ttttgatcaa ttgcgaaatg ttcctactat ttttctttt ctcttttcgc gagtactaat | 240 |
| caccgcgaac ggaaactaat gagtcctctg cgcggagaca tgattccgca tgggcggctc | 300 |
| ctgttaagcc ccagcggaaa tgtaattcca ctgagtgtca ttaaatagtg ccaaagcttt | 360 |
| atcaaattgt ttgcgatgag ataagataaa agggacaata tgaggaggaa cacaggtata | 420 |
| taaatatcgc caaataaaag gaaatgtttt atacagtttt ctcttttta agtgctggat | 480 |
| agacaagaga caggaaaatt aaccagcgag | 510 |

<210> SEQ ID NO 58
<211> LENGTH: 601
<212> TYPE: DNA
<213> ORGANISM: Saccharomyces cerevisiae
<220> FEATURE:
<223> OTHER INFORMATION: pCTR1
<220> FEATURE:
<223> OTHER INFORMATION: pCTR1

<400> SEQUENCE: 58

| | |
|---|---|
| caagtccgat tgttcctctt caggagcttc ctgaaccaaa ctttttccgc aaggccgcat | 60 |
| tttgaaccgt attttgctcg ttccagccct tccacgtttt tgttatctaa gcaacttggc | 120 |
| acatttccct actatactac aaaccgatac gtaaatactt ccctaaatag catatgaatt | 180 |
| attcagtaat ttttaaggat cgaaactgca cctcaactat tcgttactgt ggttatgttc | 240 |
| tcatgtattg atgcaaatca tgggatattt gctcaagacg acggtaaaat gagcaaaaat | 300 |
| ggcacgatcc tgaaaagagc acttttcaag attcgggcta caaaatgcaa cataaaaaat | 360 |
| gttgtattgt catctcgaca gggtcttgta tgttttattc ctcttatgat tagttcacat | 420 |
| tagtaaaaca gatacgcagt gtgctcttaa taaacaacta ctccatagct ttatttgcat | 480 |
| aacaaaactt ttaagcacaa acttaaacag gtggagtaat agttcggcgg cgactcaaat | 540 |
| tacatttgtt ggaagaatcg aatagaaaat aaaaaaaagt gtattatatt tgacattcaa | 600 |
| a | 601 |

<210> SEQ ID NO 59
<211> LENGTH: 522
<212> TYPE: DNA
<213> ORGANISM: Saccharomyces cerevisiae
<220> FEATURE:
<223> OTHER INFORMATION: pCTR3
<220> FEATURE:
<223> OTHER INFORMATION: pCTR3

<400> SEQUENCE: 59

```
gatgtgatga caaaacctct tccgataaaa acatttaaac tattaacaaa caaatggatt    60
cattagatct attacattat gggtggtatg ttggaataaa aatcaactat catctactaa   120
ctagtattta cgttactagt atattatcat atacggtgtt agaagatgac gcaaatgatg   180
agaaatagtc atctaaatta gtggaagctg aaacgcaagg attgataatg taataggatc   240
aatgaatatt aacatataaa acgatgataa taatatttat agaattgtgt agaattgcag   300
attccctttt atggattcct aaatcctcca ggagaacttc tagtatatct acatacctaa   360
tattattgcc ttattaaaaa tggaatccca acaattacat caaaatccac attctcttca   420
cttctccgat agacttgtaa tttatcttat ttcatttcct aacactttga tcgaagaaga   480
gggataacaa cagacgaaaa cacatttaag ggctatacaa ag                      522
```

<210> SEQ ID NO 60
<211> LENGTH: 675
<212> TYPE: DNA
<213> ORGANISM: Artificial Sequence
<220> FEATURE:
<223> OTHER INFORMATION: pCUR1
<220> FEATURE:
<223> OTHER INFORMATION: pCUR1

<400> SEQUENCE: 60

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg atttttattc caacactaag aaataatttc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tgtcatggga tatttgctca agacgacggt aaaatgagca aatatggcac gatcctcaat   420
tctaattaag ttagtcaagg cgccatcctc atgaaaactg tgtaacataa taaccgaagt   480
gtcgaaaagg tggcaccttg tccaattgaa cacgctcgat gaaaaaaata agatatatat   540
aaggttaagt aaagcgtctg ttagaaagga agttttttcct ttttcttgct ctcttgtctt   600
ttcatctact atttccttcg tgtaatacag ggtcgtcaga tacatagata caattctatt   660
acccccatcc ataca                                                    675
```

<210> SEQ ID NO 61
<211> LENGTH: 674
<212> TYPE: DNA
<213> ORGANISM: Artificial Sequence
<220> FEATURE:
<223> OTHER INFORMATION: pCUR2
<220> FEATURE:
<223> OTHER INFORMATION: pCUR2

<400> SEQUENCE: 61

```
ttacattatc aatccttgcg tttcagcttc cactaattta gatgactatt tctcatcatt    60
```

```
tgcgtcatct tctaacaccg tatatgataa tatactagta acgtaaatac tagttagtag    120
atgatagttg attttattc caacactaag aaataatttc gccatttctt gaatgtattt     180
aaagatattt aatgctataa tagacattta atccaattc ttccaacata caatgggagt     240
ttggccgagt ggtttaaggc gtcagattta ggtggattta acctctaaaa tctctgatat    300
cttcggatgc aagggttcga atcccttagc tctcattatt ttttgctttt tctcttgatt    360
gaggatcgtg ccatatttgc tcattttacc gtcgtcttga gcaaatatcc catgacaatt    420
ctaattaagt tagtcaaggc gccatcctca tgaaaactgt gtaacataat aaccgaagtg    480 tcgaaaggt ggcaccttgt ccaattgaac acgctcgatg aaaaaaataa gatatatata     540
aggttaagta aagcgtctgt tagaaaggaa gttttcctt tttcttgctc tcttgtcttt     600
tcatctacta tttccttcgt gtaatacagg gtcgtcagat acatagatac aattctatta    660 ccccatcca taca                                                       674

<210> SEQ ID NO 62
<211> LENGTH: 794
<212> TYPE: DNA
<213> ORGANISM: Artificial Sequence
<220> FEATURE:
<223> OTHER INFORMATION: pCUR3
<220> FEATURE:
<223> OTHER INFORMATION: pCUR3

<400> SEQUENCE: 62
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataatttc gccatttctt gaatgtattt     180
aaagatattt aatgctataa tagacattta atccaattc ttccaacata caatgggagt     240
ttggccgagt ggtttaaggc gtcagattta ggtggattta acctctaaaa tctctgatat    300
cttcggatgc aagggttcga atcccttagc tctcattatt ttttgctttt tctcttgaat    360
taggatcgtg ccatatttgc tcattttacc gtcgtcttga gcaaatatcc catgacaatt    420
gaggatcgtg ccatatttgc tcattttacc gtcgtcttga gcaaatatcc catgacaatt    480
gaggatcgtg ccatatttgc tcattttacc gtcgtcttga gcaaatatcc catgacaatt    540
ctaattaagt tagtcaaggc gccatcctca tgaaaactgt gtaacataat aaccgaagtg    600 tcgaaaggt ggcaccttgt ccaattgaac acgctcgatg aaaaaaataa gatatatata     660
aggttaagta aagcgtctgt tagaaaggaa gttttcctt tttcttgctc tcttgtcttt     720
tcatctacta tttccttcgt gtaatacagg gtcgtcagat acatagatac aattctatta    780 ccccatcca taca                                                       794

<210> SEQ ID NO 63
<211> LENGTH: 850
<212> TYPE: DNA
<213> ORGANISM: Artificial Sequence
<220> FEATURE:
<223> OTHER INFORMATION: pCUR4
<220> FEATURE:
<223> OTHER INFORMATION: pCUR4

<400> SEQUENCE: 63
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataatttc gccatttctt gaatgtattt     180
```

```
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tgtcatggga tatttgctca agacgacggt aaaatgagca aatatggcac gatcctcaat    420
tgtcatggga tatttgctca agacgacggt aaaatgagca aatatggcac gatcctcaat    480
gtcatgggat atttgctcaa gacgacggta aaatgagcaa atatggcacg atcctcaatt    540
gtcatgggat atttgctcaa gacgacggta aaatgagcaa atatcccatg acaattctaa    600
ttaagttagt caaggcgcca tcctcatgaa aactgtgtaa cataataacc gaagtgtcga    660
aaaggtggca ccttgtccaa ttgaacacgc tcgatgaaaa aaataagata tatataaggt    720
taagtaaagc gtctgttaga aaggaagttt ttccttttc ttgctctctt gtcttttcat    780
ctactatttc cttcgtgtaa tacagggtcg tcagatacat agatacaatt ctattacccc    840
catccataca                                                          850

<210> SEQ ID NO 64
<211> LENGTH: 491
<212> TYPE: DNA
<213> ORGANISM: Artificial Sequence
<220> FEATURE:
<223> OTHER INFORMATION: pCUR5p
<220> FEATURE:
<223> OTHER INFORMATION: pCUR5p

<400> SEQUENCE: 64
ttatattgaa ttttcaaaaa ttcttacttt ttttttggat ggacgcaaag aagtttaata     60
atcatattac atggcattac caccatatac atatccatat ctaatcttac ttatatgttg    120
tggaaatgta aagagcccga attgtcatgg gatatttgct caagacgacg gtaaaatgag    180
caaatatggc acgatcctca attgtcatgg gatatttgct caagacgacg gtaaaatgag    240
caaatatggc acgatcccaa ttcggatgat aatgcgatta gttttttagc cttatttctg    300
gggtaattaa tcagcgaagc gatgattttt gatctattaa cagatatata aatggaaaag    360
ctgcataacc actttaacta atactttcaa cattttcagt ttgtattact tcttattcaa    420
atgtcataaa agtatcaaca aaaaattgtt aatatacctc tatactttaa cgtcaaggag    480
aaaaaactat a                                                        491

<210> SEQ ID NO 65
<211> LENGTH: 833
<212> TYPE: DNA
<213> ORGANISM: Artificial Sequence
<220> FEATURE:
<223> OTHER INFORMATION: pCUR6
<220> FEATURE:
<223> OTHER INFORMATION: pCUR6

<400> SEQUENCE: 65
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg atttttattc caacactaag aaataatttc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccgaatt gaggatcgtg ccatatttgc tcattttacc    360
```

```
gtcgtcttga gcaaatatcc catgacaatt gaggatcgtg ccatatttgc tcattttacc      420
gtcgtcttga gcaaatatcc catgacaatt gaggatcgtg ccatatttgc tcattttacc      480
gtcgtcttga gcaaatatcc catgacaatt catgatcgca aaatggcaaa tggcacgtga      540
agctgtcgat attggggaac tgtggtggtt ggcaaatgac taattaagtt agtcaaggcg      600
ccatcctcat gaaaactgtg taacataata accgaagtgt cgaaaggtg gcaccttgtc       660 caattgaaca cgctcgatga aaaaaataag atatatataa ggttaagtaa agcgtctgtt      720
agaaaggaag ttttccttt tcttgctct cttgtctttt catctactat ttccttcgtg        780
taatacaggg tcgtcagata catagataca attctattac ccccatccat aca             833

<210> SEQ ID NO 66
<211> LENGTH: 803
<212> TYPE: DNA
<213> ORGANISM: Artificial Sequence
<220> FEATURE:
<223> OTHER INFORMATION: pCUR7
<220> FEATURE:
<223> OTHER INFORMATION: pCUR7

<400> SEQUENCE: 66
gtgagtaagg aaagagtgag gaactatcgc atacctgcat ttaaagatgc cgatttgggc      60
gcgaatcctt tattttggct tcaccctcat actattatca gggccagaaa aaggaagtgt     120
ttccctcctt cttgaattga tgttaccctc ataaagcacg tggcctctta tcgagaaaga     180
aattaccgtc gctcgtgatt tgtttgcaaa aagaacaaaa ctgaattcag gatcgtgcca     240
tatttgctca ttttaccgtc gtcttgagca aatatcccat gacaattgag gatcgtgcca    300
tatttgctca ttttaccgtc gtcttgagca aatatcccat gagaattctt cctgtcttcc    360
tattgattgc agcttccaat ttcgtcacac aacaaggtcc tagcgacggc tcacaggttt     420
tgtaacaagc aatcgaaggt tctggaatgg cgggaaaggg tttagtacca catgctatga    480
tgcccactgt gatctccaga gcaaagttcg ttcgatcgta ctgttactct ctctcttca     540 aacagaattg tccgaatcgt gtgacaacaa cagcctgttc tcacacactc ttttcttcta    600 accaagggg tggttagtt tagtagaacc tcgtgaaact tacatttaca tatatataaa      660
cttgcataaa ttggtcaatg caagaaatac atatttggtc ttttctaatt cgtagttttt    720
caagttctta gatgctttct ttttctcttt tttacagatc atcaaggaag taattatcta    780 cttttttacaa caaatataaa aca                                            803

<210> SEQ ID NO 67
<211> LENGTH: 863
<212> TYPE: DNA
<213> ORGANISM: Artificial Sequence
<220> FEATURE:
<223> OTHER INFORMATION: pCUR8
<220> FEATURE:
<223> OTHER INFORMATION: pCUR8

<400> SEQUENCE: 67
gtgagtaagg aaagagtgag gaactatcgc atacctgcat ttaaagatgc cgatttgggc      60
gcgaatcctt tattttggct tcaccctcat actattatca gggccagaaa aaggaagtgt     120
ttccctcctt cttgaattga tgttaccctc ataaagcacg tggcctctta tcgagaaaga     180
aattaccgtc gctcgtgatt tgtttgcaaa aagaacaaaa ctgaattcag gatcgtgcca     240
tatttgctca ttttaccgtc gtcttgagca aatatcccat gacaattgag gatcgtgcca    300
tatttgctca ttttaccgtc gtcttgagca aatatcccat gacaattgag gatcgtgcca    360
```

```
tatttgctca ttttaccgtc gtcttgagca aatatcccat gagaattctt cctgtcttcc    420
tattgattgc agcttccaat ttcgtcacac aacaaggtcc tagcgacggc tcacaggttt    480
tgtaacaagc aatcgaaggt tctggaatgg cgggaaaggg tttagtacca catgctatga    540
tgcccactgt gatctccaga gcaaagttcg ttcgatcgta ctgttactct ctctctttca    600
aacagaattg tccgaatcgt gtgacaacaa cagcctgttc tcacacactc ttttcttcta    660
accaaggggg tggtttagtt tagtagaacc tcgtgaaact tacatttaca tatatataaa    720
cttgcataaa ttggtcaatg caagaaatac atatttggtc ttttctaatt cgtagttttt    780
caagttctta gatgctttct ttttctcttt tttacagatc atcaaggaag taattatcta    840 cttttttacaa caaatataaa aca                                           863
```

```
<210> SEQ ID NO 68
<211> LENGTH: 863
<212> TYPE: DNA
<213> ORGANISM: Artificial Sequence
<220> FEATURE:
<223> OTHER INFORMATION: pCUR9
<220> FEATURE:
<223> OTHER INFORMATION: pCUR9

<400> SEQUENCE: 68
gtgagtaagg aaagagtgag gaactatcgc atacctgcat ttaaagatgc cgatttgggc     60
gcgaatcctt tatttggct tcaccctcat actattatca gggccagaaa aaggaagtgt    120
ttccctcctt cttgaattga tgttaccctc ataaagcacg tggcctctta tcgagaaaga   180
aattaccgtc gctcgtgatt tgtttgcaaa aagaacaaaa ctgaattctc atgggatatt   240
tgctcaagac gacggtaaaa tgagcaaata tggcacgatc ctcaattgtc atgggatatt   300
tgctcaagac gacggtaaaa tgagcaaata tggcacgatc ctcaattgtc atgggatatt   360
tgctcaagac gacggtaaaa tgagcaaata tggcacgatc ctgaattctt cctgtcttcc   420
tattgattgc agcttccaat ttcgtcacac aacaaggtcc tagcgacggc tcacaggttt   480
tgtaacaagc aatcgaaggt tctggaatgg cgggaaaggg tttagtacca catgctatga   540
tgcccactgt gatctccaga gcaaagttcg ttcgatcgta ctgttactct ctctctttca   600
aacagaattg tccgaatcgt gtgacaacaa cagcctgttc tcacacactc ttttcttcta   660
accaaggggg tggtttagtt tagtagaacc tcgtgaaact tacatttaca tatatataaa   720
cttgcataaa ttggtcaatg caagaaatac atatttggtc ttttctaatt cgtagttttt   780
caagttctta gatgctttct ttttctcttt tttacagatc atcaaggaag taattatcta   840 cttttttacaa caaatataaa aca                                          863
```

```
<210> SEQ ID NO 69
<211> LENGTH: 923
<212> TYPE: DNA
<213> ORGANISM: Artificial Sequence
<220> FEATURE:
<223> OTHER INFORMATION: pCUR10
<220> FEATURE:
<223> OTHER INFORMATION: pCUR10

<400> SEQUENCE: 69
gtgagtaagg aaagagtgag gaactatcgc atacctgcat ttaaagatgc cgatttgggc     60
gcgaatcctt tatttggct tcaccctcat actattatca gggccagaaa aaggaagtgt    120
ttccctcctt cttgaattga tgttaccctc ataaagcacg tggcctctta tcgagaaaga   180
```

```
aattaccgtc gctcgtgatt tgtttgcaaa aagaacaaaa ctgaattctc atgggatatt    240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctcaattgtc atgggatatt    420
tgctcaagac gacggtaaaa tgagcaaata tggcacgatc ctgaattctt cctgtcttcc    480
tattgattgc agcttccaat tcgtcacac aacaaggtcc tagcgacggc tcacaggttt     540
tgtaacaagc aatcgaaggt tctggaatgg cgggaaaggg tttagtacca catgctatga    600
tgcccactgt gatctccaga gcaaagttcg ttcgatcgta ctgttactct ctctctttca    660
aacagaattg tccgaatcgt gtgacaacaa cagcctgttc tcacacactc ttttcttcta    720
accaaggggg tggtttagtt tagtagaacc tcgtgaaact tacatttaca tatatataaa    780
cttgcataaa ttggtcaatg caagaaatac atatttggtc ttttctaatt cgtagttttt    840
caagttctta gatgctttct ttttctcttt tttacagatc atcaaggaag taattatcta    900 cttttttacaa caaatataaa aca                                           923
```

<210> SEQ ID NO 70
<211> LENGTH: 983
<212> TYPE: DNA
<213> ORGANISM: Artificial Sequence
<220> FEATURE:
<223> OTHER INFORMATION: pCUR11
<220> FEATURE:
<223> OTHER INFORMATION: pCUR11

<400> SEQUENCE: 70

```
gtgagtaagg aaagagtgag gaactatcgc atacctgcat ttaaagatgc cgatttgggc    60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctcaattgtc atgggatatt    420
tgctcaagac gacggtaaaa tgagcaaata tggcacgatc ctcaattgtc atgggatatt    480
tgctcaagac gacggtaaaa tgagcaaata tggcacgatc ctgaattctt cctgtcttcc    540
tattgattgc agcttccaat tcgtcacac aacaaggtcc tagcgacggc tcacaggttt     600
tgtaacaagc aatcgaaggt tctggaatgg cgggaaaggg tttagtacca catgctatga    660
tgcccactgt gatctccaga gcaaagttcg ttcgatcgta ctgttactct ctctctttca    720
aacagaattg tccgaatcgt gtgacaacaa cagcctgttc tcacacactc ttttcttcta    780
accaaggggg tggtttagtt tagtagaacc tcgtgaaact tacatttaca tatatataaa    840
cttgcataaa ttggtcaatg caagaaatac atatttggtc ttttctaatt cgtagttttt    900
caagttctta gatgctttct ttttctcttt tttacagatc atcaaggaag taattatcta    960 cttttttacaa caaatataaa aca                                           983
```

<210> SEQ ID NO 71
<211> LENGTH: 1043
<212> TYPE: DNA
<213> ORGANISM: Artificial Sequence
<220> FEATURE:
<223> OTHER INFORMATION: pCUR12

<220> FEATURE:
<223> OTHER INFORMATION: pCUR12

<400> SEQUENCE: 71

| | | | | | |
|---|---|---|---|---|---|
| gtgagtaagg | aaagagtgag | gaactatcgc | atacctgcat | ttaaagatgc | cgatttgggc | 60 |
| gcgaatcctt | tattttggct | tcaccctcat | actattatca | gggccagaaa | aaggaagtgt | 120 |
| ttccctcctt | cttgaattga | tgttaccctc | ataaagcacg | tggcctctta | tcgagaaaga | 180 |
| aattaccgtc | gctcgtgatt | tgtttgcaaa | aagaacaaaa | ctgaattcag | gatcgtgcca | 240 |
| tatttgctca | ttttaccgtc | gtcttgagca | aatatcccat | gacaattgag | gatcgtgcca | 300 |
| tatttgctca | ttttaccgtc | gtcttgagca | aatatcccat | gacaattgag | gatcgtgcca | 360 |
| tatttgctca | ttttaccgtc | gtcttgagca | aatatcccat | gagaattcag | gatcgtgcca | 420 |
| tatttgctca | ttttaccgtc | gtcttgagca | aatatcccat | gacaattgag | gatcgtgcca | 480 |
| tatttgctca | ttttaccgtc | gtcttgagca | aatatcccat | gacaattgag | gatcgtgcca | 540 |
| tatttgctca | ttttaccgtc | gtcttgagca | aatatcccat | gagaattctt | cctgtcttcc | 600 |
| tattgattgc | agcttccaat | ttcgtcacac | aacaaggtcc | tagcgacggc | tcacaggttt | 660 |
| tgtaacaagc | aatcgaaggt | tctggaatgg | cgggaaaggg | tttagtacca | catgctatga | 720 |
| tgcccactgt | gatctccaga | gcaaagttcg | ttcgatcgta | ctgttactct | ctctctttca | 780 |
| aacagaattg | tccgaatcgt | gtgacaacaa | cagcctgttc | tcacacactc | ttttcttcta | 840 |
| accaaggggg | tggtttagtt | tagtagaacc | tcgtgaaact | tacatttaca | tatatataaa | 900 |
| cttgcataaa | ttggtcaatg | caagaaatac | atatttggtc | ttttctaatt | cgtagttttt | 960 |
| caagttctta | gatgctttct | ttttctcttt | tttacagatc | atcaaggaag | taattatcta | 1020 |
| ctttttacaa | caaatataaa | aca | | | | 1043 |

<210> SEQ ID NO 72
<211> LENGTH: 1043
<212> TYPE: DNA
<213> ORGANISM: Artificial Sequence
<220> FEATURE:
<223> OTHER INFORMATION: pCUR13
<220> FEATURE:
<223> OTHER INFORMATION: pCUR13

<400> SEQUENCE: 72

| | | | | | |
|---|---|---|---|---|---|
| gtgagtaagg | aaagagtgag | gaactatcgc | atacctgcat | ttaaagatgc | cgatttgggc | 60 |
| gcgaatcctt | tattttggct | tcaccctcat | actattatca | gggccagaaa | aaggaagtgt | 120 |
| ttccctcctt | cttgaattga | tgttaccctc | ataaagcacg | tggcctctta | tcgagaaaga | 180 |
| aattaccgtc | gctcgtgatt | tgtttgcaaa | aagaacaaaa | ctgaattctc | atgggatatt | 240 |
| tgctcaagac | gacggtaaaa | tgagcaaata | tggcacgatc | ctcaattgtc | atgggatatt | 300 |
| tgctcaagac | gacggtaaaa | tgagcaaata | tggcacgatc | ctcaattgtc | atgggatatt | 360 |
| tgctcaagac | gacggtaaaa | tgagcaaata | tggcacgatc | ctgaattctc | atgggatatt | 420 |
| tgctcaagac | gacggtaaaa | tgagcaaata | tggcacgatc | ctcaattgtc | atgggatatt | 480 |
| tgctcaagac | gacggtaaaa | tgagcaaata | tggcacgatc | ctcaattgtc | atgggatatt | 540 |
| tgctcaagac | gacggtaaaa | tgagcaaata | tggcacgatc | ctgaattctt | cctgtcttcc | 600 |
| tattgattgc | agcttccaat | ttcgtcacac | aacaaggtcc | tagcgacggc | tcacaggttt | 660 |
| tgtaacaagc | aatcgaaggt | tctggaatgg | cgggaaaggg | tttagtacca | catgctatga | 720 |
| tgcccactgt | gatctccaga | gcaaagttcg | ttcgatcgta | ctgttactct | ctctctttca | 780 |

```
aacagaattg tccgaatcgt gtgacaacaa cagcctgttc tcacacactc tttcttcta      840 accaagggg tggtttagtt tagtagaacc tcgtgaaact tacattaca tatatataaa       900 cttgcataaa ttggtcaatg caagaaatac atatttggtc ttttctaatt cgtagttttt    960
caagttctta gatgctttct tttctctttt tttacagatc atcaaggaag taattatcta   1020 cttttttacaa caaatataaa aca                                           1043
```

<210> SEQ ID NO 73
<211> LENGTH: 1223
<212> TYPE: DNA
<213> ORGANISM: Artificial Sequence
<220> FEATURE:
<223> OTHER INFORMATION: pCUR14
<220> FEATURE:
<223> OTHER INFORMATION: pCUR14

<400> SEQUENCE: 73

```
gtgagtaagg aaagagtgag gaactatcgc atacctgcat ttaaagatgc cgatttgggc      60
gcgaatcctt tattttggct tcaccctcat actattatca gggccagaaa aaggaagtgt     120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctgaattctc atgggatatt    420
tgctcaagac gacggtaaaa tgagcaaata tggcacgatc ctcaattgtc atgggatatt    480
tgctcaagac gacggtaaaa tgagcaaata tggcacgatc ctcaattgtc atgggatatt    540
tgctcaagac gacggtaaaa tgagcaaata tggcacgatc ctgaattctc atgggatatt    600
tgctcaagac gacggtaaaa tgagcaaata tggcacgatc ctcaattgtc atgggatatt    660
tgctcaagac gacggtaaaa tgagcaaata tggcacgatc ctcaattgtc atgggatatt    720
tgctcaagac gacggtaaaa tgagcaaata tggcacgatc ctgaattctt cctgtcttcc    780
tattgattgc agcttccaat ttcgtcacac aacaaggtcc tagcgacggc tcacaggttt    840
tgtaacaagc aatcgaaggt tctggaatgg cgggaaaggg tttagtacca catgctatga    900
tgcccactgt gatctccaga gcaaagttcg ttcgatcgta ctgttactct ctctctttca    960
aacagaattg tccgaatcgt gtgacaacaa cagcctgttc tcacacactc tttcttcta   1020 accaagggg tggtttagtt tagtagaacc tcgtgaaact tacattaca tatatataaa    1080 cttgcataaa ttggtcaatg caagaaatac atatttggtc ttttctaatt cgtagttttt   1140
caagttctta gatgctttct tttctctttt tttacagatc atcaaggaag taattatcta   1200 cttttttacaa caaatataaa aca                                          1223
```

<210> SEQ ID NO 74
<211> LENGTH: 1283
<212> TYPE: DNA
<213> ORGANISM: Artificial Sequence
<220> FEATURE:
<223> OTHER INFORMATION: pCUR15
<220> FEATURE:
<223> OTHER INFORMATION: pCUR15

<400> SEQUENCE: 74

```
gtgagtaagg aaagagtgag gaactatcgc atacctgcat ttaaagatgc cgatttgggc      60
gcgaatcctt tattttggct tcaccctcat actattatca gggccagaaa aaggaagtgt     120
```

```
ttccctccctt cttgaattga tgttaccctc ataaagcacg tggcctctta tcgagaaaga        180
aattaccgtc gctcgtgatt tgtttgcaaa aagaacaaaa ctgaattcag gatcgtgcca        240
tatttgctca ttttaccgtc gtcttgagca aatatcccat gacaattgag gatcgtgcca        300
tatttgctca ttttaccgtc gtcttgagca aatatcccat gacaattgag gatcgtgcca        360
tatttgctca ttttaccgtc gtcttgagca aatatcccat gacaattgag gatcgtgcca        420
tatttgctca ttttaccgtc gtcttgagca aatatcccat gagaattcag gatcgtgcca        480
tatttgctca ttttaccgtc gtcttgagca aatatcccat gacaattgag gatcgtgcca        540
tatttgctca ttttaccgtc gtcttgagca aatatcccat gacaattgag gatcgtgcca        600
tatttgctca ttttaccgtc gtcttgagca aatatcccat gagaattcag gatcgtgcca        660
tatttgctca ttttaccgtc gtcttgagca aatatcccat gacaattgag gatcgtgcca        720
tatttgctca ttttaccgtc gtcttgagca aatatcccat gacaattgag gatcgtgcca        780
tatttgctca ttttaccgtc gtcttgagca aatatcccat gagaattctt cctgtcttcc        840
tattgattgc agcttccaat tcgtcacac aacaaggtcc tagcgacggc tcacaggttt        900
tgtaacaagc aatcgaaggt tctggaatgg cgggaaaggg tttagtacca catgctatga        960
tgcccactgt gatctccaga gcaaagttcg ttcgatcgta ctgttactct ctctctttca       1020
aacagaattg tccgaatcgt gtgacaacaa cagcctgttc tcacacactc ttttcttcta       1080 accaagggggg tggtttagtt tagtagaacc tcgtgaaact tacatttaca tatatataaa      1140
cttgcataaa ttggtcaatg caagaaatac atatttggtc ttttctaatt cgtagttttt       1200
caagttctta gatgctttct ttttctcttt tttacagatc atcaaggaag taattatcta       1260 cttttttacaa caaatataaa aca                                              1283

<210> SEQ ID NO 75
<211> LENGTH: 686
<212> TYPE: DNA
<213> ORGANISM: Artificial Sequence
<220> FEATURE:
<223> OTHER INFORMATION: pCUR16
<220> FEATURE:
<223> OTHER INFORMATION: pCUR16

<400> SEQUENCE: 75
gctcagcatc tgcttcttcc caaagatgaa cgcggcgtta tgtcactaac gacgtgcacc         60
aacttgcggg aattctcatg ggatatttgc tcaagacgac ggtaaaatga gcaaatatgg        120
cacgatcctc aatgtcatg ggatatttgc tcaagacgac ggtaaaatga gcaaatatgg        180
cacgatcctc aatgtcatgg gatatttgct caagacgacg gtaaaatgag caaatatggc        240
acgatcctga attccaccgc acgccttttt tctgaagccc actttcgtgg actttgccat        300
atatgcaaaa ttcatgaagt gtgataccaa gtcagcatac acctcactag ggtagtttct        360
ttggttgtat tgatcatttg gttcatcgtg gttcattaat ttttttttctc cattgctttc        420 tggctttgat cttactatca tttggatttt tgtcgaaggt tgtagaattg tatgtgacaa        480
gtggcaccaa gcatatataa aaaaaaaaag cattatcttc ctaccagagt tgattgttaa        540
aaacgtattt atagcaaacg caattgtaat taattccttat tttgtatctt tcttcccctt       600
gtctcaatct tttattttta ttttatttttt cttttcttag tttctttcat aacaccaagc       660
aactaatact ataacataca ataata                                             686

<210> SEQ ID NO 76
```

<211> LENGTH: 747
<212> TYPE: DNA
<213> ORGANISM: Artificial Sequence
<220> FEATURE:
<223> OTHER INFORMATION: pCUR17
<220> FEATURE:
<223> OTHER INFORMATION: pCUR17

<400> SEQUENCE: 76

```
gctcagcatc tgcttcttcc caaagatgaa cgcggcgtta tgtcactaac gacgtgcacc    60
aacttgcggg aattctcatg ggatatttgc tcaagacgac ggtaaaatga gcaaatatgg   120
cacgatcctc aattgtcatg ggatatttgc tcaagacgac ggtaaaatga gcaaatatgg   180
cacgatcctc aattctcatg ggatatttgc tcaagacgac ggtaaaatga gcaaatatgg   240
cacgatcctc aattctcatg ggatatttgc tcaagacgac ggtaaaatga gcaaatatgg   300
cacgatcctg aattccaccg cacgcctttt ttctgaagcc cactttcgtg gactttgcca   360
tatatgcaaa attcatgaag tgtgatacca agtcagcata cacctcacta gggtagtttc   420
tttggttgta ttgatcattt ggttcatcgt ggttcattaa ttttttttct ccattgcttt   480
ctggctttga tcttactatc atttggattt tgtcgaagg ttgtagaatt gtatgtgaca    540
agtggcacca agcatatata aaaaaaaaaa gcattatctt cctaccagag ttgattgtta   600
aaaacgtatt tatagcaaac gcaattgtaa ttaattctta ttttgtatct tttcttccct   660
tgtctcaatc ttttattttt attttatttt tcttttctta gtttctttca taacaccaag   720
caactaatac tataacatac aataata                                       747
```

<210> SEQ ID NO 77
<211> LENGTH: 500
<212> TYPE: DNA
<213> ORGANISM: Saccharomyces cerevisiae
<220> FEATURE:
<223> OTHER INFORMATION: pLYS1
<220> FEATURE:
<223> OTHER INFORMATION: pLYS1

<400> SEQUENCE: 77

```
gcaagttaac attagggaga acgtggggcc ttcctccatg agtgcagagc aattgaagat    60
gtttagaggt ttaaaggaga ataaccagtt gctggatagc tctgtgccag ctacagttta   120
tgccaaattg gcccttcatg gtattcctga cggtgttaat ggacagtact tgagctataa   180
tgaccctgcc ttggcggact ttatgccttg aggatagcag gtacatataa attgttacat   240
actaagtcga tgagtcaaaa aagactctta tacatttata catttgcat tattatttt    300
tttttccagc ggaatttgga attccgctct caaccgccaa aattcccctg cgatttcagc   360
gacaaagagt cataaagtca tcctcgagaa accacgatga aatatataaa agcccatct    420
tccctgacgg aaactggtat tttaggaggc ataccataag ataacaacga aaacgcttta   480
tttttcacac aaccgcaaaa                                               500
```

<210> SEQ ID NO 78
<211> LENGTH: 650
<212> TYPE: DNA
<213> ORGANISM: Saccharomyces cerevisiae
<220> FEATURE:
<223> OTHER INFORMATION: pLYS4
<220> FEATURE:
<223> OTHER INFORMATION: pLYS4

<400> SEQUENCE: 78

```
ttgaaaaatg cgaagttgaa gtgccataga agagaaacag cccacacagg ggagaagccc    60
```

```
actggaaagg gggcactgac caactttaaa taggaaacag aagataccac aagccagcga      120
tacaacagca ccaaacaccg aaaagaatag ccaaagctgt cctctggtgt tggaaaaact      180
ggaaaaaacg caactgcgtt ggctgctacg gtgaaaaatt ttcctatgac ttttttcact      240
gcttgttcgt gcgaaattac cgcaaacccg gtaaatgta cacgtatcaa gtgataaaca      300
atttcgtgtc aagtgagcag aatggagcga tttggaaaaa aaaattttt attgtttttt      360 cccccgggat tttgctcgag atgactgaaa ttttgtaatc gatgagtcta taccagaggc      420
agcaaatatc accaacatac acaggtatac acaatctcat gtccacacac acgtacagac      480
acgcacatat atatatatat atatatatcc ccataggtat ttatatatac aaaagaatcc      540
tcgtgtgttt gtgtgtgcaa tagctagttt tgcgctgcct cttatagtag acaatatcac      600
tttttcaata aaatagaact tgcaaggaaa caaaattgta tcgcttcaag                 650

<210> SEQ ID NO 79
<211> LENGTH: 500
<212> TYPE: DNA
<213> ORGANISM: Saccharomyces cerevisiae
<220> FEATURE:
<223> OTHER INFORMATION: pLYS9
<220> FEATURE:
<223> OTHER INFORMATION: pLYS9

<400> SEQUENCE: 79
acatatgcaa gagtcttatg tatcgtatct aagtgccacg taggggattc ccatcatttg       60
atgatttcca aatataatac ctgtagagag cggtggagca aaagtcaaat tttaatcgca      120
actgcagaca agtcaagctg aggaaattgt ggatgatctc ttgtttcttt tgatattcac      180
cacaacagaa gtgaagagtg tgattgcggt tactactgac cacgaagcaa tgcgtttagt      240
agtgaaaaga attactcata ctctggaatc gaaattccgt tggaaaaatt cgctttgtag      300
tgaaaaataa agatgtcaat aaagggtatt gagaatttcc aatggaatta tcagcaatag      360
atgatagaaa gtagcacaga atttggctta atggtatata aaccgtaggg tcctggtaaa      420
attacatggg aaggatcctt aggcagtagg gaaaacttat caggacaatt gagttatatt      480
aacgtattat atattttaat                                                   500

<210> SEQ ID NO 80
<211> LENGTH: 494
<212> TYPE: DNA
<213> ORGANISM: Artificial Sequence
<220> FEATURE:
<223> OTHER INFORMATION: pLYR1p
<220> FEATURE:
<223> OTHER INFORMATION: pLYR1p

<400> SEQUENCE: 80
ttatattgaa ttttcaaaaa ttcttacttt ttttttggat ggacgcaaag aagtttaata       60
atcatattac atggcattac caccatatac atatccatat ctaatcttac ttatatgttg      120
tggaaatgta aagagcccga attcctcata ctctggaatc gaaattccgt tggaaaaatt      180
cgctttgtag tgaaaaataa agatgtcaat aaagggtatt gagaatttcc aatggaatta      240
tcagcaatag atgatagaaa gaattcggat gataatgcga ttagtttttt agccttattt      300
ctggggtaat taatcagcga agcgatgatt tttgatctat taacagatat ataaatggaa      360
aagctgcata accactttaa ctaatacttt caacattttc agtttgtatt acttcttatt      420
caaatgtcat aaaagtatca acaaaaaatt gttaatatac ctctatactt taacgtcaag      480
```
gagaaaaaac tata                                                     494

<210> SEQ ID NO 81
<211> LENGTH: 494
<212> TYPE: DNA
<213> ORGANISM: Artificial Sequence
<220> FEATURE:
<223> OTHER INFORMATION: pLYR2p
<220> FEATURE:
<223> OTHER INFORMATION: pLYR2p

<400> SEQUENCE: 81
ttatattgaa ttttcaaaaa ttcttacttt tttttttggat ggacgcaaag aagtttaata    60
atcatattac atggcattac caccatatac atatccatat ctaatcttac ttatatgttg   120
tggaaatgta aagagcccga attctttcta tcatctattg ctgataattc cattggaaat   180
tctcaatacc ctttattgac atctttatt ttcactacaa agcgaatttt tccaacggaa    240
tttcgattcc agagtatgag gaattcggat gataatgcga ttagtttttt agccttattt   300
ctggggtaat taatcagcga agcgatgatt tttgatctat taacagatat ataaatggaa   360
aagctgcata accactttaa ctaatacttt caacattttc agtttgtatt acttcttatt   420
caaatgtcat aaaagtatca acaaaaaatt gttaatatac ctctatactt taacgtcaag   480
gagaaaaaac tata                                                     494

<210> SEQ ID NO 82
<211> LENGTH: 616
<212> TYPE: DNA
<213> ORGANISM: Artificial Sequence
<220> FEATURE:
<223> OTHER INFORMATION: pLYR3p
<220> FEATURE:
<223> OTHER INFORMATION: pLYR3p

<400> SEQUENCE: 82
ttatattgaa ttttcaaaaa ttcttacttt tttttttggat ggacgcaaag aagtttaata    60
atcatattac atggcattac caccatatac atatccatat ctaatcttac ttatatgttg   120
tggaaatgta aagagcccga attcctcata ctctggaatc gaaattccgt tggaaaaatt   180
cgctttgtag tgaaaaataa agatgtcaat aaagggtatt gagaatttcc aatggaatta   240
tcagcaatag atgatagaaa gaattcctca tactctggaa tcgaaattcc gttggaaaaa   300
ttcgctttgt agtgaaaaat aaagatgtca ataaagggta ttgagaattt ccaatggaat   360
tatcagcaat agatgataga agaattcgg atgataatgc gattagtttt ttagccttat    420
ttctggggta attaatcagc gaagcgatga ttttgatct attaacagat atataaatgg   480
aaaagctgca taaccacttt aactaatact ttcaacattt tcagtttgta ttacttctta   540
ttcaaatgtc ataaaagtat caacaaaaaa ttgttaatat acctctatac tttaacgtca   600
aggagaaaaa actata                                                   616

<210> SEQ ID NO 83
<211> LENGTH: 616
<212> TYPE: DNA
<213> ORGANISM: Artificial Sequence
<220> FEATURE:
<223> OTHER INFORMATION: pLYR4p
<220> FEATURE:
<223> OTHER INFORMATION: pLYR4p

<400> SEQUENCE: 83
ttatattgaa ttttcaaaaa ttcttacttt tttttttggat ggacgcaaag aagtttaata    60

```
atcatattac atggcattac caccatatac atatccatat ctaatcttac ttatatgttg    120
tggaaatgta aagagcccga attctttcta tcatctattg ctgataattc cattggaaat    180
tctcaatacc ctttattgac atctttattt ttcactacaa agcgaatttt tccaacggaa    240
tttcgattcc agagtatgag gaattctttc tatcatctat tgctgataat tccattggaa    300
attctcaata ccctttattg acatctttat ttttcactac aaagcgaatt tttccaacgg    360
aatttcgatt ccagagtatg aggaattcgg atgataatgc gattagtttt ttagccttat    420
ttctggggta attaatcagc gaagcgatga ttttgatct attaacagat atataaatgg    480
aaaagctgca taaccacttt aactaatact ttcaacattt tcagtttgta ttacttctta    540
ttcaaatgtc ataaaagtat caacaaaaaa ttgttaatat acctctatac tttaacgtca    600
aggagaaaaa actata    616

<210> SEQ ID NO 84
<211> LENGTH: 738
<212> TYPE: DNA
<213> ORGANISM: Artificial Sequence
<220> FEATURE:
<223> OTHER INFORMATION: pLYR5p
<220> FEATURE:
<223> OTHER INFORMATION: pLYR5p

<400> SEQUENCE: 84
ttatattgaa ttttcaaaaa ttcttacttt ttttttggat ggacgcaaag aagtttaata    60
atcatattac atggcattac caccatatac atatccatat ctaatcttac ttatatgttg   120
tggaaatgta aagagcccga attctttcta tcatctattg ctgataattc cattggaaat   180
tctcaatacc ctttattgac atctttattt ttcactacaa agcgaatttt tccaacggaa   240
tttcgattcc agagtatgag gaattctttc tatcatctat tgctgataat tccattggaa   300
attctcaata ccctttattg acatctttat ttttcactac aaagcgaatt tttccaacgg   360
aatttcgatt ccagagtatg aggaattctt tctatcatct attgctgata attccattgg   420
aaattctcaa tacccttta tgacatcttt attttcact acaaagcgaa ttttccaac   480 ggaatttcga ttccagagta tgaggaattc ggatgataat gcgattagtt ttttagcctt   540
atttctgggg taattaatca gcgaagcgat gattttgat ctattaacag atatataaat   600
ggaaaagctg cataaccact taactaata ctttcaacat tttcagtttg tattacttct   660
tattcaaatg tcataaaagt atcaacaaaa aattgttaat acctctat actttaacgt   720 caaggagaaa aaactata    738

<210> SEQ ID NO 85
<211> LENGTH: 1104
<212> TYPE: DNA
<213> ORGANISM: Artificial Sequence
<220> FEATURE:
<223> OTHER INFORMATION: pLYR6p
<220> FEATURE:
<223> OTHER INFORMATION: pLYR6p

<400> SEQUENCE: 85
ttatattgaa ttttcaaaaa ttcttacttt ttttttggat ggacgcaaag aagtttaata    60
atcatattac atggcattac caccatatac atatccatat ctaatcttac ttatatgttg   120
tggaaatgta aagagcccga attgctcata ctctggaatc gaaattccgt tggaaaaatt   180
cgctttgtag tgaaaaataa agatgtcaat aaagggtatt gagaatttcc aatggaatta   240
```

```
tcagcaatag atgatagaaa gaattcctca tactctggaa tcgaaattcc gttggaaaaa      300
ttcgctttgt agtgaaaaat aaagatgtca ataaagggta ttgagaattt ccaatggaat      360
tatcagcaat agatgataga agaattcct catactctgg aatcgaaatt ccgttggaaa       420
aattcgcttt gtagtgaaaa ataaagatgt caataaaggg tattgagaat ttccaatgga      480
attatcagca atagatgata gaaacaattg ctcatactct ggaatcgaaa ttccgttgga      540
aaaattcgct ttgtagtgaa aataaagat gtcaataaag ggtattgaga atttccaatg       600
gaattatcag caatagatga tagaaagaat tcctcatact ctggaatcga aattccgttg      660
gaaaaattcg ctttgtagtg aaaaataaag atgtcaataa agggtattga gaatttccaa      720
tggaattatc agcaatagat gatagaaaga attcctcata ctctggaatc gaaattccgt      780
tggaaaaatt cgctttgtag tgaaaaataa agatgtcaat aaagggtatt gagaatttcc      840
aatggaatta tcagcaatag atgatagaaa caattcggat gataatgcga ttagtttttt      900
agccttattt ctggggtaat taatcagcga agcgatgatt tttgatctat taacagatat      960
ataaatggaa aagctgcata accactttaa ctaaactttt caacattttc agtttgtatt     1020
acttcttatt caaatgtcat aaaagtatca acaaaaaatt gttaatatac ctctatactt     1080
taacgtcaag gagaaaaaac tata                                            1104

<210> SEQ ID NO 86
<211> LENGTH: 1836
<212> TYPE: DNA
<213> ORGANISM: Artificial Sequence
<220> FEATURE:
<223> OTHER INFORMATION: pLYR7p
<220> FEATURE:
<223> OTHER INFORMATION: pLYR7p

<400> SEQUENCE: 86
ttatattgaa ttttcaaaaa ttcttacttt tttttggat ggacgcaaag aagtttaata       60
atcatattac atggcattac caccatatac atatccatat ctaatcttac ttatatgttg     120
tggaaatgta aagagcccga attgtttcta tcatctattg ctgataattc cattggaaat     180
tctcaatacc cttattgac atctttattt ttcactacaa agcgaatttt tccaacggaa      240
tttcgattcc agagtatgag gaattcttc tatcatctat tgctgataat tccattggaa      300
attctcaata ccctttattg acatcttat ttttcactac aaagcgaatt tttccaacgg      360
aatttcgatt ccagagtatg aggaattctt tctatcatct attgctgata attccattgg      420
aaattctcaa tacccttat tgacatcttt attttcact acaaagcgaa ttttccaac       480 ggaatttcga ttccagagta tgagcaattg tttctatcat ctattgctga taattccatt     540
ggaaattctc aatacccttt attgacatct ttatttttca ctacaaagcg aatttttcca     600
acggaatttc gattccagag tatgaggaat ctttctatc atctattgct gataattcca      660
ttggaaattc tcaatacccct ttattgacat ctttattttt cactacaaag cgaatttttc     720
caacggaatt tcgattccag agtatgagga attcttctca tcatctattg ctgataattc      780
cattggaaat tctcaatacc cttattgac atctttattt ttcactacaa agcgaatttt      840
tccaacggaa tttcgattcc agagtatgag caattgtttc tatcatctat tgctgataat      900
tccattggaa attctcaata cccttattg acatcttat ttttcactac aaagcgaatt      960
tttccaacgg aatttcgatt ccagagtatg aggaattctt tctatcatct attgctgata     1020
attccattgg aaattctcaa tacccttat tgacatcttt attttcact acaaagcgaa     1080 ttttccaac ggaatttcga ttccagagta tgaggaattc tttctatcat ctattgctga     1140
```

```
taattccatt ggaaattctc aatacccttt attgacatct ttattttca ctacaaagcg    1200 aattttcca acggaatttc gattccagag tatgagcaat tgtttctatc atctattgct    1260
gataattcca ttggaaattc tcaataccct ttattgacat ctttattttt cactacaaag    1320 cgaattttc caacggaatt tcgattccag agtatgagga attctttcta tcatctattg    1380
ctgataattc cattggaaat tctcaatacc ctttattgac atctttattt tcactacaa    1440 agcgaatttt ccaacggaa tttcgattcc agagtatgag gaattctttc tatcatctat    1500
tgctgataat ccattggaa attctcaata ccctttattg acatctttat ttttcactac    1560
aaagcgaatt tttccaacgg aatttcgatt ccagagtatg agcaattcgg atgataatgc    1620
gattagtttt ttagccttat ttctggggta attaatcagc gaagcgatga tttttgatct    1680
attaacagat atataaatgg aaaagctgca taaccacttt aactaatact ttcaacattt    1740
tcagtttgta ttacttctta ttcaaatgtc ataaaagtat caacaaaaaa ttgttaatat    1800
acctctatac tttaacgtca aggagaaaaa actata    1836
```

<210> SEQ ID NO 87
<211> LENGTH: 981
<212> TYPE: DNA
<213> ORGANISM: Artificial Sequence
<220> FEATURE:
<223> OTHER INFORMATION: pLYR8
<220> FEATURE:
<223> OTHER INFORMATION: pLYR8

<400> SEQUENCE: 87

```
ttacattatc aatccttgcg tttcagcttc cactaattta gatgactatt tctcatcatt    60
tgcgtcatct tctaacaccg tatatgataa tatactagta acgtaaatac tagttagtag    120
atgatagttg attttattc caacactaag aaataatttc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tgctcatact ctggaatcga aattccgttg gaaaaattcg ctttgtagtg aaaaataaag    420
atgtcaataa agggtattga gaatttccaa tggaattatc agcaatagat gatagaaaga    480
attcctcata ctctggaatc gaaattccgt tggaaaaatt cgctttgtag tgaaaaataa    540
agatgtcaat aaagggtatt gagaatttcc aatggaatta tcagcaatag atgatagaaa    600
gaattcctca tactctggaa tcgaaattcc gttggaaaaa ttcgctttgt agtgaaaaat    660
aaagatgtca ataagggta ttgagaattt ccaatggaat tatcagcaat agatgataga    720
aacaattcta attaagttag tcaaggcgcc atcctcatga aaactgtgta acataataac    780
cgaagtgtcg aaaaggtggc accttgtcca attgaacacg ctcgatgaaa aaaataagat    840
atatataagg ttaagtaaag cgtctgttag aaaggaagtt tttccttttt cttgctctct    900
tgtcttttca tctactattt ccttcgtgta atacagggtc gtcagataca tagatacaat    960
tctattaccc ccatccatac a    981
```

<210> SEQ ID NO 88
<211> LENGTH: 981
<212> TYPE: DNA
<213> ORGANISM: Artificial Sequence
<220> FEATURE:
<223> OTHER INFORMATION: pLYR9
<220> FEATURE:

<223> OTHER INFORMATION: pLYR9

<400> SEQUENCE: 88

| | | | | | |
|---|---|---|---|---|---|
| ttacattatc | aatccttgcg | tttcagcttc | cactaattta | gatgactatt | tctcatcatt | 60 |
| tgcgtcatct | tctaacaccg | tatatgataa | tatactagta | acgtaaatac | tagttagtag | 120 |
| atgatagttg | attttattc | caacactaag | aaataattc | gccatttctt | gaatgtattt | 180 |
| aaagatattt | aatgctataa | tagacattta | aatccaattc | ttccaacata | caatgggagt | 240 |
| ttggccgagt | ggtttaaggc | gtcagattta | ggtggattta | acctctaaaa | tctctgatat | 300 |
| cttcggatgc | aagggttcga | atcccttagc | tctcattatt | ttttgctttt | tctcttgaat | 360 |
| tgtttctatc | atctattgct | gataattcca | ttggaaattc | tcaataccct | ttattgacat | 420 |
| ctttatttt | cactacaaag | cgaatttttc | caacggaatt | tcgattccag | agtatgagga | 480 |
| attcttctta | tcatctattg | ctgataattc | cattggaaat | tctcaatacc | ctttattgac | 540 |
| atctttattt | ttcactacaa | agcgaatttt | tccaacggaa | tttcgattcc | agagtatgag | 600 |
| gaattcttc | tatcatctat | tgctgataat | tccattggaa | attctcaata | ccctttattg | 660 |
| acatctttat | ttttcactac | aaagcgaatt | tttccaacgg | aatttcgatt | ccagagtatg | 720 |
| agcaattcta | attaagttag | tcaaggcgcc | atcctcatga | aaactgtgta | acataataac | 780 |
| cgaagtgtcg | aaaaggtggc | accttgtcca | attgaacacg | ctcgatgaaa | aaataagat | 840 |
| atatataagg | ttaagtaaag | cgtctgttag | aaaggaagtt | tttccttttt | cttgctctct | 900 |
| tgtcttttca | tctactattt | ccttcgtgta | atacagggtc | gtcagataca | tagatacaat | 960 |
| tctattaccc | ccatccatac | a | | | | 981 |

<210> SEQ ID NO 89
<211> LENGTH: 1225
<212> TYPE: DNA
<213> ORGANISM: Artificial Sequence
<220> FEATURE:
<223> OTHER INFORMATION: pLYR10
<220> FEATURE:
<223> OTHER INFORMATION: pLYR10

<400> SEQUENCE: 89

| | | | | | |
|---|---|---|---|---|---|
| ttacattatc | aatccttgcg | tttcagcttc | cactaattta | gatgactatt | tctcatcatt | 60 |
| tgcgtcatct | tctaacaccg | tatatgataa | tatactagta | acgtaaatac | tagttagtag | 120 |
| atgatagttg | attttattc | caacactaag | aaataattc | gccatttctt | gaatgtattt | 180 |
| aaagatattt | aatgctataa | tagacattta | aatccaattc | ttccaacata | caatgggagt | 240 |
| ttggccgagt | ggtttaaggc | gtcagattta | ggtggattta | acctctaaaa | tctctgatat | 300 |
| cttcggatgc | aagggttcga | atcccttagc | tctcattatt | ttttgctttt | tctcttgaat | 360 |
| tgtttctatc | atctattgct | gataattcca | ttggaaattc | tcaataccct | ttattgacat | 420 |
| ctttatttt | cactacaaag | cgaatttttc | caacggaatt | tcgattccag | agtatgagga | 480 |
| attcttctta | tcatctattg | ctgataattc | cattggaaat | tctcaatacc | ctttattgac | 540 |
| atctttattt | ttcactacaa | agcgaatttt | tccaacggaa | tttcgattcc | agagtatgag | 600 |
| gaattcttc | tatcatctat | tgctgataat | tccattggaa | attctcaata | ccctttattg | 660 |
| acatctttat | ttttcactac | aaagcgaatt | tttccaacgg | aatttcgatt | ccagagtatg | 720 |
| aggaattctt | ctatcatctt | attgctgata | attccattgg | aaattctcaa | tacccttat | 780 |
| tgacatcttt | attttcact | acaaagcgaa | ttttccaac | ggaatttcga | ttccagagta | 840 |
| tgaggaattc | tttctatcat | ctattgctga | taattccatt | ggaaattctc | aataccctt | 900 |

```
attgacatct ttattttca ctacaaagcg aatttttcca acggaatttc gattccagag    960
tatgagcaat tctaattaag ttagtcaagg cgccatcctc atgaaaactg tgtaacataa   1020
taaccgaagt gtcgaaaagg tggcaccttg tccaattgaa cacgctcgat gaaaaaaata   1080
agatatatat aaggttaagt aaagcgtctg ttagaaagga agttttcct ttttcttgct   1140 ctcttgtctt ttcatctact atttccttcg tgtaatacag ggtcgtcaga tacatagata   1200
caattctatt acccccatcc ataca                                        1225
```

<210> SEQ ID NO 90
<211> LENGTH: 1347
<212> TYPE: DNA
<213> ORGANISM: Artificial Sequence
<220> FEATURE:
<223> OTHER INFORMATION: pLYR11
<220> FEATURE:
<223> OTHER INFORMATION: pLYR11

<400> SEQUENCE: 90

```
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataatttc gccatttctt gaatgtattt     180
aaagatattt aatgctataa tagacattta atccaattc ttccaacata caatgggagt     240
ttggccgagt ggtttaaggc gtcagattta ggtggattta acctctaaaa tctctgatat    300
cttcggatgc aagggttcga atcccttagc tctcattatt ttttgctttt tctcttgaat    360
tgctcatact ctggaatcga aattccgttg gaaaaattcg ctttgtagtg aaaaataaag    420
atgtcaataa agggtattga gaatttccaa tggaattatc agcaatagat gatagaaaga    480
attcctcata ctctggaatc gaaattccgt tggaaaaatt cgctttgtag tgaaaaataa    540
agatgtcaat aaagggtatt gagaatttcc aatggaatta tcagcaatag atgatagaaa    600
gaattcctca tactctggaa tcgaaattcc gttggaaaaa ttcgctttgt agtgaaaaat    660
aaagatgtca ataagggta ttgagaattt ccaatggaat tatcagcaat agatgataga    720
aagaattcct catactctgg aatcgaaatt ccgttggaaa aattcgcttt gtagtgaaaa    780
ataaagatgt caataaaggg tattgagaat tccaatgga attatcagca atagatgata    840
gaaagaattc ctcatactct ggaatcgaaa ttccgttgga aaaattcgct ttgtagtgaa    900
aaataaagat gtcaataaag ggtattgaga atttccaatg gaattatcag caatagatga    960
tagaaagaat tcctcatact ctggaatcga aattccgttg gaaaaattcg ctttgtagtg   1020
aaaaataaag atgtcaataa agggtattga gaatttccaa tggaattatc agcaatagat   1080
gatagaaaca attctaatta agttagtcaa ggcgccatcc tcatgaaaac tgtgtaacat   1140
aataaccgaa gtgtcgaaaa ggtggcacct tgtccaattg aacacgctcg atgaaaaaaa   1200
taagatatat ataaggttaa gtaaagcgtc tgttagaaag gaagttttc cttttcttg     1260 ctctcttgtc ttttcatcta ctatttcctt cgtgtaatac agggtcgtca gatacataga   1320
tacaattcta ttacccccat ccataca                                       1347
```

<210> SEQ ID NO 91
<211> LENGTH: 686
<212> TYPE: DNA
<213> ORGANISM: Saccharomyces cerevisiae
<220> FEATURE:
<223> OTHER INFORMATION: pMET17
<220> FEATURE:

<223> OTHER INFORMATION: pMET17

<400> SEQUENCE: 91

| | | | | | |
|---|---|---|---|---|---|
| ttacattatc | aatccttgcg | tttcagcttc | cactaattta | gatgactatt | tctcatcatt | 60 |
| tgcgtcatct | tctaacaccg | tatatgataa | tatactagta | acgtaaatac | tagttagtag | 120 |
| atgatagttg | atttttattc | caacactaag | aaataatttc | gccatttctt | gaatgtattt | 180 |
| aaagatattt | aatgctataa | tagacattta | aatccaattc | ttccaacata | caatgggagt | 240 |
| ttggccgagt | ggtttaaggc | gtcagattta | ggtggattta | acctctaaaa | tctctgatat | 300 |
| cttcggatgc | aagggttcga | atcccttagc | tctcattatt | ttttgctttt | tctcttgagg | 360 |
| tcacatgatc | gcaaaatggc | aaatggcacg | tgaagctgtc | gatattgggg | aactgtggtg | 420 |
| gttggcaaat | gactaattaa | gttagtcaag | gcgccatcct | catgaaaact | gtgtaacata | 480 |
| ataaccgaag | tgtcgaaaag | gtggcacctt | gtccaattga | acacgctcga | tgaaaaaaat | 540 |
| aagatatata | taaggttaag | taaagcgtct | gttagaaagg | aagttttttcc | ttttttcttgc | 600 |
| tctcttgtct | tttcatctac | tatttccttc | gtgtaataca | gggtcgtcag | atacatagat | 660 |
| acaattctat | taccccccatc | cataca | | | | 686 |

<210> SEQ ID NO 92
<211> LENGTH: 510
<212> TYPE: DNA
<213> ORGANISM: Saccharomyces cerevisiae
<220> FEATURE:
<223> OTHER INFORMATION: pMET6
<220> FEATURE:
<223> OTHER INFORMATION: pMET6

<400> SEQUENCE: 92

| | | | | | |
|---|---|---|---|---|---|
| ccacaggaaa | tatttcacgt | gacttacaaa | cagagtcgta | cgtcaggacc | ggagtcaggt | 60 |
| gaaaaatgt | gggccggtaa | agggaaaaaa | ccagaaacgg | gactactatc | gaactcgttt | 120 |
| agtcgcgaac | gtgcaaaagg | ccaatatttt | tcgctagagt | catcgcagtc | atggcagctc | 180 |
| tttcgctcta | tctcccggtc | gcaaaactgt | ggtagtcata | gctcgttctg | ctcaattgag | 240 |
| aactgtgaat | gtgaatatgg | aacaaatgcg | atagatgcac | taatttaagg | gaagctagct | 300 |
| agttttccca | actgcgaaag | aaaaaaagga | agaaaaaaa | aattctatat | aagtgataga | 360 |
| tatttccatc | tttactagca | ttagtttctc | ttttacgtat | tcaatatttt | tgttaaactc | 420 |
| ttcctttatc | ataaaaaagc | aagcatctaa | gagcattgac | aacactctaa | gaaacaaaat | 480 |
| accaatataa | tttcaaagta | catatcaaaa | | | | 510 |

<210> SEQ ID NO 93
<211> LENGTH: 508
<212> TYPE: DNA
<213> ORGANISM: Saccharomyces cerevisiae
<220> FEATURE:
<223> OTHER INFORMATION: pMET14
<220> FEATURE:
<223> OTHER INFORMATION: pMET14

<400> SEQUENCE: 93

| | | | | | |
|---|---|---|---|---|---|
| cctatgcatg | tttagagcaa | gcgcctttgt | gagccctccc | ggttacgacg | ccttggcaat | 60 |
| gtagcagata | actctgcact | tctagaatca | ttccactacg | acatttggct | catcaccagc | 120 |
| tcgcgagaaa | tgtaaataag | ccaacaacca | agaatgcgta | acattaaaga | atacagttgc | 180 |
| tttcatttcg | gcgtgatggt | acggcaccca | cggttcctta | cattattctc | gaaaaatagc | 240 |
| tgcacgcttt | tccaggaata | aaagaccgtg | ccactaattt | cacgtgatca | atatatttac | 300 |

-continued

```
aagccacctc aaaaaatgtg gcaatggaga agaggatgaa cgactcaata tgacttcaac        360
ttcatgaatt tgtcaaaata tctatataag atgcaaaatt tctatacaac atcagttgcg        420
tatccgttaa tgtcgttcat tttctctctt tgttcgaact tgacatcaag aaaagttgga        480
attatttctc caagcacact gtacacca                                           508
```

<210> SEQ ID NO 94
<211> LENGTH: 552
<212> TYPE: DNA
<213> ORGANISM: Saccharomyces cerevisiae
<220> FEATURE:
<223> OTHER INFORMATION: pMET3
<220> FEATURE:
<223> OTHER INFORMATION: pMET3

<400> SEQUENCE: 94

```
aacgatatgt acgtagtggt ataaggtgag ggggtccaca gatataacat cgtttaattt         60
agtactaaca gagacttttg tcacaactac atataagtgt acaaatatag tacagatatg        120
acacacttgt agcgccaacg cgcatcctac ggattgctga cagaaaaaaa ggtcacgtga        180
ccagaaaagt cacgtgtaat tttgtaactc accgcattct agcggtccct gtcgtgcaca        240
ctgcactcaa caccataaac cttagcaacc tccaaaggaa atcaccgtat aacaaagcca        300
cagttttaca acttagtctc ttatgaagtt acttaccaat gagaaataga ggctctttct        360
cgacaaatat gaatatggat atatatatat atatatatat atatatatat atatatatgt        420
aaacttggtt cttttttagc ttgtgatctc tagcttgggt ctctctctgt cgtaacagtt        480
gtgatatcgt ttcttaacaa ttgaaaagga actaagaaag tataataata acaagaataa        540
agtataatta ac                                                           552
```

<210> SEQ ID NO 95
<211> LENGTH: 363
<212> TYPE: DNA
<213> ORGANISM: Saccharomyces cerevisiae
<220> FEATURE:
<223> OTHER INFORMATION: pSAM1
<220> FEATURE:
<223> OTHER INFORMATION: pSAM1

<400> SEQUENCE: 95

```
gaaacggacg taagacggaa atagaatttg aagataaagt tatatatcac tacacacgaa         60
tactttcttt tttttttttc acaggaaaac tgtggtggcg cccttgccta ctagtgcatt        120
tcttttttcg ggttcttgtc tcgacgaaat tttagcctca tcgtagtttt tcactctggt        180
atcgatgaaa aagggaagag taaaaagttt tccgtttagt acttaatggg attggtttgg        240
gacgtatata tcgactggtg ttgtctgtta ttcatcgttg tttttcggtt agcttcgaaa        300
aaaaaataga gtaaaaacca ggaatttacc ctaaaaacaa gaaaaaataa gataaacgaa        360
aat                                                                     363
```

<210> SEQ ID NO 96
<211> LENGTH: 500
<212> TYPE: DNA
<213> ORGANISM: Saccharomyces cerevisiae
<220> FEATURE:
<223> OTHER INFORMATION: pSAM2
<220> FEATURE:
<223> OTHER INFORMATION: pSAM2

<400> SEQUENCE: 96

```
gagctttgct ctattatata agataaaata tgcactaaaa gtttgcattt ctttacataa    60
ctaaaactaa gacattatgc atagcttacc tgatcaaaaa gtatgtaaac ttgttaacat   120
cttcacatgt gattcatctg gtcgtacttt cttgcggtgc agtgtaatat ttctacccac   180
gtgactataa ttgagcttga aaactgtggc gttttttccac cgatgggtcc acgccagata   240
ttaaccgaag ccaaaatacc gatgaaattt ctgagatagc tcttgtaaac gacgtcaaat   300
cttcatatgc aaggagatct tgatttcttt ttggtagtca tctgtcgtct tgaggcgtat   360
aagaaggagg ttatatctgt cctttctaca aagtattttc gagaatcttg cttctgcccc   420 tttttttcttt ttttaaaagg tttaaaaaac ataactgtct tcaatatatc cagtatttac   480
gacaatatac aaacataatc                                              500

<210> SEQ ID NO 97
<211> LENGTH: 300
<212> TYPE: DNA
<213> ORGANISM: Saccharomyces cerevisiae
<220> FEATURE:
<223> OTHER INFORMATION: tTDH2
<220> FEATURE:
<223> OTHER INFORMATION: tTDH2

<400> SEQUENCE: 97
atttaactcc ttaagttact ttaatgattt agttttttatt attaataatt catgctcatg    60
acatctcata tacacgtttta taaaacttaa atagattgaa aatgtattaa agattcctca   120
gggattcgat ttttttggaa gttttttgttt ttttttcctt gagatgctgt agtatttggg   180
aacaattata caatcgaaag atatatgctt acattcgacc gttttagccg tgatcattat   240
cctatagtaa cataacctga agcataactg acactactat catcaatact tgtcacatga   300

<210> SEQ ID NO 98
<211> LENGTH: 300
<212> TYPE: DNA
<213> ORGANISM: Saccharomyces cerevisiae
<220> FEATURE:
<223> OTHER INFORMATION: tCYC1
<220> FEATURE:
<223> OTHER INFORMATION: tCYC1

<400> SEQUENCE: 98
acaggcccct tttcctttgt cgatatcatg taattagtta tgtcacgctt acattcacgc    60
cctcctccca catccgctct aaccgaaaag gaaggagtta gacaacctga agtctaggtc   120
cctatttatt ttttttaata gttatgttag tattaagaac gttatttata ttcaaatttt   180
ttcttttttt tctgtacaaa cgcgtgtacg catgtaacat tatactgaaa accttgcttg   240
agaaggtttt gggacgctcg aaggctttaa tttgcaagct tcgcagttta cactctcatc   300

<210> SEQ ID NO 99
<211> LENGTH: 300
<212> TYPE: DNA
<213> ORGANISM: Saccharomyces cerevisiae
<220> FEATURE:
<223> OTHER INFORMATION: tTDH3
<220> FEATURE:
<223> OTHER INFORMATION: tTDH3

<400> SEQUENCE: 99
gtgaatttac tttaaatctt gcatttaaat aaattttctt tttatagctt tatgacttag    60
tttcaattta tatactattt taatgacatt ttcgattcat tgattgaaag ctttgtgttt   120
tttcttgatg cgctattgca ttgttcttgt cttttttcgcc acatgtaata tctgtagtag   180
```

```
atacctgata cattgtggat gctgagtgaa attttagtta ataatggagg cgctcttaat    240
aattttgggg atattggctt ttttttttaa agtttacaaa tgaatttttt ccgccaggat    300
```

<210> SEQ ID NO 100
<211> LENGTH: 354
<212> TYPE: DNA
<213> ORGANISM: Saccharomyces cerevisiae
<220> FEATURE:
<223> OTHER INFORMATION: tADH1
<220> FEATURE:
<223> OTHER INFORMATION: tADH1

<400> SEQUENCE: 100

```
actagttcta gagcggccgc caccgcggtg ggcgaatttc ttatgattta tgattttat     60 tattaaataa gttataaaaa aaataagtgt atacaaattt taaagtgact cttaggtttt    120
aaaacgaaaa ttcttattct tgagtaactc tttcctgtag gtcaggttgc tttctcaggt    180
atagcatgag gtcgctctta ttgaccacac ctctaccggc atgccagcaa atgcctgca    240 aatcgctccc catttcaccc aattgtagat atgctaactc cagcaatgag ttgatgaatc    300
tcggtgtgta tttatgtcc tcagaggaca acacctgttg taatcgttct tcca          354
```

<210> SEQ ID NO 101
<211> LENGTH: 301
<212> TYPE: DNA
<213> ORGANISM: Saccharomyces cerevisiae
<220> FEATURE:
<223> OTHER INFORMATION: tADH2
<220> FEATURE:
<223> OTHER INFORMATION: tADH2

<400> SEQUENCE: 101

```
gcggatctct tatgtcttta cgatttatag ttttcattat caagtatgcc tatattagta    60
tatagcatct ttagatgaca gtgttcgaag tttcacgaat aaaagataat attctacttt    120
ttgctcccac cgcgtttgct agcacgagtg aacaccatcc ctcgcctgtg agttgtaccc    180
attcctctaa actgtagaca tggtagcttc agcagtgttc gttatgtacg gcatcctcca    240
acaaacagtc ggttatagtt tgtcctgctc ctctgaatcg tctccctcga tatttctcat    300
t                                                                    301
```

<210> SEQ ID NO 102
<211> LENGTH: 299
<212> TYPE: DNA
<213> ORGANISM: Saccharomyces cerevisiae
<220> FEATURE:
<223> OTHER INFORMATION: tTPI1
<220> FEATURE:
<223> OTHER INFORMATION: tTPI1

<400> SEQUENCE: 102

```
gattaatata attatataaa aatattatct tcttttcttt atatctagtg ttatgtaaaa    60
taaattgatg actacggaaa gcttttttat attgtttctt tttcattctg agccacttaa    120
atttcgtgaa tgttcttgta agggacggta gatttacaag tgatacaaca aaaagcaagg    180 cgcttttttct aataaaaaga agaaaagcat ttaacaattg aacacctcta tatcaacgaa    240
gaatattact ttgtctctaa atccttgtaa aatgtgtacg atctctatat gggttactc     299
```

<210> SEQ ID NO 103
<211> LENGTH: 299
<212> TYPE: DNA

<213> ORGANISM: Saccharomyces cerevisiae
<220> FEATURE:
<223> OTHER INFORMATION: tMET17
<220> FEATURE:
<223> OTHER INFORMATION: tMET17

<400> SEQUENCE: 103

```
gtgtgcgtaa tgagttgtaa aattatgtat aaacctactt tctctcacaa gtactatact    60
tttataaaac gaactttatt gaaatgaata tccttttttt cccttgttac atgtcgtgac   120
tcgtactttg aacctaaatt gttctaacat caaagaacag tgttaattcg cagtcgagaa   180
gaaaaatatg gtgaacaaga ctcatctact tcatgagact actttacgcc tcctataaag   240
ctgtcacact ggataaattt attgtaggac caagttacaa aagaggatga tggaggttt    299
```

<210> SEQ ID NO 104
<211> LENGTH: 305
<212> TYPE: DNA
<213> ORGANISM: Saccharomyces cerevisiae
<220> FEATURE:
<223> OTHER INFORMATION: tENO2
<220> FEATURE:
<223> OTHER INFORMATION: tENO2

<400> SEQUENCE: 104

```
ggatcctaaa gtgcttttaa ctaagaatta ttagtctttt ctgcttattt tttcatcata    60
gtttagaaca ctttatatta acgaatagtt tatgaatcta tttaggttta aaaattgata   120 cagtttata agttactttt tcaaagactc gtgctgtcta ttgcataatg cactggaagg   180
ggaaaaaaaa ggtgcacacg cgtggctttt tcttgaattt gcagtttgaa aaataactac   240
atggatgata agaaaacatg gagtacagtc actttgagaa ccttcaatca gctggtaacg   300
tcttc                                                              305
```

<210> SEQ ID NO 105
<211> LENGTH: 300
<212> TYPE: DNA
<213> ORGANISM: Saccharomyces cerevisiae
<220> FEATURE:
<223> OTHER INFORMATION: tMET3
<220> FEATURE:
<223> OTHER INFORMATION: tMET3

<400> SEQUENCE: 105

```
tcgtcataaa atgctcccat ctcaaaagta gggcaaaatt catgatcgac cgcgcaaaat    60
aaatagattt gcaaataagt tttgtatgta catttattaa tatatataat atatcaaaag   120
aaaaaaatca aaaaaaaaaa aaaaaaaaaa ttgcactctt attcagtcat caattacaaa   180
acctagagat agcgatggtg catattcaat aaaaaactcc ttatactgtc gagaaagctt   240
attattggta cttctcgaag atactaaaaa aggttaattt ttggagacgg aggcaatagc   300
```

<210> SEQ ID NO 106
<211> LENGTH: 301
<212> TYPE: DNA
<213> ORGANISM: Saccharomyces cerevisiae
<220> FEATURE:
<223> OTHER INFORMATION: tPGK1
<220> FEATURE:
<223> OTHER INFORMATION: tPGK1

<400> SEQUENCE: 106

```
attgaattga attgaaatcg atagatcaat ttttttcttt tctctttccc catcctttac    60
gctaaaataa tagtttattt tattttttga atatttttta tttatatacg tatatataga   120
```

```
ctattattta tcttttaatg attattaaga tttttattaa aaaaaaattc gctcctcttt    180
taatgccttt atgcagtttt tttttcccat tcgatatttc tatgttcggg ttcagcgtat    240
tttaagttta ataactcgaa aattctgcgt tcgttaaagc tttcgagaag gatattattt    300
a                                                                   301

<210> SEQ ID NO 107
<211> LENGTH: 300
<212> TYPE: DNA
<213> ORGANISM: Saccharomyces cerevisiae
<220> FEATURE:
<223> OTHER INFORMATION: tDIT1
<220> FEATURE:
<223> OTHER INFORMATION: tDIT1

<400> SEQUENCE: 107
taaagtaaga gcgctacatt ggtctacctt tttgttcttt tacttaaaca ttagttagtt     60
cgttttcttt ttctcatttt tttatgtttc cccccaaag ttctgatttt ataatatttt    120
atttcacaca attccattta acagaggggg aatagattct ttagcttaga aaattagtga   180
tcaatatata tttgcctttc ttttcatctt ttcagtgata ttaatggttt cgagacactg   240
caatggccct agttgtctaa gaggatagat gttactgtca aagatgatat tttgaatttc   300

<210> SEQ ID NO 108
<211> LENGTH: 300
<212> TYPE: DNA
<213> ORGANISM: Saccharomyces cerevisiae
<220> FEATURE:
<223> OTHER INFORMATION: tRPL3
<220> FEATURE:
<223> OTHER INFORMATION: tRPL3

<400> SEQUENCE: 108
gaagttttgt tagaaaataa atcatttttt aattgagcat tcttattcct attttattta    60
aatagtttta tgtattgtta gctacataca acagtttaaa tcaaattttc ttttcccaa   120 gtccaaaatg gaggtttatt ttgatgaccc gcatgcgatt atgttttgaa agtataagac   180
tacatacatg tacatatatt taaacatgta aacccgtcca ttatattgct tactttcttc   240 tttttgccg ttttgacttg gacctctggt ttgctatttc cttacaatct tgctacaat    300

<210> SEQ ID NO 109
<211> LENGTH: 300
<212> TYPE: DNA
<213> ORGANISM: Saccharomyces cerevisiae
<220> FEATURE:
<223> OTHER INFORMATION: tRPL41B
<220> FEATURE:
<223> OTHER INFORMATION: tRPL41B

<400> SEQUENCE: 109
gcggattgag agcaaatcgt taagttcagg tcaagtaaaa attgatttcg aaaactaatt    60
tctcttatac aatcctttga ttggaccgtc atcctttcga atataagatt tgttaagaa   120 tattttagac agagatctac tttatattta atatctagat attacataat ttcctctcta   180
ataaaatatc attaataaaa taaaaatgaa gcgatttgat tttgtgttgt caacttagtt   240
tgccgctatg cctcttgggt aatgctatta ttgaatcgaa gggctttatt atattaccct   300

<210> SEQ ID NO 110
<211> LENGTH: 300
<212> TYPE: DNA
```

<213> ORGANISM: Saccharomyces cerevisiae
<220> FEATURE:
<223> OTHER INFORMATION: tRPL15A
<220> FEATURE:
<223> OTHER INFORMATION: tRPL15A

<400> SEQUENCE: 110

| | | | | | |
|---|---|---|---|---|---|
| gctggttgat | ggaaaatata | attttattgg | gcaaacttt | gtttatctga | tgtgttttat | 60 |
| actattatct | ttttaattaa | tgattctata | tacaaacctg | tatatttttt | ctttaaccaa | 120 |
| ttttttttt | tatagaccta | gagctgtact | tttattctgc | tatcaagcaa | accoctaccc | 180 |
| cctcttctca | atcctcccct | caggcagaac | ttatctacct | gtatcaagga | gcggacgagg | 240 |
| gagtcctaat | tgttctacgt | ataccaatgc | tagcagctta | cataggtggt | ggcactacca | 300 |

<210> SEQ ID NO 111
<211> LENGTH: 300
<212> TYPE: DNA
<213> ORGANISM: Saccharomyces cerevisiae
<220> FEATURE:
<223> OTHER INFORMATION: tIDP1
<220> FEATURE:
<223> OTHER INFORMATION: tIDP1

<400> SEQUENCE: 111

| | | | | | |
|---|---|---|---|---|---|
| tcgaatttac | gtagcccaat | ctaccacttt | tttttttcat | tttttaaagt | gttatactta | 60 |
| gttatgctct | aggataatga | actactttt | tttttttttt | tttactgtta | tcataaatat | 120 |
| atatacctta | tgttgtttg | caaccgtcgg | ttaattcctt | atcaaggttc | cccaagttcg | 180 |
| gatcattacc | atcaatttcc | aacattttca | tgagttcttc | ttcttcatta | ccgtgtttta | 240 |
| gggggctgtt | cgcacttcta | atagggctat | caccaagctg | ttctaattcg | tccaaaagtt | 300 |

<210> SEQ ID NO 112
<211> LENGTH: 1089
<212> TYPE: DNA
<213> ORGANISM: Kluveromyces lactis
<220> FEATURE:
<223> OTHER INFORMATION: Leu2
<220> FEATURE:
<223> OTHER INFORMATION: Leu2

<400> SEQUENCE: 112

| | | | | | |
|---|---|---|---|---|---|
| atgtctaaga | atatcgttgt | cctaccgggt | gatcacgtcg | gtaaagaagt | tactgacgaa | 60 |
| gctattaagg | tcttgaatgc | cattgctgaa | gtccgtccag | aaattaagtt | caatttccaa | 120 |
| catcacttga | tcggggtgc | tgccatcgat | gccactggca | ctcctttacc | agatgaagct | 180 |
| ctagaagcct | ctaagaaagc | cgatgctgtc | ttactaggtg | ctgttggtgg | tccaaaatgg | 240 |
| ggtacgggcg | cagttagacc | agaacaaggt | ctattgaaga | tcagaaagga | attgggtcta | 300 |
| tacgccaact | tgagaccatg | taactttgct | tctgattctt | tactagatct | ttctcctttg | 360 |
| aagcctgaat | atgcaagggg | taccgatttc | gtcgtcgtta | gagaattggt | tggtggtatc | 420 |
| tactttggtg | aaagaaaaga | agatgaaggt | gacggagttg | cttgggactc | tgagaaatac | 480 |
| agtgttcctg | aagttcaaag | aattacaaga | atggctgctt | tcttggcatt | gcaacaaaac | 540 |
| ccaccattac | caatctggtc | tcttgacaag | gctaacgtgc | ttgcctcttc | agattgtgg | 600 |
| agaaagactg | ttgaagaaac | catcaagact | gagttccac | aattaactgt | tcagcaccaa | 660 |
| ttgatcgact | ctgctgctat | gattttggtt | aaatcaccaa | ctaagctaaa | cggtgttgtt | 720 |
| attaccaaca | acatgtttgg | tgatattatc | tccgatgaag | cctctgttat | tccaggttct | 780 |
| ttgggtttat | accttctgc | atctctagct | tccctacctg | acactaacaa | ggcattcggt | 840 |

```
ttgtacgaac catgtcatgg ttctgcccca gatttaccag caaacaaggt taacccaatt    900
gctaccatct tatctgcagc tatgatgttg aagttatcct tggatttggt tgaagaaggt    960
agggctcttg aagaagctgt tagaaatgtc ttggatgcag gtgtcagaac cggtgacctt   1020
ggtggttcta actctaccac tgaggttggc gatgctatcg ccaaggctgt caaggaaatc   1080
ttggcttaa                                                           1089
```

<210> SEQ ID NO 113
<211> LENGTH: 362
<212> TYPE: PRT
<213> ORGANISM: Kluveromyces lactis
<220> FEATURE:
<223> OTHER INFORMATION: Leu2
<220> FEATURE:
<223> OTHER INFORMATION: Leu2

<400> SEQUENCE: 113

```
Met Ser Lys Asn Ile Val Val Leu Pro Gly Asp His Val Gly Lys Glu
1               5                   10                  15

Val Thr Asp Glu Ala Ile Lys Val Leu Asn Ala Ile Ala Glu Val Arg
            20                  25                  30

Pro Glu Ile Lys Phe Asn Phe Gln His His Leu Ile Gly Gly Ala Ala
        35                  40                  45

Ile Asp Ala Thr Gly Thr Pro Leu Pro Asp Glu Ala Leu Glu Ala Ser
    50                  55                  60

Lys Lys Ala Asp Ala Val Leu Leu Gly Ala Val Gly Gly Pro Lys Trp
65                  70                  75                  80

Gly Thr Gly Ala Val Arg Pro Glu Gln Gly Leu Leu Lys Ile Arg Lys
                85                  90                  95

Glu Leu Gly Leu Tyr Ala Asn Leu Arg Pro Cys Asn Phe Ala Ser Asp
            100                 105                 110

Ser Leu Leu Asp Leu Ser Pro Leu Lys Pro Glu Tyr Ala Lys Gly Thr
        115                 120                 125

Asp Phe Val Val Val Arg Glu Leu Val Gly Gly Ile Tyr Phe Gly Glu
    130                 135                 140

Arg Lys Glu Asp Glu Gly Asp Gly Val Ala Trp Asp Ser Glu Lys Tyr
145                 150                 155                 160

Ser Val Pro Glu Val Gln Arg Ile Thr Arg Met Ala Ala Phe Leu Ala
                165                 170                 175

Leu Gln Gln Asn Pro Pro Leu Pro Ile Trp Ser Leu Asp Lys Ala Asn
            180                 185                 190

Val Leu Ala Ser Ser Arg Leu Trp Arg Lys Thr Val Glu Glu Thr Ile
        195                 200                 205

Lys Thr Glu Phe Pro Gln Leu Thr Val Gln His Gln Leu Ile Asp Ser
    210                 215                 220

Ala Ala Met Ile Leu Val Lys Ser Pro Thr Lys Leu Asn Gly Val Val
225                 230                 235                 240

Ile Thr Asn Asn Met Phe Gly Asp Ile Ile Ser Asp Glu Ala Ser Val
                245                 250                 255

Ile Pro Gly Ser Leu Gly Leu Leu Pro Ser Ala Ser Leu Ala Ser Leu
            260                 265                 270

Pro Asp Thr Asn Lys Ala Phe Gly Leu Tyr Glu Pro Cys His Gly Ser
        275                 280                 285

Ala Pro Asp Leu Pro Ala Asn Lys Val Asn Pro Ile Ala Thr Ile Leu
    290                 295                 300
```

```
Ser Ala Ala Met Met Leu Lys Leu Ser Leu Asp Leu Val Glu Glu Gly
305                 310                 315                 320

Arg Ala Leu Glu Glu Ala Val Arg Asn Val Leu Asp Ala Gly Val Arg
            325                 330                 335

Thr Gly Asp Leu Gly Gly Ser Asn Ser Thr Thr Glu Val Gly Asp Ala
        340                 345                 350

Ile Ala Lys Ala Val Lys Glu Ile Leu Ala
        355                 360

<210> SEQ ID NO 114
<211> LENGTH: 499
<212> TYPE: DNA
<213> ORGANISM: Saccharomyces cerevisiae
<220> FEATURE:
<223> OTHER INFORMATION: pNUP57
<220> FEATURE:
<223> OTHER INFORMATION: pNUP57

<400> SEQUENCE: 114
tcatctgcgc aatgactatc aagaccttct gcaagaattt caaatctcac tgaaaatctt      60
gaccgaaaag tgtcttgaaa acccatcaag cctgcaaaac ctatctttga cattagtctc     120
cattataaaa acggcatagt tgggagaaaa cttttcatac ttcaattgtg gactgatata     180
agtattttgg ttttgcccgc atgatcatcc cacatggcta cagcagttct ctcataggaa     240
atagtacaat agctacgtga tataatctaa ataattgttg ccaatgtgta attatatcat     300
tttgaacgtt cgcgaaatgg attattttca aaaattttgt ttcttgaaat gagtaaaagc     360
aaaagtccaa ctctccaagt cgatgtaaac aacttttgc caagggact gaaagactaa       420 atcgaggatt atcccgttca aactattcca gaaacgctcg ttagtaacaa aagcatacc      480 ttgttgacca attgatcac                                                   499

<210> SEQ ID NO 115
<211> LENGTH: 451
<212> TYPE: DNA
<213> ORGANISM: Saccharomyces cerevisiae
<220> FEATURE:
<223> OTHER INFORMATION: pGAP1
<220> FEATURE:
<223> OTHER INFORMATION: pGAP1

<400> SEQUENCE: 115
cactttcacc agatcccaaa tgtcccgccc ctattcccgt gttccatcac gtaccataac      60
ttaccatttc atcacgttct ctatggcaca ctggtactgc ttcgactgct ttgcttcatc     120
ttctctatgg gccaatgagc taatgagcac aatgtgctgc gaaataaagg gatatctaat     180
ttatattatt acattataat atgtactagt gtggttattg gtaattgtac ttaattttga     240
tatataaagg gtggatcttt tcattttga atcagaattg gaattgcaac ttgtctcttg      300
tcactattac ttaatagtaa ttatatttct tattaacctt ttttttaagt caaaacacca     360
aggacaagaa ctactcttca aaggtatttc aagttatcat acgtctcaca cacgcttcac     420
agtttcaagt aaaaaaaaag aatattacac a                                    451

<210> SEQ ID NO 116
<211> LENGTH: 998
<212> TYPE: DNA
<213> ORGANISM: Saccharomyces cerevisiae
<220> FEATURE:
<223> OTHER INFORMATION: pJEN1
<220> FEATURE:
```

<223> OTHER INFORMATION: pJEN1

<400> SEQUENCE: 116

```
aatgtgttta taaattattt tttttgctgg tagcaaaatc aactcattgt cttccattca    60
gagtctaatc gaacgttatc gcaatgcttg cacacttta aacaatacga tttagtttaa   120
gtggatggac ccccacgctt agtgttccac aggtttgtcc ccactgtttt tacattccac   180
tgtacatttt tgcaatagaa ggtcattgta tgctaccttg ggcggctaag aatacctgta   240
aaaatttgga gaaattagat tcgtaaagaa tgactcgcaa cgactccaat gatttcttct   300
tttcacccctt tgaacggccg atatccgcgc gggatcctga ccccgcaatt tactccacta   360
gaccggcgtg tttctctttt tccttttcct ggggttagag cccaagagct aatagccgac   420
aaacggactc caaaaaaaaa aggaggcaca ggacaaacgc agcacctgcg tcattcacgc   480
tgaagcggca gcaagcattt tcgatcagct ccaattaaat gaagactatt cgccgtaccg   540
ttcccagatg ggtgcgaaag tcagtgatcg aggaagttat tgagcgcgcg gcttgaaact   600
atttctccat ctcagagccg ccaagcctac cattattctc caccaggaag ttagtttgta   660
agcttctgca caccatccgg acgtccataa ttcttcactt aacggtcttt tgcccccccct   720
tctactataa tgcattagaa cgttacctgg tcatttggat ggagatctaa gtaacactta   780
ctatctccta tggtactatc ctttaccaaa aaaaaaaaaa aaaaaaaaaa aaaaaatcag   840
caaagtgaag taccctcttg atgtataaat acattgcaca tcattgttga gaaatagttt   900
tggaagttgt ctagtccttc tcccttagat ctaaaaggaa gaagagtaac agtttcaaaa   960
gtttttcctc aaagagatta aatactgcta ctgaaaat                          998
```

<210> SEQ ID NO 117
<211> LENGTH: 450
<212> TYPE: DNA
<213> ORGANISM: Saccharomyces cerevisiae
<220> FEATURE:
<223> OTHER INFORMATION: pICL1
<220> FEATURE:
<223> OTHER INFORMATION: pICL1

<400> SEQUENCE: 117

```
ttttgctact cgtcatccga tgagaaaaac tgttcccttt tgccccaggt ttccattcat    60
ccgagcgatc acttatctga cttcgtcact ttttcatttc atccgaaaca atcaaaactg   120
aagccaatca ccacaaaatt aacactcaac gtcatctttc actacccttt acagaagaaa   180
atatccatag tccggactag catcccagta tgtgactcaa tattggtgca aaagagaaaa   240
gcataagtca gtccaaagtc cgcccttaac caggcacatc ggaattcaca aaacgtttct   300
ttattatata aaggagctgc ttcactggca aaattcttat tatttgtctt ggcttgctaa   360
tttcatctta tccttttttt cttttcacac ccaaatacct aacaattgag agaaaactct   420
tagcataaca taacaaaaag tcaacgaaaa                                    450
```

<210> SEQ ID NO 118
<211> LENGTH: 598
<212> TYPE: DNA
<213> ORGANISM: Saccharomyces cerevisiae
<220> FEATURE:
<223> OTHER INFORMATION: pADH2
<220> FEATURE:
<223> OTHER INFORMATION: pADH2

<400> SEQUENCE: 118

```
tatcttaact gatagtttga tcaaaggggc aaaacgtagg ggcaaacaaa cggaaaaatc    60
```

```
gtttctcaaa ttttctgatg ccaagaactc taaccagtct tatctaaaaa ttgccttatg    120
atccgtctct ccggttacag cctgtgtaac tgattaatcc tgcctttcta atcaccattc    180
taatgtttta attaagggat tttgtcttca ttaacggctt tcgctcataa aaatgttatg    240
acgttttgcc cgcaggcggg aaaccatcca cttcacgaga ctgatctcct ctgccggaac    300
accgggcatc tccaacttat aagttggaga aataagagaa tttcagattg agagaatgaa    360
aaaaaaaaaa aaaaaaggca gaggagagca tagaaatggg gttcactttt tggtaaagct    420
atagcatgcc tatcacatat aaatagagtg ccagtagcga cttttttcac actcgaaata    480
ctcttactac tgctctcttg ttgttttttat cacttcttgt ttcttcttgg taaatagaat    540
atcaagctac aaaaagcata caatcaacta tcaactatta actatatcgt aatacaca     598

<210> SEQ ID NO 119
<211> LENGTH: 793
<212> TYPE: DNA
<213> ORGANISM: Saccharomyces cerevisiae
<220> FEATURE:
<223> OTHER INFORMATION: pMLS1
<220> FEATURE:
<223> OTHER INFORMATION: pMLS1

<400> SEQUENCE: 119
tgtctaatgc gaaggtactt ttattttttt cagattcaaa gcaatattat ttagacaatt     60
gatactaagt gagcttaagg aggattaaac aactgtggaa tccttcacaa ggattcaata    120
tttgtttttc ctggttattt tgccatcatt caactttcct cagacgtaaa attcgtgctt    180
agtgatgtct caatattccc gcagggtaat aaaattcaat aactatcact atatacgcaa    240
cagtattacc ctacattgct atcggctcaa tggaaatccc catatcatag cttccattgg    300
gccgatgaag ttagtcgacg gatagaagcg gttgtcccct ttcccggcga gccggcagtc    360
gggccgaggt tcggataaat tttgtattgt gttttgattc tgtcatgagt attacttatg    420
ttctctttag gtaacccccag gttaatcaat cacagtttca taccggctag tattcaaatt    480
atgacttttc ttctgcagtg tcagccttac gacgattatc tatgagcttt gaatatagtt    540
tgccgtgatt cgtatcttta attggataat aaaatgcgaa ggatcgatga cccttattat    600
tatttttcta cactggctac cgatttaact catcttcttg aaagtatata agtaacagta    660
aaatataccg tacttctgct aatgttattt gtcccttatt tttcttttct tgtcttatgc    720
tatagtacct aagaataacg actattgttt tgaactaaac aaagtagtaa aagcacataa    780
aagaattaag aaa                                                       793
```

THREONINE-PRODUCING YEAST

FIELD OF THE INVENTION

The present invention relates to the field of bio-production of threonine.

BACKGROUND OF THE INVENTION

Threonine, or L-threonine, is an essential amino acid that is widely used as an additive to animal fodder and food, and as fluids and synthetic materials for medical and pharmaceutical use.

Together with Serine, Asparagine, and Glutamine, Threonine is one of the uncharged polar amino acids and is essential in the metabolism of numerous living organisms, including non-human and human mammals.

Most plants, fungi and bacteria can synthesize threonine from carbohydrates sources. However, animals, including humans, depend on externally provided threonine sources.

Threonine can be found in high concentrations in the heart, the skeletal muscles and the central nervous system and is important in the formation of many proteins, collagen, elastrin and tooth enamel. Threonine helps to maintain a proper protein balance in the body and also helps preventing the build up of fat in the liver. Threonine is also highly interesting in that it supports digestive function by protecting the digestive tract, as it is needed to produce the mucus veering it. Threonine thus helps preventing indigestion and ulcers.

It has also been demonstrated that threonine supports the immune system as it is used to produce antibodies in the thymus.

Moreover, as threonine is used by the body to produce other amino acids, i.e. serine and glycine, a sufficient absorption of threonine is highly important to also generate these two essential amino acids. In particular, serine and glycine are important for the production of collagen in the organism. It is well known that collagen is of high importance in all non-human and human mammals' organisms.

Chemically produced threonine can be used for most applications. However, against the background of decreasing fossil resources and the stronger environmental constraints (e.g. hazardous intermediates and waste), alternative and more sustainable processes based on natural resources are gaining more and more interest. Further, there is a general search for cost-saving sources of threonine for a plurality of industrial applications.

Threonine may be produced by non-synthetic processes by enzymatic conversion or fermentation starting from precursor compounds, such as for example sugar (such as glucose), aspartate or homoserine. However, because the precursors are often chemically synthesized or have to be produced in a first step by fermentation, there is no real industrial or financial advantage over the processes of chemical synthesis. Illustrative embodiments of processes for producing and purifying threonine by fermentation methods are for example disclosed in the U.S. Pat. Nos. 3,375,173 and 4,996,147.

Production of threonine by fermentation from natural sources may solve many of the above-mentioned problems. There are numerous bacteria and yeasts which are able to overproduce amino acids under adequate conditions. However, because of the very complex regulation of the L-threonine syntheses, only a few strains are able to produce economically relevant amounts of threonine. Thus, the main drawback of producing threonine by a fermentation process is the very complex biosynthesis of threonine with manifold feedback inhibition (Chassagnol et al. (2001); Biochem. J. (356) 433-444).

In all cases, candidate threonine producer organisms have to undergo numerous rounds of mutation and selection before being retained as relevant producers. Illustrative embodiments of candidate threonine-producing microorganisms selected after spontaneous mutation or chemically-induced mutagenesis are disclosed in the US patent application no. US 20090093030 as well as in the U.S. Pat. No. 8,852,898.

The production of essential amino acids such as threonine through the biosynthetic pathways of bacteria and yeasts requires an important amount of reducing power in the form of NADPH. However, the main pathway for the metabolisation of glucose in these microorganisms, and in particular in yeasts, is glycolysis followed by fermentation which only produces NADH. Maintaining an appropriate NADPH/NADH balance within the microorganism, albeit complex, is therefore essential to optimize bio-production of threonine while obtaining a viable recombinant microorganism.

The major known bacterial amino acid producer is *C. glutanicum*, a gram-positive, facultative anaerobic, non-pathogenic soil bacterium. *C. glutanicum* is used for the large-scale industrial production of the flavor enhancer L-glutamate as well as of the food additive L-lysine. Various attempts have been performed for producing threonine by fermentation of *C. glutanicum* as illustrated in Palmieri et al. Arch Microbiol (1996) 165: 48.

According to other improvement strategies, an increase in threonine production by fermentation has been explored through genetic engineering of candidate microorganisms, mainly the bacterial organism *E. coli*. Illustrating embodiments are disclosed in the in Kwang Ho Lee et al. (Mol Syst Biol. 2007; 3: 149).

There is still a need in the art for further threonine production methods.

SUMMARY OF THE INVENTION

The present invention accordingly relates to a threonine-producing recombinant yeast, in the genome of which:

(A) at least one nucleic acid encoding an aspartate semi-aldehyde dehydrogenase and/or at least one nucleic acid encoding an aspartate semi-aldehyde dehydrogenase that can use as coenzyme both NAD and NADP is overexpressed and/or is under the control of an inducible or repressible promoter;

(B) at least one nucleic acid encoding an homoserine kinase is overexpressed and/or is under the control of an inducible or repressible promoter;

(C) at least one nucleic acid encoding a threonine synthase is overexpressed and/or is under the control of an inducible or repressible promoter; and (D) (i) at least one nucleic acid encoding an aspartokinase is under the control of an inducible or repressible promoter; and/or (ii) at least one nucleic acid encoding an aspartate kinase is overexpressed and/or is under the control of an inducible or repressible promoter.

As illustrated in the enclosed examples, the recombinant yeasts of the invention have an increased threonine production compared to non-recombinant or native strains.

Said advantageous property can be further increased by also recombining the yeast with additional modifications described here-after.

A threonine-producing recombinant yeast can consequently advantageously be used in a method for producing threonine as described here-after or be used for the production of threonine.

The present invention further relates to a method for producing threonine, said method comprising the steps of:
(a) culturing a recombinant yeast according to the invention in a culture medium; and
(b) recovering the threonine from said culture medium.

In a preferred embodiment, the culture medium comprises at least a carbon source, preferably a carbon source selected from the group consisting of glucose and sucrose.

The invention further relates to the use of a recombinant yeast according to the invention for the production of threonine.

DETAILED DESCRIPTION OF THE INVENTION

The inventors have conceived genetically modified microorganisms, and especially genetically modified yeasts, having an increased ability to produce threonine, as compared to the parent microorganisms, and especially as compared to the parent yeasts.

These genetically modified microorganisms, including these genetically modified yeasts, are described throughout the present specification.

Definitions

The term "microorganism", as used herein, refers to a yeast which is not modified artificially. The microorganism may be "donor" if it provides genetic element to be integrated in the microorganism "acceptor" which will express this foreign genetic element or if it used as tool for genetic constructions or protein expressions. The microorganism of the invention is chosen among yeast which expresses genes for the biosynthesis of threonine.

The term "recombinant microorganism" or "genetically modified microorganism" or "recombinant yeast" or "genetically modified yeast", as used herein, refers to a yeast genetically modified or genetically engineered. It means, according to the usual meaning of these terms, that the microorganism of the invention is not found in nature and is modified either by introduction or by deletion or by modification of genetic elements from equivalent microorganism found in nature. It can also be modified by forcing the development and evolution of new metabolic pathways by combining directed mutagenesis and evolution under specific selection pressure (see for instance WO 2004/076659).

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganism, like yeast, with exogenous DNA is a routine task for those skilled in the art. In particular, a genetic modification of a microorganism according to the invention, more particularly the genetic modification(s) herein defined, may be carried out by using CRISPR-Cas systems, as described in DiCarlo et al. (Nucl. Acids Res., vol. 41, No. 7, 2013: 4336-4343).

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, in the down-regulation and/or attenuation of the activity of the endogenous gene product. Another way to enhance expression of endogenous genes is to introduce one or more supplementary copies of the gene onto the chromosome or a plasmid.

The term "exogenous gene" means that the gene was introduced into a microorganism, by means well known by the man skilled in the art, whereas this gene is not naturally occurring in the wild-type microorganism. Microorganism can express exogenous genes if these genes are introduced into the microorganism with all the elements allowing their expression in the host microorganism. Transforming microorganisms with exogenous DNA is a routine task for the man skilled in the art. Exogenous genes may be integrated into the host chromosome, or be expressed extra-chromosomally from plasmids or vectors. A variety of plasmids, which differ with respect to their origin of replication and their copy number in the cell, are all known in the art. The sequence of exogenous genes may be adapted for its expression in the host microorganism. Indeed, the man skilled in the art knows the notion of codon usage bias and how to adapt nucleic sequences for a particular codon usage bias without modifying the deduced protein.

The term "heterologous gene" means that the gene is derived from a species of microorganism different from the recipient microorganism that expresses it. It refers to a gene which is not naturally occurring in the microorganism.

In the present application, all genes are referenced with their common names and with references to their nucleotide sequences and, the case arising, to their amino acid sequences. Using the references given in accession number for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerated probes to clone the corresponding gene in another organism.

The man skilled in the art knows different means to modulate, and in particular up-regulate or down-regulate, the expression of endogenous genes. For example, a way to enhance expression of endogenous genes is to introduce one or more supplementary copies of the gene onto the chromosome or a plasmid.

Another way is to replace the endogenous promoter of a gene with a stronger promoter. These promoters may be homologous or heterologous. Promoters particularly interesting in the present invention are described in more detail elsewhere in the present specification.

The nucleic acid expression construct may further comprise 5' and/or 3' recognition sequences and/or selection markers.

The term "overexpression" means that the expression of a gene or of an enzyme is increased as compared to the non-modified microorganism. Increasing the expression of an enzyme is obtained by increasing the expression of a gene encoding said enzyme. Increasing the expression of a gene may be carried out by all techniques known by the one skilled in the art. In this regard, it may be notably cited the implementation of a strong promoter upstream the nucleic acid intended to be overexpressed or the introduction of a plurality of copies of the said nucleic acid between a promoter, especially a strong promoter, and a terminator.

The term "underexpression" means that the expression of a gene or of an enzyme is decreased as compared to the non-modified microorganism. Decreasing the expression of an enzyme is obtained by decreasing the expression of a gene encoding said enzyme. Decreasing the expression of a gene may be carried out by all techniques known by the one skilled in the art. In this regard, it may be notably cited the implementation of a weak promoter upstream the nucleic acid intended to be underexpressed. It may be also cited the implementation of a nucleic acid encoding a variant of the said enzyme that is less active than the parent enzyme or a variant of the said enzyme that is more rapidly degraded in the cell than the parent enzyme. Variants of a parent enzyme that is more rapidly degraded that the said parent enzyme encompass degron-tagged enzymes. It may also be cited the decrease of the expression of a transcription activator of the gene of interest.

The term "inducible promoter" is used to qualify a promoter whose activity is induced, i.e. increased:
  in the presence of one or more particular metabolite(s). The higher the metabolite concentration in the medium, the stronger the promoter activity; or
  in the presence of a low concentration, or in the absence, of one or more metabolite(s). These metabolites are different from those whose increasing presence induces the activity of the promoter. The lower the metabolite concentration in the medium, the stronger the promoter activity.

The term "repressible promoter" is used to qualify a promoter whose activity is repressed, i.e. reduced:
  in the presence of one or more particular metabolite(s). The higher the metabolite concentration in the medium, the weaker the promoter activity; or
  in the presence of a low concentration, or in the absence, of one or more metabolite(s). These metabolites are different from those whose increasing presence represses the activity of the promoter. The lower the metabolite concentration in the medium, the weaker the promoter activity.

A used herein, a "degron-tagged" enzyme means an enzyme comprising an added protein-degradation signal amino acid sequence that serves as a destruction signal that will cause the said enzyme to be the subject of a degradation, which may be either (i) a ubiquitin-independent degradation or (ii) an ubiquitin-dependent degradation. The said added protein-degradation signal, that is also termed "degron" in the art, encompasses an amino acid sequence that serves as a destruction signal, the said amino acid sequence consisting of a transferrable degradation signal causing a targeted protein degradation. Degrons encompass "N-degrons", which are transferrable N-terminal amino acids that cause the target protein degradation following the well known N-end rule (Bachmair et al., 1986, Science, Vol. 234 (4773): 179-186). The unstable nature of the N-degron is attributed to its first amino acids, which are prone to acetylation or arginylation modifications and ultimately lead to ubiquitination and degradation. Generally, a degron requires at least two components to ensure targeted protein degradation: (i) a target degradation recognition tag, such as a poly-ubiquitin tag and (ii) an unstructured amino acid sequence in close proximity to the degradation recognition tag. For degron-tagging a protein, and especially herein for degron-tagging an enzyme, the one skilled in the art may refer to Yu et al. (2015, Current Opinion in Biotechnology, Vol. 36: 199-204), Cho et al. (2010, Genes & Development, Vol. 24: 438-442), or to Fortmann et al. (2015, J Mol Biol, Vol. 427 (17): 2748-2756), Ravid et al. (2008, Nat Rev Mol Cell Biol, Vol. 9(9): 679-690) and Hochstrasser (1996, Annu Rev Genet, Vol. 30: 405-439).

The "activity" of an enzyme is used interchangeably with the term "function" and designates, in the context of the invention, the capacity of an enzyme to catalyze a desired reaction.

The terms "reduced activity" or "attenuated activity" of an enzyme mean either a reduced specific catalytic activity of the protein obtained by mutation in the amino acids sequence and/or decreased concentrations of the protein in the cell obtained by mutation of the nucleotide sequence or by deletion of the cognate corresponding gene or also by degron-tagging of the protein.

The term "enhanced activity" of an enzyme designates either an increased specific catalytic activity of the enzyme, and/or an increased quantity/availability of the enzyme in the cell, obtained for example by overexpression of the gene encoding the enzyme.

The terms "encoding" or "coding" refer to the process by which a polynucleotide, through the mechanisms of transcription and translation, produces an amino-acid sequence.

The gene(s) encoding the enzyme(s) considered in the present invention can be exogenous or endogenous.

"Attenuation" of genes means that genes are expressed at an inferior rate than in the non modified microorganism. The attenuation may be achieved by means and methods known to the man skilled in the art and contains gene deletion obtained by homologous recombination, gene attenuation by insertion of an external element into the gene or gene expression under a weak promoter. The man skilled in the art knows a variety of promoters which exhibit different strengths and which promoter to use for a weak genetic expression.

The methods implemented in the present invention preferably require the use of one or more chromosomal integration constructs for the stable introduction of a heterologous nucleotide sequence into a specific location on a chromosome or for the functional disruption of one or more target genes in a genetically modified microbial cell. In some embodiments, disruption of the target gene prevents the expression of the related functional protein. In some embodiments, disruption of the target gene results in the expression of a non-functional protein from the disrupted gene.

Parameters of chromosomal integration constructs that may be varied in the practice of the present invention include, but are not limited to, the lengths of the homologous sequences; the nucleotide sequence of the homologous sequences; the length of the integrating sequence; the nucleotide sequence of the integrating sequence; and the nucleotide sequence of the target locus. In some embodiments, an effective range for the length of each homologous sequence is 20 to 5,000 base pairs, preferentially 50 to 100 base pairs. In particular embodiments, the length of each homologous sequence is about 50 base pairs. For more information on the length of homology required for gene targeting, see D. Burke et al., Methods in yeast Genetics—A cold spring harbor laboratory course Manual (2000).

In some embodiments, (a) disrupted gene(s) in which the above-mentioned DNA construct(s) is/are intended to be inserted may advantageously comprise one or more selectable markers useful for the selection of transformed microbial cells. Preferably, said selectable marker(s) are comprised in the DNA construct(s) according to the present invention.

In some embodiments, the selectable marker is an antibiotic resistance marker. Illustrative examples of antibiotic resistance markers include, but are not limited to the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Auerobasidin A (AbA); the HPH gene product of *Klebsiella pneumonia* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin).

In some embodiments, the antibiotic resistance marker is deleted after the genetically modified microbial cell of the invention is isolated. The man skilled in the art is able to choose suitable marker in specific genetic context.

In some embodiments, the selectable marker rescues an auxotrophy (e.g., a nutritional auxotrophy) in the genetically modified microbial cell. In such embodiments, a parent microbial cell comprises a functional disruption in one or more gene products that function in an amino acid or nucleotide biosynthetic pathway, such as, for example, the HIS3, LEU2, LYS1, LYS2, MET 15, TRP1, ADE2, and URA3 gene products in yeast, which renders the parent microbial cell incapable of growing in media without supplementation with one or more nutrients (auxotrophic phenotype). The auxotrophic phenotype can then be rescued by transforming the parent microbial cell with a chromosomal integration encoding a functional copy of the disrupted gene product (NB: the functional copy of the gene can originate from close species, such as *Kluveromyces, Candida* etc.), and the genetically modified microbial cell generated can be selected for based on the loss of the auxotrophic phenotype of the parent microbial cell.

For each of the nucleic acid sequences comprising a promoter sequence, a coding sequence (e.g. an enzyme coding sequence), or a terminator sequence, reference sequences are described herein. The present description also encompasses nucleic acid sequences having specific percentages of nucleic acid identity, with a reference nucleic acid sequence.

For each or the amino acid sequences of interest, reference sequences are described herein. The present description also encompasses amino acid sequences (e.g. enzyme amino acid sequences), having specific percentages of amino acid identity, with a reference amino acid sequence.

For obvious reasons, in all the present description, a specific nucleic acid sequence or a specific amino acid sequence which complies with, respectively, the considered nucleotide or amino acid identity, should further lead to obtaining a protein (or enzyme) which displays the desired biological activity. As used herein, the "percentage of identity" between two nucleic acid sequences or between two amino acid sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The identity percentage is calculated by determining the number of positions at which an identical nucleic base, or an identical amino-acid residue, can be noted for both compared sequences, then by dividing the number of positions at which identity can be observed between both nucleic bases, or between both amino-acid residues, by the total number of positions in the comparison window, then by multiplying the result by hundred to obtain the percentage of nucleotide identity between the two sequences or the percentage of amino acid identity between the two sequences.

The comparison of the sequence optimal alignment may be performed by a computer using known algorithms.

Most preferably, the sequence identity percentage is determined using the CLUSTAL W software (version 1.82) the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

The "fermentation" or "culture" is generally conducted in fermenters with an appropriate culture medium adapted to the microorganism being cultivated, containing at least one simple carbon source, and if necessary co-substrates.

Microorganisms disclosed herein may be grown in fermentation media for the production of a product from oxaloacetate. For maximal production of threonine, the microorganism strains used as production hosts preferably have a high rate of carbohydrate utilization. These characteristics may be conferred by mutagenesis and selection, genetic engineering, or may be natural. Fermentation media, or "culture medium", for the present cells may contain at least about 10 g/L of glucose. Additional carbon substrates may include but are not limited to monosaccharides such as fructose, mannose, xylose and arabinose; oligosaccharides such as lactose maltose, galactose, or sucrose; polysaccharides such as starch or cellulose or mixtures thereof and unpurified mixtures from renewable feedstocks such as cheese whey permeate cornsteep liquor, sugar beet molasses, and barley malt. Other carbon substrates may include glycerol.

Hence, it is contemplated that the source of carbon utilized in the present invention may encompass a wide variety of carbon containing substrates and will only be limited by the choice of organism.

Although it is contemplated that all of the above-mentioned carbon substrates and mixtures thereof are suitable in the present invention, preferred carbon substrates are glucose, fructose, and sucrose, or mixtures of these with C5 sugars such as xylose and/or arabinose for microorganisms modified to use C5 sugars, and more particularly glucose.

A preferred carbon substrate is glucose.

In addition to an appropriate carbon source, fermentation media may contain suitable minerals, salts, cofactors, buffers and other components, known to those skilled in the art, suitable for the growth of the cultures and promotion of the enzymatic pathway necessary for the production of the desired product.

Besides, additional genetic modifications suitable for the growth of recombinant microorganisms according to the invention may be considered.

The terms "Aerobic conditions" refers to concentrations of oxygen in the culture medium that are sufficient for an aerobic or facultative anaerobic microorganism to use dioxygene as a terminal electron acceptor.

"Microaerobic condition" refers to a culture medium in which the concentration of oxygen is less than that in air, i.e. oxygen concentration up to 6% $O_2$.

An "appropriate culture medium" designates a medium (e.g. a sterile, liquid medium) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like. The term "carbon source" or "carbon substrate" or "source of carbon" according to the present invention denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

General Features of Genetic Modifications Introduced According to the Invention

Genes are over expressed by two kinds of non mutually exclusive modifications:
Placing them under the control of a strong promoter; and/or
Inserting a plurality of copies of the considered gene.
All the genome modifications are inserted in yeast according to known genetic engineering techniques;
The successive genes included in a gene construct that is introduced in the yeast genome according to the invention are of the following structure:
$Prom_1$-$ORF_1$-$term_1$-$ORF_2$-$gene_2$-$term_2$- . . . / . . . -$Prom_n$-$ORF_n$-$term_n$, wherein:
$Prom_1$ is a sequence regulating the expression of the coding sequence ORF1,
ORF1 is a nucleic acid sequence encoding a desired protein PROT1, and especially a desired enzyme PROT1,
$Term_1$ is a transcription terminator sequence that mediates transcriptional termination by providing signals in the newly synthesized mRNA that trigger processes which release the mRNA from the transcriptional complex, and
"1", "2", . . . / . . . "n" may or may not describe the same ORF (Open Reading Frame), promoter or terminator. The order of the genes does not matter. "n" is an integer usually ranging from 5 and 20. These constructs are inserted in one of the yeast chromosome at a controlled location. In some embodiments, the insertion site is not essential for the functionality of the inserted construct, nor for the viability of the resulting genetically modified yeast.
When the yeast is for example *Saccharomyces cerevisiae*, genes introduced in the yeast genome and originating from other organisms than *Saccharomyces cerevisiae* are generally "transcoded" (generally codon-optimized"), meaning that these genes are synthesized with an optimal codon usage for expression *S. cerevisiae*. The nucleotide sequence (and not the protein sequence) of some genes from *S. cerevisiae* has also been modified ("transcoded") to minimize recombination with an endogenous copy of the said gene.

Genes may be deleted through standard procedures used in yeast genetic engineering. In some embodiments, the genes targeted for deletion may be interrupted by insertion of one of the above described gene constructs, or alternatively the genes targeted for deletion are replaced by a short stretch of nucleotide.

Down regulating gene expression may be obtained by disrupting the endogenous copy of the gene and replacing it with a copy of the ORF under the control of a weak promoter. A list and sequences of weak promoters is described elsewhere in the present specification.

A gene may be rendered "inducible or repressible" by deleting the endogenous copy of the gene (if necessary) and placing a new copy of the ORF under the control of an inducible or repressible promoter. An inducible or repressible promoter is a promoter which activity is modulated and controlled, i.e. either increased or decreased, upon a change in the environmental conditions or external stimuli. Induction or repression may be artificially controlled, which encompasses induction or repression by abiotic factors such as chemical compounds not found naturally in the organism of interest, light, oxygen levels, heat or cold. A list and sequence of inducible or repressible promoters is described elsewhere in the present specification.

As already specified elsewhere herein, a protein may be underexpressed by destabilization by using "the degron" technology which is described in Yu et al. 2015 (Current Opinion in Biotechnology, Vol. 36: 199-204). In brief this technology consists in introducing in the protein sequence a modification that targets it for degradation. It can consist only in the two first amino acids following the principle known as the N-end rule, or a larger sequence targeting the whole protein to the ubiquitin-preoteasome degradation pathway.

Recombinant Yeast According to the Invention

The inventors have conceived recombinant microorganisms, and especially recombinant yeasts, having an increased ability of producing threonine.

The present invention relates to recombinant yeasts having an increased threonine production, and wherein the increased threonine production is obtained through a plurality of alterations that have been introduced in the genome thereof, by genetic engineering methods.

This invention pertains to a threonine-producing recombinant yeast, in the genome of which:

(A) at least one nucleic acid encoding an aspartate semi-aldehyde dehydrogenase HOM2 and/or at least one nucleic acid encoding an aspartate semi-aldehyde dehydrogenase HOM2 that can use as coenzyme both NAD and NADP is overexpressed and/or is under the control of an inducible or repressible promoter;

(B) at least one nucleic acid encoding an homoserine kinase THR1 is overexpressed and/or is under the control of an inducible or repressible promoter;

(C) at least one nucleic acid encoding a threonine synthase THR4 is overexpressed and/or is under the control of an inducible or repressible promoter; and (D) (i) at least one nucleic acid encoding an aspartokinase HOM3 is under the control of an inducible or repressible promoter; and/or (ii) at least one nucleic acid encoding an aspartate kinase AK is overexpressed and/or is under the control of an inducible or repressible promoter.

The inventors have found that an increased production of threonine by yeast cells may be reached by introducing in the genome of these yeast cells a plurality of genetic alterations. As it is fully described herein, the said plurality of genetic alterations encompass an overexpression of certain genes, a controlled expression of certain other genes, as well as repression or deletion of further other genes.

The increased threonine production by yeast cells has been reached by the inventors by optimizing the metabolism of oxaloacetate, so as to direct the subsequent artificially modified metabolic pathway mainly towards threonine production whereas in the same time maintaining an optimal viability of the resulting genetically modified yeast cells.

After a lengthy research time period, the present inventors have determined that a high threonine production by yeast cells is obtained by increasing the conversion of oxaloacetate into the successive intermediate metabolites aspartate, phospho-aspartyl, aspartyl-semialdehyde, homoserine and phospho-homoserine, and additionally enhancing the conversion of phospho-homoserine into threonine, while, notably, maintaining a redox status allowing a good viability of the resulting recombinant yeast cells. This last point is essential and represented a significant challenge for the inventors throughout their research work.

The proposed solution according to the invention unexpectedly allows maintaining a viable NADH/NADPH equilibrium in the yeast cells throughout the threonine-production pathway through the consumption of less reducing power, the consumption of reducing power in the form of NADH rather than NADPH, and/or the production of NADH instead of NADPH.

As disclosed in detail in the present specification, the resulting recombinant yeast cells are genetically modified so as (I) to effect an over expression and/or a controlled expression of an aspartate semialdehyde dehydrogenase-encoding gene (HOM2), of an homoserine kinase (THR1) and of a threonine synthase (THR4), and (II) to effect a controlled expression of an aspartokinase-encoding gene (HOM3) and/or an over expression and/or a controlled expression of an aspartate kinase (AK).

Further, in some embodiments of a recombinant yeast according to the invention, the said yeast comprise further genetic modifications for an optimal use of the intermediate metabolite aspartyl-semialdehyde for threonine production, the said further genetic modifications comprising an over expression and/or a controlled expression of (i) an aspartate transaminase (AAT2), (ii) of a glutamate dehydrogenase (GDH) that converts oxo-glutarate to glutamate, an over expression of (iii) an homoserine dehydrogenase (HOME) and an over expression (iv) of a probable transporter (AQR1).

In some embodiments of a recombinant yeast according to the invention, the said yeast comprises alternative further genetic modifications for threonine production, the said further genetic modifications comprising:

A. a) the deletion of at least one, preferably all, endogenous nucleic acid encoding an homoserine-O-acetyltransferase (MET2), or b) the repression of at least one, preferably all, nucleic acid encoding an homoserine-O-acetyltransferase (MET2) and/or the fact that at least one, preferably all, the nucleic acid encoding an homoserine-O-acetyltransferase (MET2) is in a destabilized form;

and/or

B. a) the deletion of at least one, preferably all, endogenous nucleic acid encoding a methionine synthase (MET17), or b) the repression of at least one, preferably all, nucleic acid encoding a methionine synthase (MET17) and/or the fact that at least one, preferably all, the nucleic acid encoding a methionine synthase (MET17) is in a destabilized form.

A recombinant yeast according to the invention produces threonine with a higher yield than the parent yeast which does not contain the genetic modifications described above.

A recombinant yeast according to the invention has been genetically engineered so as to promote the expression of enzymes utilizing NADH rather than NADPH, such as an appropriate glutamate dehydrogenase or an appropriate aspartate semialdehyde dehydrogenase.

In some embodiments of a recombinant yeast according to the invention, the aspartate-semialdehyde dehydrogenase that are overexpressed consist of the *S. cerevisiae* endogenous gene that is placed under the control of strong promoters and/or of inducible or repressible promoters.

In some embodiments, the aspartate-semialdehyde dehydrogenase is preferably encoded by the *S. cerevisiae* HOM2 gene.

In some embodiments, the aspartate-semialdehyde dehydrogenase is most preferably encoded by a variant of the *S. cerevisiae* HOM2 gene, which genes codes for a mutated HOM2 protein that uses both NAD and NADP, as it is shown in the examples herein. Such gene variant is for example illustrated in the examples and is called HOM2-2. It corresponds to the *S. cerevisiae* HOM2 gene mutated as discussed here-under.

The nature of the mutations aiming several amino acid residues in the aspartate semialdehyde dehydrogenase variant in order to relax the high selectivity of HOM2 for NADP as coenzyme and enhance the affinity of the enzyme for NAD are known to the man skilled in the art and can for example be found in Faehnle, C. R. et al., Journal of Molecular Biology 1055-1068 (2005). In particular, the mutation S39 to E39 corresponding to the replacement of the nucleotides TCT in position 115 to 117 of the nucleotide sequence by the nucleotides GAG can be mentioned.

According to the nomenclature of the amino acids well known to the man skilled in the art, S represents a Serine and E represents a Glutamic acid.

In some embodiments, the aspartokinase is most preferably encoded by the *S. cerevisiae* HOM3 gene, as it is shown in the examples herein.

Further, the controlled expression of the aspartokinase expression is achieved by placing the aspartokinase-encoding nucleic acid under the control of an inducible or repressible promoter. Illustrative inducible or repressible promoters that may be used for obtaining a recombinant threonine-producing yeast according to the invention are described elsewhere in the present specification.

Illustratively, in the embodiments wherein the said inducible or repressible promoter is pCUP1-1 promoter originating from *S. cerevisiae*, the expression of the aspartokinase may be induced by adding copper to the culture medium. The one skilled in the art may notably refer to Koller et al. (2000, Yeast, Vol. 16: 651-656).

Aspartate-Semialdehyde Dehydrogenase-Encoding Gene Over Expression and/or Controlled Expression In preferred embodiments of a recombinant yeast according to the invention, over expression of an aspartate-semialdehyde dehydrogenase-encoding gene is obtained by inserting, at selected location(s) of the yeast genome, one or more copies of an expression cassette comprising an aspartate-semialdehyde dehydrogenase coding sequence. Aspartate-semialdehyde dehydrogenase and an aspartate-semialdehyde dehydrogenase-encoding gene that are encompassed by the invention are detailed elsewhere in the present specification.

In some of these embodiments, the said one or more copies of an expression cassette comprising an aspartate-semialdehyde dehydrogenase (HOM2) coding sequence comprise(s) regulatory sequences allowing a strong expression of the aspartate-semialdehyde dehydrogenase, such as a strong promoter that is functional in yeast cells.

In addition to or as an alternative to these embodiments of a recombinant yeast according to the invention, at least one aspartate-semialdehyde dehydrogenase-encoding gene can be under the control of an inducible or repressible promoter that is functional in yeast cells.

Without wishing to be bound by any particular theory, the inventors believe that over expression of an aspartate-semialdehyde dehydrogenase may enhance the conversion of the intermediate metabolite aspartyl phosphate (Aspartyl-P) into aspartyl-semialdehyde. The same applies when at least one aspartate-semialdehyde dehydrogenase coding sequence is under the control of an inducible or repressible promoter.

In some embodiments, the aspartate-semialdehyde dehydrogenase may be an enzyme variant that uses either NADH or NADPH for catalyzing the conversion of aspartyl phosphate (Aspartyl-P) into aspartyl-semialdehyde.

In some preferred embodiments, the said aspartate-semialdehyde dehydrogenase-encoding gene is the gene from *Saccharomyces cerevisiae*, or alternatively a variant utilizing both NADH and NADPH as shown in the examples herein and discussed previously.

In preferred embodiments, the said aspartate semi-aldehyde dehydrogenase-encoding gene is placed under the control of the strong promoter pADH1, of the strong promoter pTEF1, the inducible or repressible promoter pCUP1-1, the inducible or repressible promoter pACU8 or the inducible or repressible promoter pACU5, in particular the inducible or repressible promoter pACU5.

Illustratively, the aspartate-semialdehyde dehydrogenase gene may be inserted within the HOM3 gene and/or within the PYK2 gene and/or within the MUP3 gene and/or within the SAM1 gene and/or whitin the SAM2 gene and/or within the HIS3 gene, preferably within the HIS3 gene as shown in the examples herein.

Homoserine Kinase-Encoding Gene Over Expression and/or Controlled Expression

In preferred embodiments of a recombinant yeast according to the invention, over expression of a homoserine kinase-encoding gene is obtained by inserting, at selected location(s) of the yeast genome, one or more copies of an expression cassette comprising a homoserine kinase coding sequence. Homoserine kinase (THR1) and a homoserine kinase-encoding gene that are encompassed by the invention are detailed elsewhere in the present specification.

In some of these embodiments, the said one or more copies of an expression cassette comprising a homoserine kinase-coding sequence comprise regulatory sequences allowing a strong expression of the homoserine kinase, such as a strong promoter that is functional in yeast cells.

In addition to or as an alternative to these embodiments of a recombinant yeast according to the invention, at least one homoserine kinase-encoding gene can be under the control of an inducible or repressible promoter that is functional in yeast cells.

Without wishing to be bound by any particular theory, the inventors believe that an over expression of a homoserine kinase increases the conversion of the intermediate metabolite into phospho-homoserine. The same applies when at least one homoserine kinase coding sequence is under the control of an inducible or repressible promoter.

In preferred embodiments, the said homoserine kinase-encoding gene is the gene from *Saccharomyces cerevisiae*, as shown in the examples herein.

In preferred embodiments, the said homoserine kinase-encoding gene is placed under the control of the strong promoter pTDH3 or the inducible or repressible promoter pACU6, preferably under the control of the strong promoter pTDH3.

Illustratively, the homoserine kinase gene may be inserted within the SAM3 gene, as it is shown in the examples herein.
Threonine Synthase-Encoding Gene Over Expression and/or Controlled Expression In preferred embodiments of a recombinant yeast according to the invention, over expression of a threonine synthase-encoding gene is obtained by inserting, at selected location(s) of the yeast genome, one or more copies of an expression cassette comprising a threonine synthase coding sequence. Threonine synthase (THR4) and a threonine synthase-encoding gene that are encompassed by the invention are detailed elsewhere in the present specification.

In some of these embodiments, the said one or more copies of an expression cassette comprising a threonine synthase-coding sequence comprise regulatory sequences allowing a strong expression of the threonine synthase, such as a strong promoter that is functional in yeast cells.

In addition to or as an alternative to these embodiments of a recombinant yeast according to the invention, at least one threonine synthase-encoding gene can be under the control of an inducible or repressible promoter that is functional in yeast cells.

Without wishing to be bound by any particular theory, the inventors believe that an over expression of a threonine synthase increases the conversion of the intermediate metabolite into threonine. The same applies when at least one threonine synthase coding sequence is under the control of an inducible or repressible promoter.

In preferred embodiments, the said threonine synthase-encoding gene is the gene from *Saccharomyces cerevisiae*, as shown in the examples herein.

In preferred embodiments, the said threonine synthase-encoding gene is placed under the control of the strong promoter pTDH3, of the inducible or repressible promoter pACU6 or of the strong promoter pCCW12, preferably under the control of the strong promoter pCCW12.

Illustratively, the threonine synthase gene may be inserted within the SAM3 gene, as it is shown in the examples herein.
Controlled Expression of an Aspartokinase-Encoding Gene Aspartokinase and an aspartokinase-encoding gene that are encompassed by the invention are detailed elsewhere in the present specification.

Without wishing to be bound by any particular theory, the inventors believe that with a controlled expression of an aspartokinase-encoding gene, a controlled level of conversion of aspartate into aspartyl phosphate (Aspartyl-P) is obtained that shall contribute to the high level of viability of a recombinant yeast according to the invention.

In some embodiments of a recombinant yeast according to the invention, a controlled expression of an aspartokinase-encoding gene is obtained by inserting, at selected location(s) of the yeast genome, one or more copies of an expression cassette comprising an aspartokinase (HOM3)

coding sequence that is placed under the control of an inducible regulatory element, such as an inducible or repressible promoter.

In some embodiments, a controlled expression of an aspartokinase-encoding gene is obtained by inserting, at the location of the natural yeast aspartokinase open reading frame, an inducible regulatory sequence, such as an inducible or repressible promoter, that replaces the endogenous promoter initially present in the yeast genome at this genome location.

In some preferred embodiments, the said aspartokinase-encoding gene is the gene from *Saccharomyces cerevisiae*, as shown in the examples herein.

In preferred embodiments, the said aspartokinase-encoding gene is placed under the control of the inducible or repressible promoter pCUP-1-1, of the inducible or repressible promoter pSAM4 or of the inducible or repressible promoter pACU3p.

Illustratively, the aspartokinase gene may be inserted within the TRP1 gene and/or within the HOM3 gene and/or within the MUP3 gene and/or within the SAM3 gene.

Aspartate Kinase-Encoding Gene Over Expression and/or Controlled Expression

In preferred embodiments of a recombinant yeast according to the invention, over expression of an aspartate kinase-encoding gene is obtained by inserting, at selected location(s) of the yeast genome, one or more copies of an expression cassette comprising a aspartate kinase coding sequence. Aspartate kinase (AK) and an aspartate kinase-encoding gene that are encompassed by the invention are detailed elsewhere in the present specification.

In some of these embodiments, the said one or more copies of an expression cassette comprising an aspartate kinase-coding sequence comprise regulatory sequences allowing a strong expression of the aspartate kinase, such as a strong promoter that is functional in yeast cells.

In addition to or as an alternative to these embodiments of a recombinant yeast according to the invention, at least one aspartate kinase-encoding gene can be under the control of an inducible or repressible promoter that is functional in yeast cells.

Without wishing to be bound by any particular theory, the inventors believe that with a controlled expression of an aspartate kinase-encoding gene, a controlled level of conversion of aspartate into aspartyl phosphate (Aspartyl-P) is obtained that shall contribute to the high level of viability of a recombinant yeast according to the invention.

In preferred embodiments, the said aspartate kinase-encoding gene is the gene from *Bacillus subtilis*, as shown in the examples herein.

In preferred embodiments, the said aspartate kinase-encoding gene is placed under the control of the inducible or repressible promoter pACU7.

Illustratively, the aspartate kinase gene may be inserted within the TRP1 gene, as it is shown in the examples herein.

As indicated previously, the genome of a threonine-producing recombinant yeast according to the invention is such that:

(i) at least one nucleic acid encoding an aspartokinase HOM3 is under the control of an inducible or repressible promoter; and/or (ii) at least one nucleic acid encoding an aspartate kinase AK is overexpressed and/or is under the control of an inducible or repressible promoter.

In a preferred embodiment, the genome of a threonine-producing recombinant yeast according to the invention is such that at least one nucleic acid encoding an aspartokinase HOM3 is under the control of an inducible or repressible promoter.

In another preferred embodiment, the genome of a threonine-producing recombinant yeast according to the invention is such that at least one nucleic acid encoding an aspartate kinase AK is overexpressed and/or is under the control of an inducible or repressible promoter.

A description of the genes encoding (i) an aspartate semialdehyde dehydrogenase, (ii) an homoserine kinase, (iii) a threonine synthase, (iv) an aspartokinase and (v) an aspartate kinase is found hereunder.

Aspartate Semialdehyde Dehydrogenase (HOM2)

The aspartate-semialdehyde dehydrogenase is a protein which is known in the art to catalyze the NADPH-dependent formation of L-aspartate-semialdehyde by the reductive dephosphorylation of L-aspartyl-4-phosphate. The aspartate-semialdehyde dehydrogenase encoded by the genome of *Saccharomyces cerevisiae* may be termed HOM2.

A method implemented to measure the activity level of aspartate-semialdehyde dehydrogenase belongs to the general knowledge of the one skilled in the art.

Preferred aspartate semialdehyde-dehydrogenase in the present specification is an enzyme having an EC number 1.2.1.11.

According to a preferred embodiment, the nucleic acid(s) encoding an aspartate-semialdehyde dehydrogenase may be nucleic acid(s) originating from organisms preferably selected in a group comprising prokaryotic organisms and eukaryotic organisms. In some embodiments, the nucleic acid(s) encoding an aspartate-semialdehyde dehydrogenase may be nucleic acid(s) originating from archaebacteria. In some preferred embodiments, the nucleic acid(s) encoding an aspartate semialdehyde dehydrogenase may be nucleic acid(s) originating from yeast, and especially from *Saccharomyces cerevisiae*.

According to other preferred embodiment, the nucleic acid encoding an aspartate semialdehyde dehydrogenase may be a variant or a mutant of the aspartate semialdehyde dehydrogenase from *Saccharomyces cerevisiae*, wherein the said variant enzyme or the said mutant enzyme uses either NADH or NADPH for catalyzing reactions. Such variant or mutant enzymes are known in the art and are previously discussed in the present text.

According to a yet preferred embodiment, the nucleic acid(s) encoding an aspartate-semialdehyde dehydrogenase may be nucleic acid(s) selected from the group consisting of sequences having at least 27%, advantageously at least 65%, preferably at least 80%, nucleic acid identity with a nucleic acid selected in a group consisting of the reference nucleic acid sequences of SEQ ID NO: 1 and SEQ ID NO. 2, and also a biological activity of the same nature. The nucleic acids of SEQ ID NO: 1 and SEQ ID NO. 2 encode an aspartate-semialdehyde dehydrogenase originating from *Saccharomyces cerevisiae*.

A biological activity of the same nature regarding this sequence is the capacity to code for an enzyme that catalyzes the NADPH-dependent formation of L-aspartate-semialdehyde by the reductive dephosphorylation of L-aspartyl-4-phosphate.

As described herein, a nucleic acid sequence having at least 27% nucleotide identity with a reference nucleic acid sequence encompasses nucleic acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the aspartate-semialdehyde dehydrogenase from *Saccharomyces cerevisiae*, the one skilled in the art may refer to the accession number NP010442 in the UniProt database, or to SEQ ID NO. 3 described herein.

According to another particular embodiment, the nucleic acid(s) encoding an aspartate-semialdehyde dehydrogenase may be nucleic acid(s) encoding an amino acid sequence selected from the group consisting of sequences having at least 27%, advantageously at least 65%, preferably at least 80%, amino acid identity with the amino acid sequence of SEQ ID NO: 3, and also a biological activity of the same nature. Illustratively, the aspartate-semialdehyde dehydrogenase originating from *Lactobacillus wasatchensis* has 27% amino acid identity with the aspartate-semialdehyde dehydrogenase of SEQ ID NO. 3.

A biological activity of the same nature regarding this sequence is as described previously, i.e. the capacity to catalyze the NADPH-dependent formation of L-aspartate-semialdehyde by the reductive dephosphorylation of L-aspartyl-4-phosphate.

As described herein, an amino acid sequence having at least 27% amino acid identity with a reference nucleic acid sequence encompasses amino acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the aspartate-semialdehyde dehydrogenase in the present invention is regulated by at least one promoter and at least one terminator, such as herein after defined more in details, which are present in 5' and 3' position respectively of the nucleic acid sequence encoding the said aspartate-semialdehyde dehydrogenase.

As it is specified elsewhere in the present description, the aspartate-semialdehyde dehydrogenase is overexpressed and/or under the control of an inducible or repressible promoter in a recombinant yeast according to the invention.

In some embodiments, overexpression of the aspartate-semialdehyde dehydrogenase may result from the control of the corresponding gene by a strong promoter within the said recombinant yeast.

In some other embodiments, overexpression of the aspartate-semialdehyde dehydrogenase may result from the presence of a plurality of copies of a aspartate-semialdehyde dehydrogenase-encoding sequence within the genome of the said recombinant yeast.

In still further embodiments, overexpression of the aspartate-semialdehyde dehydrogenase may result from both (i) the control of the corresponding gene by a strong promoter within the said recombinant yeast and (ii) the presence of a plurality of copies of a aspartate-semialdehyde dehydrogenase-encoding sequence within the genome of the said recombinant yeast.

Homoserine Kinase (THR1)

Homoserine kinase enzyme is a protein which is described in the art for catalyzing the ATP-dependent phosphorylation of L-homoserine to L-homoserine phosphate. Homoserine kinase encoded by the genome of *Saccharomyces cerevisiae* may be termed THR1.

A method implemented to measure the activity level of homoserine kinase belongs to the general knowledge of the one skilled in the art.

In this regard, the one skilled in the art may advantageously refer to the method described by Mannhaupt and Feldmann (1990, Eur J Biochem, Vol. 191: 115-122).

Preferred homoserine kinase in the present specification is an enzyme having an EC number of no. EC 2.7.1.39.

According to a preferred embodiment, the nucleic acid(s) encoding a homoserine kinase may be nucleic acid(s) originating from organisms preferably selected in a group comprising prokaryotic organisms and eukaryotic organisms. In some embodiments, the nucleic acid(s) encoding a homoserine kinase may be nucleic acid(s) originating from archaebacteria. In some other preferred embodiments, the nucleic acid(s) encoding a homoserine kinase may be nucleic acid(s) originating from yeast, and especially from *Saccharomyces cerevisiae*.

According to a yet preferred embodiment, the nucleic acid(s) encoding a homoserine kinase may be nucleic acid(s) selected from the group consisting of sequences having at least 25%, advantageously at least 65%, preferably at least 80%, nucleic acid identity with a nucleic acid of SEQ ID NO: 4, and also a biological activity of the same nature. The nucleic acid of SEQ ID NO: 4 encodes a homoserine kinase originating from *Saccharomyces cerevisiae*.

A biological activity of the same nature regarding this sequence is the capacity to code for an enzyme that catalyzes the ATP-dependent phosphorylation of L-homoserine to L-homoserine phosphate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the homoserine kinase from *Saccharomyces cerevisiae*, the one skilled in the art may refer to the accession number NP011890 in the UniProt database, or to SEQ ID NO. 5 described herein.

According to another particular embodiment, the nucleic acid(s) encoding homoserine kinase may be nucleic acid(s) encoding an amino acid sequence selected from the group consisting of sequences having at least 25%, advantageously at least 65%, preferably at least 80%, amino acid identity with the amino acid sequence of SEQ ID NO: 5, and also a biological activity of the same nature. Illustratively, the homoserine kinase originating from *Aquamarina atlantica* has 25% amino acid identity with the homoserine kinase of SEQ ID NO. 5.

A biological activity of the same nature regarding this sequence is as described previously, i.e. the capacity to catalyze the ATP-dependent phosphorylation of L-homoserine to L-homoserine phosphate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the homoserine kinase in the present invention is regulated by at least one promoter and at least one terminator, such as herein after defined more in details, which are present in 5' and 3' position respectively of the nucleic acid sequence encoding the said homoserine kinase.

As it is specified elsewhere in the present description, in some embodiments of the invention, the homoserine kinase is overexpressed and/or under the control of an inducible or repressible promoter in a recombinant yeast according to the invention.

In some embodiments, overexpression of the homoserine kinase may result from the control of the corresponding gene by a strong promoter within the said recombinant yeast.

In some other embodiments, overexpression of the homoserine kinase may result from the presence of a plurality of copies of a homoserine kinase-encoding sequence within the genome the said recombinant yeast.

In still further embodiments, overexpression of the homoserine kinase may result from both (i) the control of the corresponding gene by a strong promoter within the said recombinant yeast and (ii) the presence of a plurality of copies of a homoserine kinase-encoding sequence within the genome the said recombinant yeast.

Threonine Synthase (THR4)

Threonine synthase enzyme is a protein which is described in the art for catalyzing the $H_2O$-dependent dephosphorylation of O-phospho-L-homoserine to L-threonine. Threonine synthase encoded by the genome of *Saccharomyces cerevisiae* may be termed THR4.

A method implemented to measure the activity level of threonine synthase belongs to the general knowledge of the one skilled in the art.

In this regard, the one skilled in the art may advantageously refer to the method described by in Schildkraut and Greer Journal of Bacteriology, (1973), Vol. 115, p. 777-785.

Preferred threonine synthase in the present specification is an enzyme having an EC number of no. EC 4.2.3.1.

According to a preferred embodiment, the nucleic acid(s) encoding a threonine synthase may be nucleic acid(s) originating from organisms preferably selected in a group comprising prokaryotic organisms and eukaryotic organisms. In some embodiments, the nucleic acid(s) encoding a threonine synthase may be nucleic acid(s) originating from archaebacteria. In some other preferred embodiments, the nucleic acid(s) encoding a threonine synthase may be nucleic acid(s) originating from yeast, and especially from *Saccharomyces cerevisiae*.

According to a yet preferred embodiment, the nucleic acid(s) encoding a threonine synthase may be nucleic acid(s) selected from the group consisting of sequences having at least 25%, advantageously at least 65%, preferably at least 80%, nucleic acid identity with a nucleic acid of SEQ ID NO: 6, and also a biological activity of the same nature. The nucleic acid of SEQ ID NO: 6 encodes a threonine synthase originating from *Saccharomyces cerevisiae*.

A biological activity of the same nature regarding this sequence is the capacity to code for an enzyme that catalyzes the $H_2O$-dependent dephosphorylation of 0-phospho-L-homoserine to L-threonine.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the threonine synthase from *Saccharomyces cerevisiae*, the one skilled in the art may refer to the accession number NP_009982.1 in the UniProt database, or to SEQ ID NO. 7 described herein.

According to another particular embodiment, the nucleic acid(s) encoding threonine synthase may be nucleic acid(s) encoding an amino acid sequence selected from the group consisting of sequences having at least 25%, advantageously at least 65%, preferably at least 80%, amino acid identity with the amino acid sequence of SEQ ID NO: 7, and also a biological activity of the same nature. Illustratively, the threonine synthase originating from *Aquamarina atlantica* has 25% amino acid identity with the threonine synthase of SEQ ID NO. 7.

A biological activity of the same nature regarding this sequence is as described previously, i.e. the capacity to catalyze the $H_2O$-dependent dephosphorylation of O-phospho-L-homoserine to L-threonine.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the threonine synthase in the present invention is regulated by at least one promoter and at least one terminator, such as herein after defined more in details, which are present in 5' and 3' position respectively of the nucleic acid sequence encoding the said threonine synthase.

As it is specified elsewhere in the present description, in some embodiments of the invention, the threonine kinase is overexpressed and/or under the control of an inducible or repressible promoter in a recombinant yeast according to the invention.

In some embodiments, overexpression of the threonine synthase may result from the control of the corresponding gene by a strong promoter within the said recombinant yeast.

In some other embodiments, overexpression of the threonine synthase may result from the presence of a plurality of copies of a threonine synthase-encoding sequence within the genome the said recombinant yeast.

In still further embodiments, overexpression of the threonine synthase may result from both (i) the control of the corresponding gene by a strong promoter within the said recombinant yeast and (ii) the presence of a plurality of copies of a threonine synthase-encoding sequence within the genome the said recombinant yeast.

Aspartokinase (HOM3)

The aspartokinase enzyme is a protein which is described in the art for catalyzing the conversion of L-aspartate in the presence of ATP into 4-phospho-L-aspartate. The aspartokinase encoded by the genome of *Saccharomyces cerevisiae* may be termed HOM3.

A method implemented to measure the activity level of aspartokinase belongs to the general knowledge of the one skilled in the art.

In this regard, the one skilled in the art may advantageously refer to the method described by Stadtman et al. (1961, J Biol Chem, Vol. 236 (7): 2033-2038).

Preferred aspartokinase in the present specification is an enzyme having an EC number of no. EC 2.7.2.4.

According to a preferred embodiment, the nucleic acid(s) encoding an aspartokinase may be nucleic acid(s) originating from organisms preferably selected in a group comprising prokaryotic organisms and eukaryotic organisms. In some embodiments, the nucleic acid(s) encoding an aspartokinase may be nucleic acid(s) originating from archaebacteria. In some embodiments, the nucleic acid(s) encoding an aspartokinase may be nucleic acid(s) originating from organisms preferably selected from *Bacillus subtilis*, and yeasts. In some other preferred embodiments, the nucleic acid(s) encoding an aspartokinase may be nucleic acid(s) originating from yeast, and especially from *Saccharomyces cerevisiae*.

According to a yet preferred embodiment, the nucleic acid(s) encoding an aspartokinase may be nucleic acid(s) selected from the group consisting of sequences having at least 25%, advantageously at least 65%, preferably at least 80%, nucleic acid identity with a nucleic acid of SEQ ID NO. 8, and also a biological activity of the same nature. The nucleic acid of SEQ ID NO. 8 encodes an aspartokinase originating from Saccharomyces cerevisiae.

A biological activity of the same nature regarding this sequence is the capacity to code for an enzyme that catalyzes the conversion of L-aspartate in the presence of ATP into 4-phospho-L-aspartate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the aspartokinase from Saccharomyces cerevisiae, the one skilled in the art may refer to the accession number NP010972 in the UniProt database, or to SEQ ID NO. 9 described herein.

According to another particular embodiment, the nucleic acid(s) encoding aspartokinase may be nucleic acid(s) encoding an amino acid sequence selected from the group consisting of sequences having at least 25%, advantageously at least 65%, preferably at least 80%, amino acid identity with the amino acid sequence of SEQ ID NO: 9, and also a biological activity of the same nature. Illustratively, the aspartokinase originating from Aquamarina atlantica has 25% amino acid identity with the aspartokinase of SEQ ID NO. 9.

A biological activity of the same nature regarding this sequence is as described previously, i.e. the capacity to catalyze the conversion of L-aspartate in the presence of ATP into 4-phospho-L-aspartate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the aspartokinase in the present invention is regulated by at least one promoter and at least one terminator, such as herein after defined more in details, which are present in 5' and 3' position respectively of the nucleic acid sequence encoding the said aspartokinase.

As it is specified elsewhere in the present description, the strong aspartokinase expression shall be controlled in a recombinant yeast according to the invention.

In preferred embodiments, the controlled strong expression of the aspartokinase is performed by placing the aspartokinase-encoding nucleic acid sequence under the control of an appropriate inducible or repressible promoter, preferably a strong inducible or repressible promoter.

Aspartate Kinase (AK)

The aspartate kinase enzyme is a protein which is described in the art for catalyzing the conversion of L-aspartate in the presence of ATP into 4-phospho-L-aspartate. The aspartate kinase encoded by the genome of Bacillus subtilis may be termed AK.

A method implemented to measure the activity level of aspartate kinase belongs to the general knowledge of the one skilled in the art and is the same as the one indicated previously for aspartokinase.

According to a preferred embodiment, the nucleic acid(s) encoding an aspartate kinase may be nucleic acid(s) originating from organisms preferably selected in a group comprising prokaryotic organisms and eukaryotic organisms. In some embodiments, the nucleic acid(s) encoding an aspartate kinase may be nucleic acid(s) originating from archaebacteria. In some embodiments, the nucleic acid(s) encoding an aspartate kinase may be nucleic acid(s) originating from organisms preferably selected from Bacillus subtilis, and yeasts. In some other preferred embodiments, the nucleic acid(s) encoding an aspartate kinase may be nucleic acid(s) originating from yeast, and especially from Saccharomyces cerevisiae.

For the nucleic acid sequence, it may be referred to the one disclosed in the access number NC_000964.3 in the NCBI database.

According to a yet preferred embodiment, the nucleic acid(s) encoding an aspartate kinase may be nucleic acid(s) selected from the group consisting of sequences having at least 25%, advantageously at least 65%, preferably at least 80%, nucleic acid identity with a nucleic acid of SEQ ID NO. 10, and also a biological activity of the same nature.

The nucleic acid of SEQ ID NO. 10 encodes an aspartate kinase originating from *Bacillus subtilis*.

A biological activity of the same nature regarding this sequence is the capacity to code for an enzyme that catalyzes the conversion of L-aspartate in the presence of ATP into 4-phospho-L-aspartate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the aspartate kinase from *Bacillus subtilis*, the one skilled in the art may refer to the accession number NP_389558.2 in the UniProt database, or to SEQ ID NO. 11 described herein.

According to another particular embodiment, the nucleic acid(s) encoding aspartate kinase may be nucleic acid(s) encoding an amino acid sequence selected from the group consisting of sequences having at least 25%, advantageously at least 65%, preferably at least 80%, amino acid identity with the amino acid sequence of SEQ ID NO. 11, and also a biological activity of the same nature. Illustratively, the aspartate kinase originating from *Aquamarina atlantica* has 25% amino acid identity with the aspartokinase of SEQ ID NO. 11.

A biological activity of the same nature regarding this sequence is as described previously, i.e. the capacity to catalyze the conversion of L-aspartate in the presence of ATP into 4-phospho-L-aspartate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the aspartate kinase in the present invention is regulated by at least one promoter and at least one terminator, such as herein after defined more in details, which are present in 5' and 3' position respectively of the nucleic acid sequence encoding the said aspartate kinase.

As it is specified elsewhere in the present description, the strong aspartate kinase expression shall be controlled in a recombinant yeast according to the invention.

In preferred embodiments, the controlled strong expression of the aspartate kinase is performed by placing the aspartate kinase-encoding nucleic acid sequence under the control of an appropriate inducible or repressible promoter, preferably a strong inducible or repressible promoter.

Specific Embodiments of a Threonine-Producing Recombinant Yeast

Aspartate Transaminase Over Expression and/or Controlled Expression

In preferred embodiments of a recombinant yeast according to the invention, at least one nucleic acid encoding an aspartate transaminase is overexpressed and/or is under the control of an inducible or repressible promoter.

The aspartate transaminase enzyme (also known as aspartate aminotransferase) is a protein which is described in the art for catalyzing the reaction of L-aspartate and 2-oxoglutarate for producing oxaloacetate and L-glutamate. The aspartate transaminase enzyme encoded by the genome *Saccharomyces cerevisiae* may be termed AAT2.

According to these embodiments, over expression of an aspartate transaminase-encoding gene is obtained by inserting, at selected location(s) of the yeast genome, one or more copies of an expression cassette comprising an aspartate transaminase coding sequence. Aspartate transaminase and aspartate-transaminase-encoding gene that are encompassed by the invention are detailed elsewhere in the present specification.

In some of these embodiments, the said one or more copies of an expression cassette comprising an aspartate transaminase coding sequence comprise regulatory sequences allowing a strong expression of the aspartate transaminase, such as a strong promoter that is functional in yeast cells.

In addition to or as an alternative to these embodiments of a recombinant yeast according to the invention, at least one aspartate transaminase-encoding gene can be under the control of an inducible or repressible promoter that is functional in yeast cells.

Without wishing to be bound by any particular theory, the inventors believe that an over expression of an aspartate transaminase may induce a high level of conversion of oxaloacetate into aspartate. The same applies when at least one aspartate transaminase coding sequence is under the control of an inducible or repressible promoter.

A method implemented to measure the activity level of an aspartate transaminase belongs to the general knowledge of the one skilled in the art.

In this regard, the one skilled in the art may advantageously refer to the method described in Yagi et al. (1982, Biochem, VOl. 92: 35-43).

In some embodiments, the said aspartate transaminase-encoding gene is the AAT2 gene from *Saccharomyces cerevisiae*, as shown in the examples herein.

In preferred embodiments, the aspartate aminotransferase is encoded by the A. *Thaliana* AAT2-gene.

In preferred embodiments, the said aspartate transaminase-encoding gene is placed under the control of the inducible or repressible promoter pSAM4 or of the inducible or repressible promoter pACU1 or of the strong promoter pADH1 or of the strong promoter pPGK1 or of the strong promoter pTEF3.

Illustratively, the AAT2 gene may be inserted within the TRP1 gene and/or within the PYK1 gene and/or within the GNP1 gene and/or within the MUP3 gene, as it is shown in the examples herein.

Preferred aspartate transaminase in the present specification is known by the EC number 2.6.1.1.

The nucleic acid(s) encoding an aspartate transaminase may be nucleic acid(s) originating from organisms preferably selected in a group comprising prokaryotic organisms and eukaryotic organisms. In some embodiments, the nucleic acid(s) encoding an aspartate transaminase may be nucleic acid(s) originating from archaebacteria. In some preferred embodiments, the nucleic acid(s) encoding an aspartate transaminase may be nucleic acid(s) originate(s) from a yeast organism, and most preferably *Saccharomyces cerevisiae*.

According to a yet preferred embodiment, the nucleic acid(s) encoding an aspartate transaminase or AAT2 may be nucleic acid(s) selected from the group consisting of sequences having at least 39%, advantageously at least 65%, and preferably at least 80%, nucleic acid identity with the nucleic acid sequences of SEQ ID NO: 12, and also a biological activity of the same nature.

A biological activity of the same nature regarding this sequence is the capacity to code for an enzyme that catalyzes the reaction of L-aspartate and 2-oxoglutarate for producing oxaloacetate and L-glutamate.

As described herein, a nucleic acid sequence having at least 39% nucleotide identity with a reference nucleic acid sequence encompasses nucleic acid sequences having at least 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 12, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 14, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 14, and also a biological activity of the same nature.

For the amino acid sequence of the aspartate transaminase from *Saccharomyces cerevisiae*, the one skilled in the art may refer to the accession number NP013127 in the UniProt database, or to SEQ ID NO. 13 described herein. Illustratively, the aspartate transaminase originating from *E. coli* has 39% amino acid identity with the aspartate transaminase AAT2 of SEQ ID NO. 13.

According to another particular embodiment, the nucleic acid(s) encoding an aspartate transaminase may be nucleic acid(s) encoding an amino acid sequence selected from the group consisting of sequences having at least 39%, advantageously at least 65%, preferably at least 80%, identity with the amino acid sequence of SEQ ID NO: 13, and also a biological activity of the same nature.

A biological activity of the same nature regarding this sequence is as described previously, i.e. the capacity to catalyze the reaction of L-aspartate and 2-oxoglutarate for producing oxaloacetate and L-glutamate.

As described herein, an amino acid sequence having at least 39% amino acid identity with a reference nucleic acid sequence encompasses amino acid sequences having at least 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 13, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 13, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 13, and also a biological activity of the same nature.

As above-mentioned, the expression level of the aspartate transaminase in the present invention is regulated by at least one promoter and at least one terminator, such as herein after defined more in details, which are present in 5' and 3' position respectively of the nucleic acid sequence encoding the aspartate transaminase.

As it is specified elsewhere in the present description, aspartate transaminase is overexpressed in a recombinant yeast according to the invention.

In some embodiments, overexpression of aspartate transaminase may result from the control of the corresponding gene by a strong promoter within the said recombinant yeast.

In some other embodiments, overexpression of aspartate transaminase may result from the presence of a plurality of copies of an aspartate transaminase-encoding sequence within the genome the said recombinant yeast.

In still further embodiments, overexpression of aspartate transaminase may result from both (i) the control of the corresponding gene by a strong promoter within the said recombinant yeast and (ii) the presence of a plurality of copies of an aspartate transaminase-encoding sequence within the genome the said recombinant yeast.

Glutamate Dehydrogenase Over Expression and/or Controlled Expression

In preferred embodiments of a recombinant yeast according to the invention, at least one nucleic acid encoding a glutamate dehydrogenase that converts oxo-glutarate to glutamate-encoding gene is overexpressed and/or is under the control of an inducible or repressible promoter.

According to a particular embodiment, the genome of a recombinant strain of the invention is such that at least one nucleic acid encoding a glutamate dehydrogenase that converts oxo-glutarate to glutamate is overexpressed and/or is under the control of an inducible or repressible promoter.

The glutamate dehydrogenase enzyme (also known as NAD-specific glutamate dehydrogenase) is a protein which is described in the art for catalyzing the transformation of 2-oxoglutarate for producing L-glutamate. Thus, glutamate dehydrogenase is an enzyme specifically involved in the chemical reaction involving the conversion of 2-oxoglutarate to L-glutamate, in the presence of NADH.

According to these embodiments, over expression of a glutamate dehydrogenase enzyme-encoding gene is obtained by inserting, at selected location(s) of the yeast genome, one or more copies of an expression cassette comprising a glutamate dehydrogenase coding sequence. Glutamate dehydrogenase and a glutamate dehydrogenase-encoding gene that are encompassed by the invention are detailed elsewhere in the present specification.

In some of these embodiments, the said one or more copies of an expression cassette comprising a glutamate dehydrogenase coding sequence comprise regulatory sequences allowing a strong expression of the glutamate dehydrogenase, such as a strong promoter that is functional in yeast cells.

In addition to or as an alternative to these embodiments of a recombinant yeast according to the invention, at least one glutamate dehydrogenase-encoding gene can be under the control of an inducible or repressible promoter that is functional in yeast cells.

Without wishing to be bound by any particular theory the inventors believe that the over expression of the glutamate dehydrogenase, by converting oxoglutarate into glutamate, simultaneously generates NAD. The same applies when at least one glutamate dehydrogenase coding sequence is under the control of an inducible or repressible promoter.

A method implemented to measure the activity level of glutamate dehydrogenase belongs to the general knowledge of the one skilled in the art.

In this regard, the one skilled in the art may advantageously refer to the method described in Noor and Punekar (2005, Microbiology, Vol. 151: 1409-1419). In preferred embodiments, the said glutamate dehydrogenase-encoding gene encodes for a glutamate dehydrogenase which uses NADH instead of NADPH, and is more particularly the GDH gene from *Entodinium caudatum* (GDH.eCa), as shown in the examples herein.

Preferred glutamate dehydrogenase in the present specification can in particular be the enzyme having the EC number no. EC 1.4.1.2.

In preferred embodiments, the said glutamate dehydrogenase-encoding gene is placed under the control of the strong promoter pTDH3.

Illustratively, the glutamate dehydrogenase gene may be inserted within the TRP1 gene, as it is shown in the examples herein, and/or within the HIS3 gene and/or within the SAM3 gene.

According to a preferred embodiment, the nucleic acid(s) encoding a glutamate dehydrogenase may be nucleic acid(s) originating from organisms preferably selected in a group comprising prokaryotic organisms and eukaryotic organisms. In some embodiments, the nucleic acid(s) encoding a glutamate dehydrogenase may be nucleic acid(s) originating from archaebacteria. In some embodiments, the nucleic acid(s) encoding a glutamate dehydrogenase may be nucleic acid(s) originating from organisms preferably selected from *Entodinium caudatum*, *Bacillus subtilis* and *Clostridium symbiosium*.

According to a yet preferred embodiment, the nucleic acid(s) encoding a glutamate dehydrogenase may be nucleic acid(s) selected from the group consisting of sequences having at least 49%, advantageously at least 65%, preferably at least 80%, nucleic acid identity with the nucleic acid sequences of SEQ ID NO: 14, and also a biological activity of the same nature. The nucleic acid of SEQ ID NO. 14 encodes a glutamate dehydrogenase originating from *Entodinium caudatum*, the said nucleic acid sequence being codon-optimized for its expression in yeast, and especially in *Saccharomyces cerevisiae*.

A biological activity of the same nature regarding this sequence is the capacity to code for an enzyme that catalyzes the transformation of 2-oxoglutarate for producing L-glutamate.

As described herein, a nucleic acid sequence having at least 49% nucleotide identity with a reference nucleic acid sequence encompasses nucleic acid sequences having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 14, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 14, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 14, and also a biological activity of the same nature.

For the amino acid sequence of the glutamate dehydrogenase from *Entodinium caudatum*, the one skilled in the art may refer to the accession number AAF15393 in the UniProt database, or to SEQ ID NO. 15 described herein. Illustratively, the glutamate dehydrogenase originating from *Giardia intestinalis* has 49% amino acid identity with the glutamate dehydrogenase of SEQ ID NO. 15.

According to another particular embodiment, the nucleic acid(s) encoding a glutamate dehydrogenase may be nucleic acid(s) encoding an amino acid sequence selected from the group consisting of sequences having at least 49%, advantageously at least 65%, preferably at least 80%, amino acid identity with the amino acid sequence of SEQ ID NO: 15, and also a biological activity of the same nature.

A biological activity of the same nature regarding this sequence is as described previously, i.e. the capacity to catalyzes the transformation of 2-oxoglutarate for producing L-glutamate.

As described herein, an amino acid sequence having at least 49% amino acid identity with a reference nucleic acid sequence encompasses amino acid sequences having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 15, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 15, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 15, and also a biological activity of the same nature.

As above-mentioned, the expression level of the glutamate dehydrogenase in the present invention is regulated by at least one promoter and at least one terminator, such as herein after defined more in details, which are present in 5' and 3' position respectively of the nucleic acid sequence encoding the said glutamate dehydrogenase.

As it is specified elsewhere in the present description, the glutamate dehydrogenase is overexpressed in a recombinant yeast according to the invention.

In some embodiments, overexpression of the glutamate dehydrogenase may result from the control of the corresponding gene by a strong promoter within the said recombinant yeast.

In some other embodiments, overexpression of the glutamate dehydrogenase may result from the presence of a plurality of copies of a glutamate dehydrogenase-encoding sequence within the genome the said recombinant yeast.

In still further embodiments, overexpression of the glutamate dehydrogenase may result from both (i) the control of the corresponding gene by a strong promoter within the said recombinant yeast and (ii) the presence of a plurality of copies of a glutamate dehydrogenase-encoding sequence within the genome the said recombinant yeast.

Over Expression of a Homoserine Dehydrogenase

In some embodiments of a threonine-producing recombinant yeast according to the invention, the genome of said recombinant yeast is such that at least one nucleic acid encoding a homoserine dehydrogenase is overexpressed.

In preferred embodiments of a recombinant yeast according to the invention, over expression of a homoserine dehydrogenase (HOME)-encoding gene is obtained by inserting, at selected location(s) of the yeast genome, one or more copies of an expression cassette comprising a homoserine dehydrogenase coding sequence. A homoserine dehydrogenase and a homoserine dehydrogenase-encoding gene that are encompassed by the invention are detailed elsewhere in the present specification.

In some of these embodiments, the said one or more copies of an expression cassette comprising a homoserine dehydrogenase coding sequence comprise regulatory sequences allowing a strong expression of the homoserine dehydrogenase, such as a strong promoter that is functional in yeast cells.

In other embodiments, the said one or more copies of an expression cassette comprising a homoserine dehydrogenase coding sequence comprise regulatory sequences allowing a strong expression of the homoserine dehydrogenase, such as a strong promoter that is functional in yeast cells.

Without wishing to be bound by any particular theory, the inventors believe that an over expression of a homoserine dehydrogenase increases the conversion of the intermediate metabolite aspartyl-semialdehyde into homoserine.

In some embodiments, it is made use of the homoserine dehydrogenase originating from a yeast, such as the gene from *Saccharomyces cerevisiae*, HOME. In some embodiments, it is introduced a plurality of copies of the homoserine dehydrogenase-encoding gene in the yeast genome. In some embodiments, and especially in embodiments wherein sole one copy of the homoserine dehydrogenase-encoding gene is present, the said HOME-encoding gene is placed under the control of a strong promoter.

In preferred embodiments, the said homoserine dehydrogenase-encoding gene is the gene from *Saccharomyces cerevisiae*, as shown in the examples herein.

In preferred embodiments, the said homoserine dehydrogenase-encoding gene is placed under the control of the strong promoter pRPLA1 or the strong promoter pADH1.

Illustratively, the homoserine dehydrogenase gene may be inserted within the HOM3 gene and/or within the MUP3 gene, as it is shown in the examples herein.

Deletion or Under Expression of Homoserine-O-Acetyltransferase-Encoding Gene

In preferred embodiments of a recombinant yeast according to the invention, the said recombinant yeast is further preferably defined as having a genome in which:

a) at least one, preferably all, endogenous nucleic acid encoding an homoserine-O-acetyltransferase has been deleted, and/or b) at least one, preferably all, nucleic acid encoding an homoserine-O-acetyltransferase is under the control of an inducible or repressible promoter and/or is in a destabilized form.

Without wishing to be bound by any particular theory, the inventors believe that an under expression of homoserine-O-acetyltransferase gene shall increase phospho-homoserine production by the recombinant yeast by reducing the consumption of the produced homoserine by its conversion into acetylhomoserine.

In a particular embodiment, the recombinant yeast of the invention is further defined as having a genome in which (a) at least one endogenous nucleic acid encoding an homoserine-O-acetyltransferase has been deleted, and (b) at least one nucleic acid encoding an homoserine-O-acetyltransferase is under the control of an inducible or repressible promoter and/or is in a destabilized form.

In some embodiments, under expression of homoserine-O-acetyltransferase (MET2) may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Homoserine-O-acetyltransferase under expression also encompasses the insertion of a nucleic acid encoding a destabilized homoserine-O-acetyltransferase. A destabilized homoserine-O-acetyltransferase is a variant of homoserine-O-acetyltransferase that is more rapidly degraded within the yeast cell than the parent homoserine-O-acetyltransferase.

In preferred embodiments, a destabilized homoserine-O-acetyltransferase consists of a degron-tagged homoserine-O-acetyltransferase protein.

For example, the homoserine-O-acetyltransferase gene can be interrupted by loxP, or for example by URA3.K1-loxP, and is thus deleted.

Deletion or Under Expression of Methionine Synthase-Encoding Gene

In preferred embodiments of a recombinant yeast according to the invention, the said recombinant yeast is further preferably defined as having a genome in which:

a) at least one, preferably all, endogenous nucleic acid encoding a methionine synthase has been deleted, and/or b) at least one, preferably all, nucleic acid encoding a methionine synthase is under the control of an inducible or repressible promoter and/or is in a destabilized form.

The methionine synthase is a protein which is described in the art for catalyzing the conversion of O-acetyl-L-homoserine (OAH) in the presence of methanthiol into methionine and acetate. The methionine synthase is also described in the art for catalyzing the conversion of OAH into homocysteine or the conversion of O-acetylserine (OAS) into cysteine. The methionine synthase encoded by the genome of Saccharomyces cerevisiae may be termed MET17. The methionine synthase encoded by the genome of Saccharomyces cerevisiae may also be termed MET25 or MET15 in the art.

Without wishing to be bound by any particular theory, the inventors believe that an under expression of methionine synthase gene shall increase phospho-homoserine production by the recombinant yeast by reducing the consumption of the produced homoserine by its conversion into homocysteine.

In some embodiments, under expression of methionine synthase may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Methionine synthase under expression also encompasses the insertion of a nucleic acid encoding a destabilized methionine synthase. A destabilized methionine synthase (MET17) is a variant of methionine synthase that is more rapidly degraded within the yeast cell than the parent methionine synthase.

In preferred embodiments, a destabilized methionine synthase consists of a degron-tagged methionine synthase protein.

For example, the methionine synthase gene can be interrupted by loxP, or for example by URA3.K1-loxP, and is thus deleted.

Homoserine Dehydrogenase (HOM6)

The homoserine dehydrogenase enzyme is a protein which is described in the art for catalyzing the conversion of L-homoserine into L-aspartate 4-semialdehyde, in the presence of NAD or NADP. The homoserine dehydrogenase encoded by the genome of Saccharomyces cerevisiae may be termed HOM6.

A method implemented to measure the activity level of homoserine dehydrogenase belongs to the general knowledge of the one skilled in the art.

In this regard, the one skilled in the art may advantageously refer to the method described by Calnyanto et al. (2006, Microbiology, Vol. 152: 105-112).

Preferred homoserine dehydrogenase in the present specification is an enzyme having an EC number of no. 1.1.1.3.

According to a preferred embodiment, the nucleic acid(s) encoding a homoserine dehydrogenase may be nucleic acid(s) originating from organisms preferably selected in a group comprising prokaryotic organisms and eukaryotic organisms. In some preferred embodiments, the nucleic acid(s) encoding a homoserine dehydrogenase may be nucleic acid(s) originating from a yeast, and especially from Saccharomyces cerevisiae.

According to a yet preferred embodiment, the nucleic acid(s) encoding a homoserine dehydrogenase may be nucleic acid(s) selected from the group consisting of sequences having at least 31%, advantageously at least 65%, preferably at least 80%, nucleic acid identity with a nucleic acid of SEQ ID NO: 16, and also a biological activity of the same nature. The nucleic acid of SEQ ID NO: 16 encodes a homoserine dehydrogenase originating from Saccharomyces, that may also be termed HOM6.

As described herein, a nucleic acid sequence having at least 31% nucleotide identity with a reference nucleic acid sequence encompasses nucleic acid sequences having at least 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the with the nucleic acid sequence of SEQ ID NO: 16, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 16, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 16, and also a biological activity of the same nature.

For the amino acid sequence of the homoserine dehydrogenase from Saccharomyces cerevisiae, the one skilled in the art may refer to the accession number AJR75529 or NP012673 in the UniProt database, or to SEQ ID NO: 17 described herein.

According to another particular embodiment, the nucleic acid(s) encoding homoserine dehydrogenase may be nucleic acid(s) encoding an amino acid sequence selected from the group consisting of sequences having at least 31%, advantageously at least 65%, preferably at least 80%, amino acid identity with the amino acid sequence of SEQ ID NO: 17, and also a biological activity of the same nature. Illustratively, the homoserine dehydrogenase originating from *Stenotrophomonas maltophilia* has 31% amino acid identity with the homoserine dehydrogenase of SEQ ID NO. 17.

As described herein, an amino acid sequence having at least 31% amino acid identity with a reference nucleic acid sequence encompasses amino acid sequences having at least 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 17, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 17, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 17, and also a biological activity of the same nature.

As above-mentioned, the expression level of the homoserine dehydrogenase in the present invention is regulated by at least one promoter and at least one terminator, such as herein after defined more in details, which are present in 5' and 3' position respectively of the nucleic acid sequence encoding the said homoserine dehydrogenase.

In a particular embodiment, the genome of a recombinant yeast of the invention is such that at least one nucleic acid encoding an homoserine dehydrogenase is overexpressed.

In some embodiments, overexpression of the homoserine dehydrogenase may result from the control of the corresponding gene by a strong promoter within the said recombinant yeast.

In some other embodiments, overexpression of the homoserine dehydrogenase may result from the presence of a plurality of copies of a homoserine dehydrogenase-encoding sequence within the genome the said recombinant yeast.

In still further embodiments, overexpression of the homoserine dehydrogenase may result from both (i) the control of the corresponding gene by a strong promoter within the said recombinant yeast and (ii) the presence of a plurality of copies of a homoserine dehydrogenase-encoding sequence within the genome the said recombinant yeast.

Homoserine O-Acetyltransferase (MET2)

The homoserine O-acetyl transferase enzyme is a protein which is described in the art for catalyzing the reaction between Acetyl-CoA and L-homoserine into CoA and O-acetyl-L-homoserine. The homoserine O-acetyl transferase encoded by the genome of *Saccharomyces cerevisiae* may be termed MET2.

A method implemented to measure the activity level of homoserine O-acetyl transferase belongs to the general knowledge of the one skilled in the art.

In this regard, the one skilled in the art may advantageously refer to the method described by Shuzo Yamagata (1987, The Journal of Bacteriology, Vol. 169(8): 3458-3463.

Preferred homoserine O-acetyl transferase in the present specification is an enzyme having an EC number of no. EC 2.3.1.31.

According to a preferred embodiment, the nucleic acid(s) encoding a homoserine O-acetyl transferase may be nucleic acid(s) originating from organisms preferably selected in a group comprising prokaryotic organisms and eukaryotic organisms. In some embodiments, the nucleic acid(s) encoding a homoserine O-acetyl transferase may be nucleic acid(s) originating from archaebacteria. In some embodiments, the nucleic acid(s) encoding a homoserine O-acetyl transferase may be nucleic acid(s) originating from organisms preferably selected from *Corynebacterium glutamicum*, and yeasts. In some other preferred embodiments, the nucleic acid(s) encoding a homoserine O-acetyl transferase may be nucleic acid(s) originating from yeast, and especially from *Saccharomyces cerevisiae*.

According to a particular embodiment, the nucleic acid(s) encoding a homoserine O-acetyl transferase may be nucleic acid of SEQ ID NO: 18. The nucleic acid of SEQ ID NO: 18 encodes a homoserine O-acetyl transferase originating from *Saccharomyces cerevisiae*, that may also be termed MET2.

For the amino acid sequence of the homoserine O-acetyl transferase from *Saccharomyces cerevisiae*, the one skilled in the art may refer to the accession number NP014122 in the UniProt database, or to SEQ ID NO. 19 described herein.

As above-mentioned, in some embodiments of the invention, the expression level of a homoserine O-acetyl transferase in the present invention is regulated by at least one promoter and at least one terminator, such as herein after defined more in details, which are present in 5' and 3' position respectively of the nucleic acid sequence encoding the said homoserine O-acetyl transferase.

As it is specified elsewhere in the present description, in some embodiments of the invention, the homoserine O-acetyl transferase is (a) fully or partially deleted or (b) under the control of an inducible or repressible promoter and/or in a destabilized form, in a recombinant yeast according to the invention.

Methionine Synthase (MET17)

The methionine synthase is a protein which is described in the art for catalyzing the conversion of O-acetyl-L-homoserine (OAH) into homocysteine. The methionine synthase is also described in the art for catalyzing the conversion of 0-acetylserine (OAS) into cysteine. The methionine synthase encoded by the genome of *Saccharomyces cerevisiae* may be termed MET17. The methionine synthase encoded by the genome of *Saccharomyces cerevisiae* may also be termed MET25 or MET15 in the art.

A method implemented to measure the activity level of methionine synthase belongs to the general knowledge of the one skilled in the art.

In this regard, the one skilled in the art may advantageously refer to the method described by Ravanel (1995, Archives of Biochemistry and Biophysics, Vol. 316: 572-584).

Preferred methionine synthase in the present specification is an enzyme having an EC number of no. 2.5.1.49.

According to a preferred embodiment, the nucleic acid(s) encoding a methionine synthase may be nucleic acid(s) originating from organisms preferably selected in a group comprising prokaryotic organisms and eukaryotic organisms. In some embodiments, the nucleic acid(s) encoding a methionine synthase may be nucleic acid(s) originating from archaebacteria. In some embodiments, the nucleic acid(s) encoding a methionine synthase may be nucleic acid(s) originating from organisms preferably selected from yeast, and especially from Saccharomyces cerevisiae.

According to a particular embodiment, the nucleic acid(s) encoding a methionine synthase may be nucleic acid of SEQ ID NO: 20. The nucleic acid of SEQ ID NO: 20 encodes a methionine synthase originating from Saccharomyces cerevisiae, that may also be termed MET17.

For the amino acid sequence of the methionine synthase from Saccharomyces cerevisiae, the one skilled in the art may refer to the accession number NP013406 in the UniProt database, or to SEQ ID NO. 21 described herein.

As above-mentioned, in some embodiments of the invention, the expression level of a methionine synthase in the present invention is regulated by at least one promoter and at least one terminator, such as herein after defined more in details, which are present in 5' and 3' position respectively of the nucleic acid sequence encoding the said methionine synthase.

As it is specified elsewhere in the present description, in some embodiments of the invention, the methionine synthase is (a) fully or partially deleted or (b) under the control of an inducible or repressible promoter and/or in a destabilized form, in a recombinant yeast according to the invention.

Export of the Compounds of Interest

As it is described below, an exporter protein-encoding gene that may be over expressed in a recombinant yeast according to the invention is the probable transporter AQR1.

Accordingly, in a particular embodiment, the genome of a recombinant yeast of the invention is such that at least one nucleic acid encoding a probable transporter is overexpressed.

AQR1 is a transporter from Saccharomyces cerevisiae. For the amino acid sequence of AQR1 it may be referred to the access number NP_014334 in the UniProt database. For the nucleic acid sequence, it may be referred to the access number NM_001182903 in the NCBI database.

In preferred embodiments of a recombinant yeast according to the invention, over expression of a probable transporter-encoding gene is obtained by inserting, at selected location(s) of the yeast genome, one or more additional copies of an expression cassette comprising the said probable transporter coding sequence.

Without wishing to be bound by any particular theory, the inventors believe that an over expression of a probable transporter-encoding gene shall increase the excretion of the produced threonine outside the yeast cell, e.g. in the culture medium.

In some embodiments, over expression of a probable transporter-encoding gene is obtained by inserting, at selected location(s) of the yeast genome, one or more additional copies of an expression cassette comprising a robable transporter gene coding sequence. In some of these embodiments, the said one or more copies of an expression cassette comprising a probable transporter coding sequence comprise regulatory sequences allowing a strong expression of the said probable transporter, such as a strong promoter that is functional in yeast cells.

In some other embodiments, one copy of a probable transporter-encoding gene is inserted at a selected location of the yeast genome. In these other embodiments, the said one or more copies of an expression cassette comprising a probable transporter coding sequence comprise regulatory sequences allowing a strong expression of the said probable transporter, such as a strong promoter that is functional in yeast cells.

In preferred embodiments, the said amino acid probable transporter AQR1 is placed under the control of the strong promoter pTEF3.

Illustratively, the AQR1 gene may be inserted within the hom3 gene, as it is shown in the examples herein.

In further embodiments of a recombinant yeast according to the invention, the export of the produced threonine outside of the yeast cell may be enhanced by (i) under expression of genes encoding yeast permeases, by (ii) under expression of genes encoding amino acid exporter proteins, or by (iii) both under expression of genes encoding yeast permeases and under expression of genes encoding amino acid exporter proteins.

As it is described below, permease-encoding genes that may be under expressed in a recombinant yeast according to the invention encompass AGP1, AGP3, BAP3, BAP2, GAP1 and GNP1.

AGP1 is the general amino acid permease 1 from Saccharomyces cerevisiae. For the amino acid sequence of AGP1 it may be referred to the access number NP_009905 in the UniProt database. For the nucleic acid sequence, it may be referred to the access number NM_001178671 in the NCBI database.

AGP3 is the general amino acid permease 3 from Saccharomyces cerevisiae. For the amino acid sequence of AGP3 it may be referred to the access number NP_116600 in the UniProt database. For the nucleic acid sequence, it may be referred to the access number NM_001179912 in the NCBI database.

BAP3 is the valine amino acid permease from Saccharomyces cerevisiae. For the amino acid sequence of BAP3 it may be referred to the access number NP_010331 in the UniProt database. For the nucleic acid sequence, it may be referred to the access number NM_001180354 in the NCBI database.

BAP2 is the Leu/Val/Ile amino acid permease from Saccharomyces cerevisiae. For the amino acid sequence of BAP2 it may be referred to the access number NP_009624 in the UniProt database. For the nucleic acid sequence, it may be referred to the access number NM_001178416 in the NCBI database.

GAP1 is the general amino-acid permease from Saccharomyces cerevisiae. For the amino acid sequence of GAP1 it may be referred to the access number NP_012965.3 in the UniProt database. For the nucleic acid sequence, it may be referred to the access number NM_001179829 in the NCBI database.

GNP1 is the high-affinity glutamine permease from Saccharomyces cerevisiae. For the amino acid sequence of GNP1 it may be referred to the access number NP_010796 in the UniProt database. For the nucleic acid sequence, it may be referred to the access number NM_001180816 in the NCBI database.

In some embodiments of a recombinant yeast according to the invention, the said recombinant yeast is further defined as having an under expression one or more genes encoding a permease, that encompasses AGP1, AGP3, BAP3, BAP2, GAP1 and GNP1 permeases.

Without wishing to be bound by any particular theory, the inventors believe that an under expression of any of the permease genes shall increase the excretion of the produced threonine outside the yeast cell, e.g. in the culture medium.

In a preferred embodiment, a recombinant yeast of the invention has a genome into which at least one of the following modifications has been performed:
- (A) at least one, preferably all, endogenous nucleic acid encoding a general amino acid permease GAP1 has been deleted from the genome of the yeast, and, optionally:
  - (i) at least one nucleic acid encoding a general amino acid permease GAP1 has been inserted and is under the control of an inducible or repressible promoter, and/or
  - (ii) at least one nucleic acid encoding a destabilized general amino acid permease GAP1 has been inserted;
- (B) at least one, preferably all, endogenous nucleic acid encoding a high-affinity glutamine permease GNP1 has been deleted from the genome of the yeast, and, optionally:
  - (i) at least one nucleic acid encoding a high-affinity glutamine permease GNP1 has been inserted and is under the control of an inducible or repressible promoter, and/or
  - (ii) at least one nucleic acid encoding a destabilized high-affinity glutamine permease GNP1 has been inserted;
- (C) at least one, preferably all, endogenous nucleic acid encoding a general amino acid permease AGP1 has been deleted from the genome of the yeast, and, optionally:
  - (i) at least one nucleic acid encoding a general amino acid permease AGP1 has been inserted and is under the control of an inducible or repressible promoter, and/or
  - (ii) at least one nucleic acid encoding a destabilized general amino acid permease AGP1 has been inserted.

In a particular embodiment, a recombinant yeast of the invention has a genome into which at least two, and preferably all, of these modifications have been performed.

In a more particular embodiment, a recombinant yeast of the invention has a genome into which all the following modifications have been performed:
- (A) at least one, preferably all, endogenous nucleic acid encoding a general amino acid permease GAP1 has been deleted from the genome of the yeast, and, optionally:
  - (i) at least one nucleic acid encoding a general amino acid permease GAP1 has been inserted and is under the control of an inducible or repressible promoter, and/or
  - (ii) at least one nucleic acid encoding a destabilized general amino acid permease GAP1 has been inserted;
- (B) at least one, preferably all, endogenous nucleic acid encoding a high-affinity glutamine permease GNP1 has been deleted from the genome of the yeast, and, optionally:
  - (i) at least one nucleic acid encoding a high-affinity glutamine permease GNP1 has been inserted and is under the control of an inducible or repressible promoter, and/or
  - (ii) at least one nucleic acid encoding a destabilized high-affinity glutamine permease GNP1 has been inserted; and
- (C) at least one, preferably all, endogenous nucleic acid encoding a general amino acid permease AGP1 has been deleted from the genome of the yeast, and, optionally:
  - (i) at least one nucleic acid encoding a general amino acid permease AGP1 has been inserted and is under the control of an inducible or repressible promoter, and/or
  - (ii) at least one nucleic acid encoding a destabilized general amino acid permease AGP1 has been inserted.

As regards permeases, under expression of one or more of these genes encompasses a complete repression of their expression, e.g. by interruption or deletion of the said one or more permease genes.

In some embodiments, under expression of a permease-encoding gene may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

As regards a permease gene, under expression also encompasses the insertion of a nucleic acid encoding a destabilized permease protein or the insertion of a nucleic acid encoding a destabilized permease protein, or both.

A destabilized permease is a variant of a permease that is more rapidly degraded within the yeast cell than the parent permease.

In preferred embodiments, a destabilized permease consists of a degron-tagged permease protein.

For example, under expressed genes can be interrupted by loxP and are thus deleted.

In a particular embodiment, the nucleic acid encoding an aspartokinase, a general amino acid permease, a high-affinity glutamine permease, a general amino acid permease, an homoserine-O-acetyltransferase and a methionine synthase of the invention are, independently, nucleic acid from a yeast, preferably from *Saccharomyces cerevisiae*.

Further Embodiments of a Threonine-Producing Recombinant Yeast

In view of further increasing threonine production, a recombinant yeast according to the invention may comprise additional genetic changes, such that they produce large quantities of the intermediate product oxaloacetate. These optional genetic changes are described here below.

According to some embodiments of a recombinant yeast according to the invention, production of threonine may be further increased by placing the said recombinant yeast in conditions leading to an increase production of the intermediate metabolite oxaloacetate.

Placing the said recombinant yeast in conditions leading to an increased production of oxaloacetate may be performed by introducing further genetic modifications in the yeast genome.

The present inventors have found that an optimally increased threonine derivatives production may be reached by introducing further genetic changes to the threonine-producing recombinant yeast, that are described below.

First Further Embodiments of a Threonine-Producing Recombinant Yeast

According to these first further embodiments of a threonine-producing recombinant yeast according to the invention, further genetic engineering of the recombinant yeast is performed with the aim of increasing the production of the intermediate product phosphoenol-pyruvate (PEP).

Without wishing to be bound by any particular theory, the inventors believe that the further genetic changes introduced in the threonine-producing recombinant yeast (i) cause an over-production of NADPH, (ii) cause a controlled and balanced conversion of phosphoenol pyruvate into oxaloacetate and pyruvate, respectively, and (iii) cause a reduced conversion of pyruvate into ethanol and a redirection towards conversion of phosphoenol pyruvate into oxaloacetate.

These further genetic changes introduced by genetic engineering in a threonine-producing recombinant yeast according to the invention are specified in more detail below.

According to these embodiments, genetic changes are introduced so as to over-express a glucose-6-phosphate-1-dehydrogenase (also termed MET19 or ZWF1) and a 6-phosphogluconate dehydrogenase, decarboxylating 1 (also termed GND1). Without wishing to be bound by any particular theory, the inventors believe that an over expression of MET19 and GND1 causes an increase in NADPH production.

According to these embodiments, genetic changes are introduced so as to over-express a phosphoenolpyruvate carboxylase (also termed PEPC ou PPC) and/or a phosphoenolpyruvate carboxykinase [ATP] (also termed PCK1 or PEPCK).

According to these embodiments, genetic changes are introduced so as to under-express a pyruvate kinase 1 (also termed PYK1 or CDC19) and a pyruvate kinase 2 (also termed (PYK2). In some of these embodiments, PYK2 gene may be deleted rather than being under-expressed.

In some of these embodiments, one or more of the genes encoding a pyruvate decarboxylase is (are) inactivated, preferably by deletion. Pyruvate decarboxylase-encoding genes encompass those termed PDC1, PDC5 and PDC6, respectively. According to some of these embodiments, PDC1 and/or PDC6 genes are inactivated, preferably by interruption or deletion, whereas the other pyruvate decarboxylase-encoding gene PDC5 is left unaltered, or its expression is reduced by controlling it with a weak promoter.

In some of these embodiments, alcohol dehydrogenase activity of the recombinant yeast is reduced by altering the expression of one or more of the alcohol dehydrogenase-encoding genes. In some of these embodiments, the expression of ADH1 is reduced by placing the gene under the control of a weak promoter or by producing a destabilized ADH1 enzyme. In some of these embodiments, one or more of ADH3, ADH4 and ADH5 may be inactivated, preferably by interruption or deletion.

In some of these embodiments, an exogenous acetyl dehydrogenase-encoding gene (also termed MHPF) may be introduced in the yeast genome and over-expressed.

In some of these embodiments, an exogenous acetate kinase-encoding gene (also termed ACKA) may be introduced in the yeast genome and over-expressed.

In some of these embodiments, an exogenous phosphate acetyl transferase-encoding gene (also termed PTA) may be introduced in the yeast genome and over-expressed.

Glucose-6-phosphate-1-dehydrogenase

The glucose-6-phosphate-1-dehydrogenase enzyme is a protein which is described in the art for catalyzing D-glucose 6-phosphate to 6-phospho-D-glucono-1,5-lactone, with concomitant reduction of NADP to NADPH.

A method implemented to measure the activity level of glucose-6-phosphate-1-dehydrogenase belongs to the general knowledge of the one skilled in the art.

In this regard, the one skilled in the art may advantageously refer to the method described by Kuby, S. et al. (1966) Dehydrogenases and Oxidases Methods in Enzymology 9, 116-117.

Preferred glucose-6-phosphate-1-dehydrogenase in the present specification is an enzyme having an EC number of no. 1.1.1.49.

For the amino acid sequence of glucose-6-phosphate-1-dehydrogenase (also termed MET19), it may be referred to the access number NP_014158.1 in the UniProt database. For the nucleic acid sequence, it may be referred to the access number NM_001183079.1 in the UniProt database.

6-phosphogluconate Dehydrogenase, Decarboxylating 1

The 6-phosphogluconate dehydrogenase, decarboxylating 1 enzyme is a protein which is described in the art for catalyzing the oxidative decarboxylation of 6-phosphogluconate to ribulose 5-phosphate and $CO_2$, with concomitant reduction of NADP to NADPH.

A method implemented to measure the activity level of 6-phosphogluconate dehydrogenase, decarboxylating 1 belongs to the general knowledge of the one skilled in the art.

In this regard, the one skilled in the art may advantageously refer to the method described by He W. et al. (2007) BMC Structural Biology, 7:38.

Preferred 6-phosphogluconate dehydrogenase, decarboxylating 1 in the present specification is an enzyme having an EC number of n° 1.1.1.44.

For the amino acid sequence of 6-phosphogluconate dehydrogenase, decarboxylating 1 (also termed GND1), it may be referred to the access number NP_012053 in the UniProt database. For the nucleic acid sequence, it may be referred to the access number NM_001179314 in the NCBI database.

Pyruvate Kinase 1

The pyruvate kinase 1 enzyme is a protein which is described in the art for catalyzing the conversion of phosphoenol pyruvate into pyruvate while generating ATP.

A method implemented to measure the activity level of pyruvate kinase 1 belongs to the general knowledge of the one skilled in the art.

In this regard, the one skilled in the art may advantageously refer to the method described by Susan-resiga and Nowak (biochemistry, 2004, 43, 15230-15245).

Preferred pyruvate kinase 1 in the present specification is an enzyme having an EC number of no. 2.7.1.40.

For the amino acid sequence of pyruvate kinase 1 (also termed PYK1) it may be referred to the access number NP_009362 in the UniProt database. For the nucleic acid sequence, it may be referred to the access number NM_001178183 in the NCBI database.

Pyruvate Kinase 2

The pyruvate kinase 2 enzyme is a protein which is described in the art for catalyzing the conversion of phosphoenolpyruvate into pyruvate while generating ATP. Pyruvate kinase 2 may be used by the yeast cell under conditions in which the level of glycolytic flux is very low.

A method implemented to measure the activity level of pyruvate kinase 2 belongs to the general knowledge of the one skilled in the art.

In this regard, the one skilled in the art may advantageously refer to the method described by Susan-resiga and Nowak (biochemistry, 2004, 43, 15230-15245). Preferred pyruvate kinase 2 in the present specification is an enzyme having an EC number of no. 2.7.1.40.

For the amino acid sequence of pyruvate kinase 2 (also termed PYK2) it may be referred to the access number NP_014992 in the UniProt database. For the nucleic acid sequence, it may be referred to the access number NM_001183767 in the NCBI database.

Pyruvate Decarboxylase Isozyme 1

The pyruvate decarboxylase isozyme 1 is a protein which is described in the art for being involved in the non-oxidative conversion of pyruvate to acetaldehyde and carbon dioxide during alcoholic fermentation.

A method implemented to measure the activity level of the pyruvate decarboxylase isozyme 1 belongs to the general knowledge of the one skilled in the art.

In this regard, the one skilled in the art may advantageously refer to the method described by Wang et al. (Biochemistry, 2001, 40:1755-1763).

Preferred pyruvate decarboxylase isozyme 1 in the present specification is an enzyme having an EC number of n° 4.1.1.1.

For the amino acid sequence of pyruvate decarboxylase isozyme 1 (also termed PDC1) it may be referred to the access number NP_013145 in the UniProt database. For the nucleic acid sequence, it may be referred to the access number NM_001181931 in the NCBI database.

Pyruvate Decarboxylase Isozyme 5

The pyruvate decarboxylase isozyme 5 is a protein which is described in the art for being involved in the nonoxidative conversion of pyruvate to acetaldehyde and carbon dioxide during alcoholic fermentation.

A method implemented to measure the activity level of the pyruvate decarboxylase isozyme 5 belongs to the general knowledge of the one skilled in the art.

In this regard, the one skilled in the art may advantageously refer to the method described by Wang et al. (Biochemistry, 2001, 40:1755-1763).

Preferred pyruvate decarboxylase isozyme 5 in the present specification is an enzyme having an EC number of no. 4.1.1.1.

For the amino acid sequence of pyruvate decarboxylase isozyme 5 (also termed PDC5) it may be referred to the access number NP_013235 in the UniProt database. For the nucleic acid sequence, it may be referred to the access number NM_001182021 in the NCBI database.

Pyruvate Decarboxylase Isozyme 6

The pyruvate decarboxylase isozyme 6 is a protein which is described in the art for being involved in the nonoxidative conversion of pyruvate to acetaldehyde and carbon dioxide during alcoholic fermentation.

A method implemented to measure the activity level of the pyruvate decarboxylase isozyme 6 belongs to the general knowledge of the one skilled in the art.

In this regard, the one skilled in the art may advantageously refer to the method described by Wang et al. (Biochemistry, 2001, 40:1755-1763).

Preferred pyruvate decarboxylase isozyme 6 in the present specification is an enzyme having an EC number of no. 4.1.1.1.

For the amino acid sequence of pyruvate decarboxylase isozyme 6 (also termed PDC6) it may be referred to the access number NP_013235 in the UniProt database. For the nucleic acid sequence, it may be referred to the access number NM_001182021 in the NCBI database.

Acetaldehyde Dehydrogenase

The acetaldehyde dehydrogenase is a protein which is described in the art for catalyzing the conversion of acetaldehyde to acetyl-CoA, using NAD and coenzyme A.

A method implemented to measure the activity level of acetaldehyde dehydrogenase belongs to the general knowledge of the one skilled in the art.

In this regard, the one skilled in the art may advantageously refer to the method described by Fisher et al. (2013) Chemi. Biol. Interact. 202 70-77.

Preferred acetaldehyde dehydrogenase in the present specification is an enzyme having an EC number of no. 1.2.1.10.

For the amino acid sequence of acetaldehyde dehydrogenase (also termed MHPF) it may be referred to the access number NP_414885 in the UniProt database. For the nucleic acid sequence, it may be referred to the one disclosed in the access number NC_000913.3 in the NCBI database.

Acetate Kinase

The acetate kinase is a protein which is described in the art for the formation of acetyl phosphate from acetate and ATP.

A method implemented to measure the activity level of acetate kinase belongs to the general knowledge of the one skilled in the art.

In this regard, the one skilled in the art may advantageously refer to the method described by Sagers et al. J. Bacteriology (1961) 82 233-238.

For the amino acid sequence of acetate kinase (also termed ACKA) it may be referred to the access number NP_416799 in the UniProt database. For the nucleic acid sequence, it may be referred to the one disclosed in the access number NC 000913.3 in the NCBI database.

Phosphate Acetyltransferase

The phosphate acetyltransferase is a protein which is described in the art for catalyzing the reversible interconversion of acetyl-CoA and acetyl phosphate.

A method implemented to measure the activity level of the phosphate acetyltransferase belongs to the general knowledge of the one skilled in the art.

In this regard, the one skilled in the art may advantageously refer to the method described by Castano-Cerezo and Canovas, Microbial Cell Factories 2009, 8:54.

Preferred phosphate acetyltransferase in the present specification is an enzyme having an EC number of no. 2.3.1.8.

For the amino acid sequence of phosphate acetyltransferase (also termed PTA) it may be referred to the access number NP_416800 in the UniProt database. For the nucleic acid sequence, it may be referred to the one disclosed in the access number NC_000913 in the NCBI database.

Alcohol Dehydrogenase 1

The alcohol dehydrogenase 1 is a protein which is described in the art for catalyzing the conversion of primary unbranched alcohols to their corresponding aldehydes.

A method implemented to measure the activity level of the alcohol dehydrogenase 1 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 1 in the present specification is an enzyme having an EC number of no. 1.1.1.1.

For the amino acid sequence of alcohol dehydrogenase 1 (also termed ADH1) it may be referred to the access number NP_014555 in the UniProt database. For the nucleic acid sequence, it may be referred to the access number NM_001183340 in the NCBI database.

Alcohol Dehydrogenase 3

The alcohol dehydrogenase 3 is a protein which is described in the art for catalyzing the conversion of primary unbranched alcohols to their corresponding aldehydes.

A method implemented to measure the activity level of the alcohol dehydrogenase 3 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 3 in the present specification is an enzyme having an EC number of no. 1.1.1.1.

For the amino acid sequence of alcohol dehydrogenase 3 (also termed ADH3) it may be referred to the access number NP_013800 in the UniProt database. For the nucleic acid sequence, it may be referred to the access number NM_001182582 in the NCBI database.

Alcohol Dehydrogenase 4

The alcohol dehydrogenase 4 is a protein which is described in the art for catalyzing the conversion of primary unbranched alcohols to their corresponding aldehydes.

A method implemented to measure the activity level of the alcohol dehydrogenase 4 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 4 in the present specification is an enzyme having an EC number of no. 1.1.1.1.

For the amino acid sequence of alcohol dehydrogenase 4 (also termed ADH4) it may be referred to the access number NP_011258 in the UniProt database. For the nucleic acid sequence, it may be referred to the access number NM_001181122 in the NCBI database.

Alcohol Dehydrogenase 5

The alcohol dehydrogenase 5 is a protein which is described in the art for catalyzing the conversion of primary unbranched alcohols to their corresponding aldehydes.

A method implemented to measure the activity level of the alcohol dehydrogenase 5 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 5 in the present specification is an enzyme having an EC number of no. 1.1.1.1.

For the amino acid sequence of alcohol dehydrogenase 5 (also termed ADH5) it may be referred to the access number NP_009703 in the UniProt database. For the nucleic acid sequence, it may be referred to the access number NM_001178493 in the NCBI database.

Second Further Embodiments of a Threonine-Producing Recombinant Yeast

According to another further embodiments of a threonine-producing recombinant yeast according to the invention, further genetic engineering of the recombinant yeast is performed with the aim of increasing the production of the intermediate product phosphoenol-pyruvate (PEP).

Without wishing to be bound by any particular theory, the inventors believe that the further genetic changes introduced in the threonine-producing recombinant yeast (i) cause an over-production of NADPH, (ii) cause a controlled and balanced conversion of phosphoenol pyruvate into oxaloacetate and pyruvate, respectively, and (iii) cause a reduced conversion of pyruvate into ethanol and a redirection towards conversion of phosphoenol pyruvate into oxaloacetate.

For this purpose, the inventors have conceived a completely novel metabolic pathway, starting from phosphenolpyruvate and ending with the production of oxaloacetate.

These further genetic changes introduced by genetic engineering in a threonine-producing recombinant yeast according to the invention are specified in more detail below.

According to these embodiments, genetic changes are introduced so as to under express the pyruvate kinase 1 (also termed PYK1), and optionally also pyruvate kinase 2 (also termed PYK2). In some of these embodiments, PYK1 may be under-expressed by placing the gene under the control of a weak promoter or of an inducible or repressible promoter. In some of these embodiments, PYK2 may be inactivated, e.g. by interruption or deletion. In some of these embodiments, PYK1 gene may be deleted rather than being under-expressed. In some of these embodiments, PYK1 gene and PYK2 gene may be deleted rather than being under-expressed According to these embodiments, genetic changes are introduced so as to over-express a phosphoenolpyruvate carboxykinase [ATP] (also termed PCK or PCKA or PEPCK), either (i) by constitutive over-expression or (ii) by inducible over-expression.

According to these embodiments, genetic changes are introduced so as over-express in the cytoplasm a malate dehydrogenase, such as a peroxisomal malate dehydrogenase (also termed MDH3), either (i) by constitutive over-expression or (ii) by inducible over-expression.

According to these embodiments, genetic changes are introduced so as over-express a NADP-dependent malic enzyme 3 (also termed ME3 or NADP-ME3), either (i) by constitutive over-expression or (ii) by inducible over-expression.

According to these embodiments, genetic changes are introduced so as to reduce expression of one or more alcohol dehydrogenase(s), preferably one or more alcohol dehydrogenase(s) selected in a group comprising alcohol dehydrogenase 1 (also termed ADH1), alcohol dehydrogenase 3 (also termed ADH3), alcohol dehydrogenase 4 (also termed ADH4) and alcohol dehydrogenase 5 (also termed ADH5), e.g. (i) by placing the corresponding coding sequence under the control of a weak promoter or of an inducible or repressible promoter, or (ii) by production of a destabilized form of the said alcohol dehydrogenase(s).

Still according to these embodiments, genetic changes are introduced so as to over-express an exogenous acetaldehyde dehydrogenase (also termed MHPF), either (i) by constitutive over-expression or (ii) by inducible over-expression.

Pyruvate kinase 1 and pyruvate kinase 2 are as defined previously.

Phosphoenolpyruvate Carboxykinase (PPCK)

The phosphoenol carboxykinase [ATP] enzyme is a protein which is described in the art for catalyzing the conversion of oxaloacetate to phosphoenolpyruvate through direct phosphoryl transfer between the nucleoside triphosphate and oxaloacetate.

A method implemented to measure the activity level of phosphoenol carboxykinase [ATP] belongs to the general knowledge of the one skilled in the art.

In this regard, the one skilled in the art may advantageously refer to the method described by Bazaes S. et al. (2007) The Protein Journal, 26, 265-269 and Mariet J. Van der Werf et al. (1997) Arch Microbiol 167: 332-342.

Preferred phosphoenol carboxykinase [ATP] in the present specification is an enzyme having an EC number of no. 4.1.1.49.

For the amino acid sequence of phosphoenol carboxykinase [ATP] (also termed PCKA) it may be referred to the access number NP_417862 in the UniProt database. For the nucleic acid sequence, it may be referred to the one disclosed in the access number NC 000913 in the NCBI database.

Preferred phosphoenol carboxykinase according to the invention can be selected from phosphoenolpyruvate carboxykinase PPCK such as PEPCK having an EC number of no. 4.1.1.32.

Malate Dehydrogenase

The malate dehydrogenase enzyme is a protein which is described in the art for catalyzing the conversion of malate to oaxaloacetate, in the presence of NADH.

A method implemented to measure the activity level of malate dehydrogenase belongs to the general knowledge of the one skilled in the art. Mention can for example be made of the commercial kit sold by Sigma entitled "Malate dehydrogenase assay kit" under the reference MAK196-1KT.

For the amino acid sequence of malate dehydrogenase (also termed MDH3) it may be referred to the access number NP_010205 in the UniProt database. For the nucleic acid sequence, it may be referred to the access number NM_00118037 in the NCBI database.

NADP-Dependent Malic Enzyme 3

The NADP-dependent malic enzyme 3 enzyme is a protein which is described in the art for catalyzing the conversion of malate to pyruvate, in the presence of NADP.

A method implemented to measure the activity level of NADP-dependent malic enzyme 3 belongs to the general knowledge of the one skilled in the art.

In this regard, the one skilled in the art may advantageously refer to the method described by Gerrard-Wheeler et al. FEBS Journal 276 (2009) 5665-5677.

Preferred NADP-dependent malic enzyme 3 in the present specification is an enzyme having an EC number of no. 1.1.1.40.

For the amino acid sequence of NADP-dependent malic enzyme 3 (also termed NADP-ME3 or ME3) it may be referred to the access number NP_197960 in the UniProt database. For the nucleic acid sequence, it may be referred to the access number NM_122489 in the NCBI database.

The alcohol dehydrogenase 1, alcohol dehydrogenase 3, alcohol dehydrogenase 4, acetaldehyde dehydrogenase and alcohol dehydrogenase 5 are as defined previously.

Promoters

As it is disclosed herein, the expression of the genes of interest that have been genetically engineered for obtaining a recombinant yeast according to the invention comprise appropriate regulatory sequences that are functional in yeast cells, including in *Saccharomyces cerevisiae*.

As disclosed in the present specification, various promoters may be used for the desired expression of the coding sequences of interest, which include (i) constitutive strong promoters (also called strong promoters in the present text), (ii) constitutive weak promoters (also called weak promoters in the present text) and (iii) inducible or repressible promoters. A list of yeast promoter with their relative activities in different media can be found in Keren et al. (2013) Molecular Systems Biology 9:701.

Promoters allowing the constitutive over-expression of a given gene, may be found in literature (Velculescu et al. (1997) Cell 88, 243-251).

Strong promoters more particularly interesting in the present invention may be selected from the group comprising:
pTDH3 (SEQ ID No. 22),
pENO2 (SEQ ID No. 23),
pTEF KI (SEQ ID No. 24),
pTEF3 (SEQ ID No. 25),
pTEF1 (SEQ ID No. 26),
pADH1 (SEQ ID No. 27),
pGMP1 (SEQ ID No. 28),
pFBA1 (SEQ ID No. 29),
pPDC1 (SEQ ID No. 30),
pCCW12 (SEQ ID No. 31), and
pGK1 (SEQ ID No. 32).

According to a particular embodiment, the strong promoter according to the invention is, independently, selected from the group consisting of pTDH3, pENO2, pTEF-KI, pTEF3, pTEF1, pADH1, pGMP1, pFBA1, pPDC1, pCCW12 and pGK1.

Weak promoters more particularly interesting in the present invention may be selected from the group comprising:
pURA3 (SEQ ID No. 34),
pRPLA1 (SEQ ID No. 35),
pNUP57 (SEQ ID No. 114), and
pGAP1 (SEQ ID No. 115).

According to a particular embodiment, the weak promoter according to the invention is, independently, selected from the group consisting of pURA3, pRPLA1, pNUP57 and pGAP1.

As previously mentioned, inducible or repressible promoters are promoters whose activity is controlled by the presence or absence of biotic or abiotic factors and also by the quantity of said factor. Accordingly, for some promoters, their activity will in particular be induced and thus increased when the quantity of a given factor increases or is increased, and, accordingly, the activity of these same promoters can be repressed and thus reduced when the quantity of said factor diminishes or is reduced. The quantity of said factor(s) in the culture medium of a recombinant yeast of the invention comprising inducible or repressible promoters can be decided and thus controlled by the man skilled in the art.

For example, increasing the quantity of methionine in a culture medium of a recombinant yeast according to the invention comprising a pSAM4 promoter will induce and thus increase transcription of the gene under the control of this promoter. On the contrary, reducing the quantity of methionine in said culture medium will lead to a repression, and thus a reduced, transcription of the gene under the control of this promoter.

In another example, increasing the quantity of copper in a culture medium of a recombinant yeast according to the invention comprising a pCTR1 promoter will represse and thus decrease transcription of the gene under the control of this promoter. On the contrary, reducing the quantity of copper in said culture medium will lead to an induced, and thus an increased, transcription of the gene under the control of this promoter.

For this reason, the following promoters are referred to in the present text as being "inducible or repressible promoters".

According to a first embodiment, inducible or repressible promoters according to the invention may be selected from the group comprising promoters inducible or repressible with copper, promoters inducible or repressible with methionine and promoters inducible or repressible with threonine, and are in particular selected from the group consisting of:

pSAM4—methionine inducible or repressible (SEQ ID No. 36),
pCUP1-1—copper inducible or repressible (SEQ ID No. 37),
pCUP1.cgla—copper inducible or repressible (SEQ ID No. 38),
pCUP1.sba—copper inducible or repressible (SEQ ID No. 39),
pACU1—copper inducible or repressible (SEQ ID No. 40),
pACU2—copper inducible or repressible (SEQ ID No. 41),
pACU3p—copper inducible or repressible (SEQ ID No. 42),
pACU4p—copper inducible or repressible (SEQ ID No. 43),
pACU5—copper inducible or repressible (SEQ ID No. 44),
pACU6—copper inducible or repressible (SEQ ID No. 45),
pACU7—copper inducible or repressible (SEQ ID No. 46),
pACU8—copper inducible or repressible (SEQ ID No. 47),
pACU9—copper inducible or repressible (SEQ ID No. 48),
pACU10p—copper inducible or repressible (SEQ ID No. 49),
pACU11—copper inducible or repressible (SEQ ID No. 50),
pACU12—copper inducible or repressible (SEQ ID No. 51),
pACU13—copper inducible or repressible (SEQ ID No. 52),
pACU14—copper inducible or repressible (SEQ ID No. 53),
pACU15—copper inducible or repressible (SEQ ID No. 54),
pGAL/CUP1p—copper inducible or repressible (SEQ ID No. 55),
pCRS5—copper inducible or repressible (SEQ ID No. 56), and
pCHA1—threonine inducible or repressible (SEQ ID No. 57).

Accordingly, in this embodiment, the inducible or repressible promoter according to the invention can in particular, independently, be selected from the group consisting of pSAM4, pCUP1-1, pCUP1.Cgla, pCUP1.sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, and pCHA1.

The activity of these promoters is thus induced by the increasing presence of methionine, copper or threonine as indicated above, and their activity diminishes, i.e. is repressed, when the quantity of methionine, copper or threonine is reduced.

According to a second embodiment, inducible or repressible promoters according to the invention may be selected from the group comprising promoters inducible or repressible with copper, promoters inducible or repressible with glucose, promoters inducible or repressible with lysine and promoters inducible or repressible with methionine, and in particular selected from the group consisting of:
pCTR1—copper inducible or repressible (SEQ ID No. 58),
pCTR3—copper inducible or repressible (SEQ ID No. 59),
pCUR1—copper inducible or repressible (SEQ ID No. 60),
pCUR2—copper inducible or repressible (SEQ ID No. 61),
pCUR3—copper inducible or repressible (SEQ ID No. 62),
pCUR4—copper inducible or repressible (SEQ ID No. 63),
pCUR5p—copper inducible or repressible (SEQ ID No. 64),
pCUR6—copper inducible or repressible (SEQ ID No. 65),
pCUR7—copper inducible or repressible (SEQ ID No. 66),
pCUR8—copper inducible or repressible (SEQ ID No. 67),
pCUR9—copper inducible or repressible (SEQ ID No. 68),
pCUR10—copper inducible or repressible (SEQ ID No. 69),
pCUR11—copper inducible or repressible (SEQ ID No. 70),
pCUR12—copper inducible or repressible (SEQ ID No. 71),
pCUR13—copper inducible or repressible (SEQ ID No. 72),
pCUR14—copper inducible or repressible (SEQ ID No. 73),
pCUR15—copper inducible or repressible (SEQ ID No. 74),
pCUR16—copper inducible or repressible (SEQ ID No. 75),
pCUR17—copper inducible or repressible (SEQ ID No. 76),
pLYS1—lysine inducible or repressible (SEQ ID No. 77),
pLYS4—lysine inducible or repressible (SEQ ID No. 78),
pLYS9—lysine inducible or repressible (SEQ ID No. 79),
pLYR1p—lysine inducible or repressible (SEQ ID No. 80),
pLYR2p—lysine inducible or repressible (SEQ ID No. 81),
pLYR3p—lysine inducible or repressible (SEQ ID No. 82),
pLYR4p—lysine inducible or repressible (SEQ ID No. 83),
pLYR5p—lysine inducible or repressible (SEQ ID No. 84),
pLYR6p—lysine inducible or repressible (SEQ ID No. 85),
pLYR7p—lysine inducible or repressible (SEQ ID No. 86),
pLYR8—lysine inducible or repressible (SEQ ID No. 87),
pLYR9—lysine inducible or repressible (SEQ ID No. 88),
pLYR10—lysine inducible or repressible (SEQ ID No. 89),
pLYR11—lysine inducible or repressible (SEQ ID No. 90),
pMET17—methionine inducible or repressible (SEQ ID No. 91),
pMET6—methionine inducible or repressible (SEQ ID No. 92),
pMET14—methionine inducible or repressible (SEQ ID No. 93),
pMET3—methionine inducible or repressible (SEQ ID No. 94),
pSAM1—methionine inducible or repressible (SEQ ID No. 95), pSAM2—methionine inducible or repressible (SEQ ID No. 96),
pMDH2—glucose inducible or repressible (SEQ ID No. 33),
pJEN1—glucose inducible or repressible (SEQ ID No. 116),
pICL1—glucose inducible or repressible (SEQ ID No. 117),
pADH2—glucose inducible or repressible (SEQ ID No. 118), and
pMLS1—glucose inducible or repressible (SEQ ID No. 119).

According to this embodiment, the inducible or repressible promoter according to the invention can, independently, be selected from the group consisting of pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

The activity of these promoters is thus repressed by the increasing presence of methionine, copper, lysine or glucose as indicated above, and their activity increases, i.e. is induced, when the quantity of methionine, copper, lysine or glucose is reduced.

In a particular embodiment, inducible or repressible promoters according to the invention may be selected from the group comprising promoters inducible or repressible with copper, promoters inducible or repressible with glucose, promoters inducible or repressible with lysine, promoters inducible or repressible with methionine and promoters inducible or repressible with threonine.

In a more particular embodiment, the inducible or repressible promoter according to the invention can, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, pCHA1, pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

More particularly, said promoters, identical or different, may be preferably characterized by a sequence of nucleic acid selected from the group consisting of sequences having at least 80% identity with sequences SEQ ID NO: 22 to 96 and 114 to 119.

Synthetic promoters as described in Blazeck & Alper (2013) Biotechnol. J. 8 46-58 can also be used.

The strong, weak and inductible or repressible promoters of the invention can originate from any organism from the Saccharomycetes class and can in particular originate, independently, from an organism selected from the group consisting of *Saccharomyces cerevisiae, Saccharomyces boulardii, Saccharomyces castelii, Saccharomyces bayanus, Saccharomyces arboricola, Saccharomyces kudriavzevii, Ashbya gossypii, Kluveromyces lactis, Pichia pastoris, Candida glabrata, Candida tropicalis, Debaryomyces castelii, Yarrowia lipolitica* and *Cyberlindnera jadinii*.

The strong, weak and inductible or repressible promoters of the invention can preferably originate from an organism selected from the group consisting of *Saccharomyces cerevisiae, Saccharomyces castelii, Saccharomyces bayanus, Saccharomyces arboricola, Saccharomyces kudriavzevii* and *Kluveromyces lactis*.

Terminators

As it is disclosed herein, the expression of the genes of interest that have been genetically engineered for obtaining a recombinant yeast according to the invention comprise appropriate transcription terminator sequences that are functional in yeast cells, including in *Saccharomyces cerevisiae*.

Said transcription terminators, identical or different, may be found in literature Yamanishi et al., (2013) ACS synthetic biology 2, 337-347.

Terminators more particularly interesting in the present invention may be selected from the group comprising:
tTDH2 from the gene coding for Glyceraldehyde-3-phosphate dehydrogenase, isozyme 2 (TDH2 gene=Sequence SEQ ID No. 97),
tCYC1 (=Sequence SEQ ID No. 98),
tTDH3 (=Sequence SEQ ID No. 99), and
tADH1 from gene coding for the alcohol dehydrogenase (ADH1 gene=Sequence SEQ ID No. 100),
tADH2 from gene coding for the alcohol dehydrogenase (ADH2 gene=Sequence SEQ ID No. 101),
tTPI1 from the gene encoding for the Triose Phosphate Isomerase (TPI1 gene=Sequence SEQ ID No. 102),
tMET17 from the gene encoding for the O-acetyl homoserine-O-acetyl serine sulfhydrylase (Met17 gene=Sequence SEQ ID No. 103),
tENO2 from the gene coding for Enolase II (ENO2 gene=Sequence SEQ ID No. 104),
tMET3 (=Sequence SEQ ID No. 105), and
tPGK1 from the gene encoding for the 3-phosphoglycerate kinase (PGK1 gene=Sequence SEQ ID No. 106),
tDIT1 (=Sequence SEQ ID No. 107),
tRPL3 (=Sequence SEQ ID No. 108),
tRPL41B (=Sequence SEQ ID No. 109),
tRPL15A (=Sequence SEQ ID No. 110),
tIDP1 (=Sequence SEQ ID No. 111).

More particularly, said terminator, identical or different, may be preferably characterized by a sequence of nucleic acid selected from the group consisting of sequences having at least 80% identity with sequences SEQ ID NO: 97 to 111.

Recombinant Yeast

Generally, yeast can grow rapidly and can be cultivated at higher density as compared with bacteria, and does not require an aseptic environment in the industrial setting. Furthermore, yeast cells can be more easily separated from the culture medium compared to bacterial cells, greatly simplifying the process for product extraction and purification.

Preferentially, the yeast of the invention may be selected among the genus *Saccharomyces, CandidaAshbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* or *Malassezia*.

More preferentially, the yeast may be Crabtree positive yeast of genus of *Saccharomyces, Dekkera, Schizosaccharomyces, Kluyveromyces, Torulaspora Zigosaccharomyces*, or. *Brettanomycces*

More preferentially, the yeast may be from the species *Saccharomyces cerevisiae, Saccharomyces boulardii, Saccharomyces douglasii, Saccharomyces bayanus* or.or *Zigosaccharomyces bailii, Schizosaccharomyces pombe, Dek-*

*kera brucelensis, Dekkera intermedia, Brettanomycces custersii, Brettanomycces intermedius, Kluyveromyces themotolerens, Torulaspora globosa, Torulaspora glabrata*

More preferentially, the recombinant yeast may belong to the *Saccharomyces* genus, and preferably to the *Saccharomyces cerevisiae* species.

Methods implemented to insert a specific DNA construct within a gene belong to the general knowledge of a man skilled in the art. A related method is described in more details in the herein after examples.

Culture Conditions

The present invention also relates to the use of a recombinant yeast such as above-defined, for the production of threonine.

The present invention further relates to a method for producing threonine, said method comprising the steps of:

(a) culturing a recombinant yeast as defined previously in a culture medium; and (b) recovering the threonine from said culture medium.

Typically, microorganisms (or yeasts) of the invention are grown at a temperature in the range of about 20° C. to about 37° C., preferably at a temperature ranging from 27 to 34° C., in an appropriate culture medium.

When the recombinant yeast according to the invention belongs to the *S. cerevisiae* species, the temperature may advantageously range from 27 to 34° C., in an appropriate culture medium.

Suitable growth media for yeast are common commercially prepared media such as broth that includes yeast nitrogen base, ammonium sulfate, and dextrose as the carbon/energy source) or YPD Medium, a blend of peptone, yeast extract, and dextrose in optimal proportions for growing most. Other defined or synthetic growth media may also be used and the appropriate medium for growth of the particular microorganism will be known by one skilled in the art of microbiology or fermentation science.

The terms "appropriate culture medium" are above-defined.

Examples of known culture media for a recombinant yeast according to the present invention are known to the person skilled in the art, and are presented in the following publication D. Burke et al., Methods in yeast Genetics—A cold spring harbor laboratory course Manual (2000).

Suitable pH ranges for the fermentation may be between pH 3.0 to pH 7.5, where pH 4.5 to pH 6.5 is preferred as the initial condition.

Fermentations may be performed under aerobic conditions or micro-aerobic conditions.

The amount of product in the fermentation medium can be determined using a number of methods known in the art, for example, high performance liquid chromatography (HPLC) or gas chromatography (GC).

The present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system may also be used in the present invention. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$.

Fermentations are common and well known in the art and examples may be found in Sunderland et al., (1992), herein incorporated by reference. Although the present invention is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production.

In order to still improve the threonine production, a particular embodiment may consist of culturing the recombinant yeast cells in an appropriate culture medium, such as above-mentioned, wherein the said culture medium comprises an optimal amount of carbon source, especially glucose.

Preferably, the cells are cultured in such an optimal culture medium during only a part of the whole culture duration. In some embodiments, the yeast cells are incubated in the said optimal culture medium 10 hours or more after initiation of the culture, which encompasses 11, 12, 13, 14, 15 or 16 hours or more after initiation of the culture.

Preferably, the cells are cultured in such an optimal culture medium during a time period ranging from 5 hours to 15 hours, which includes from 6 hours to 10 hours, e.g. 8 hours after initiation of the culture.

In preferred embodiments, the carbon source comprised in said optimal culture medium consists of glucose. In preferred embodiments, the said optimal culture medium comprises 12% w/w or more glucose, including 15% w/w or more glucose. In preferred embodiments, the said optimal culture medium comprises at most 40% w/w glucose, which includes at most 35% w/w glucose.

Thus, in the preferred embodiments described above, a method for producing threonine according to the invention may further comprise, between steps (a) and (c), an intermediate step (b) consisting of cultivating the yeast cells in the said optimal culture medium.

Purification of Threonine

According to a specific aspect of the invention, the fermentative production of threonine comprises a step of isolation of the threonine from the culture medium. Recovering the threonine from the culture medium is a routine task for a man skilled in the art. It may be achieved by a number of techniques well known in the art including but not limiting to distillation, gas-stripping, pervaporation, selective precipitation or liquid extraction. The expert in the field knows how to adapt parameters of each technique dependent on the characteristics of the material to be separated.

The yeast as model of microorganism in the present invention has been retained in that the synthesized threonine is entirely exported outside the cells, thus simplifying the purification process.

The synthesized threonine may be collected by distillation. Distillation may involve an optional component different from the culture medium in order to facilitate the isolation of threonine by forming azeotrope and notably with water. This optional component is an organic solvent such as cyclohexane, pentane, butanol, benzene, toluene, trichloroethylene, octane, diethylether or a mixture thereof.

Gas stripping is achieved with a stripping gas chosen among helium, argon, carbon dioxide, hydrogen, nitrogen or mixture thereof.

Liquid extraction is achieved with organic solvent as the hydrophobic phase such as pentane, hexane, heptane or dodecane.

EXAMPLES

Example 1: Protocol for Making a Recombinant Saccharomyces cerevisiae Strain According to the Invention All the hereinafter implemented recombinant *Saccharomyces cerevisiae* strains were constructed from standard strains using standard yeast molecular genetics procedure (Methods in yeast Genetics—A cold spring harbor laboratory course Manual (2000) by D. Burke, D. Dawson, T. Stearns CSHL Press).

Cluster of the following-mentioned genes were integrated in recombinant yeast at once using the ability of yeast to efficiently recombine free DNA ends which have sequence homology.

In addition, for a better comprehension of following genotypes:
- ade2, his3, leu2, trp1 and ura3 are auxotrophy marker genes.
- Lowercase letters mean that the considered gene is inactive, uppercase letters reflect an active gene.
- "::": following a gene name means that the gene is interrupted by what follows (if more than one gene are inserted, they are noted in brackets [ ]). The interruption of the gene is concomitant with an entire deletion of the coding sequence but preserves the promoter. In consequence the gene followed by "::" is inactive and is noted in lowercase. If not specified the transcription of the gene inserted is controlled by the promoter of the disrupted gene.
- "gene.Kl" means that the gene originates from *Kluyveromyces lactis*.

More particularly, the coding sequences to be cloned were artificially synthetized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotide sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit are then PCR amplified from the plasmids constructs, yielding X unit of linear DNA having overlapping sequences. At least one of this gene is an auxotrophic marker, in order to select for recombination event. All the linear fragments are transformed in the yeast at once, and recombinant yeast are selected for the auxotrophy related to the marker used. The integrity of the sequence is then verified by PCR and sequencing.

Example 2: Comparative Examples for the Production of Threonine

Two recombinant strains were obtained: YA2979-46B and YA2980-1B. These two strains have been recombined in order to only comprise a part of the modifications according to the invention.

Accordingly, these two strains are as follows: YA2979-46B: MAT-α, ade2, can1:: [pACU1-AAT2-tRPL3-pCUP1-1-PPC-5.Ec-tTPI1-can1]×4, his3:: [pACU5-HOM2-2-tRPL3-pTDH3-GDH.Eca-tIDP1-HIS3]×7, leu2, pyk1:: [LEU2.K1-pTEF3-AQR1-tRPL41B, pCUR3-PYK1-tPYK1], sam3:: [pCCW12-THR4-tRPL3-pTDH3-THR1-tIDP1-sam3]×2, trp1:: [pPDC1-PPC-5.Ec-tRPL3-pACU7-AK.Bs-tIDP1-TRP1]×4 YA2980-1B: MAT-α, ade2, can1:: [pACU1-AAT2-tRPL3-pCUP1-1-PPC-5.Ec-tTPI1-can1]×4, his3:: [pACU5-HOM2-2-tRPL3-pTDH3-GDH.Eca-tIDP1-HIS3]×7, leu2, pyk1:: [LEU2.K1-pCUR3-PYK1-tPYK1], sam3:: [pCCW12-THR4-tRPL3-pTDH3-THR1-tIDP1-sam3]×2, trp1:: [pPDC1-PPC-5.Ec-tRPL3-pACU7-AK.Bs-tIDP1-TRP1]×4

PPC-5 is a more stable form of PPC wherein an alanine has been added in N+1 (position 2 of the amino acid sequence).

All these strains were grown for 24 hours in YE (Yeast Extract) 2%, Glucose 8%, $(NH_4)_2SO_4$ 50 mM, and $CH_3SNa$ 1 g/L. 500 μM of $CuSO_4$ was added after 8 hours. The content of threonine in the medium was assayed after 26 hours using the AccQ-Tag precolumn derivatization method for amino acid determination using a AccQ-Tag Ultra Derivatization Kit from Waters as advised by the manufacturer.

The threonine amount obtained with these two strains was 2 g/L$^{-1}$. In comparison, a non modified strain is not able to produce a detectable quantity of threonine.

It results from these experiments that a recombinant strain comprising the modifications according to the invention produces a greater amount of threonine when cultured in the same conditions as a native strain.

The invention claimed is:

1. A threonine-producing recombinant yeast, in the genome of which:
  (A) at least one nucleic acid encoding an aspartate semi-aldehyde dehydrogenase that can use as coenzyme both NAD and NADP is overexpressed and/or is under the control of an inducible or repressible promoter;
  (B) at least one nucleic acid encoding an homoserine kinase is overexpressed and/or is under the control of an inducible or repressible promoter,
  (C) at least one nucleic acid encoding a threonine synthase is overexpressed and/or is under the control of an inducible or repressible promoter;
  (D) at least one nucleic acid encoding an aspartate kinase is overexpressed and/or is under the control of an inducible or repressible promoter; and
  (E) at least one nucleic acid encoding a glutamate dehydrogenase that converts oxo-glutarate to glutamate is overexpressed and/or is under the control of an inducible or repressible promoter,
wherein:
  the yeast is of the genus *Saccharomyces* or *Kluyveromyces*, and
  the at least one nucleic acid encoding the aspartate semi-aldehyde dehydrogenase that can use as coenzyme both NAD and NADP is a nucleic acid sequence having at least 27% sequence identity with the nucleic acid sequence of SEQ ID NO:1.

2. The recombinant yeast according to claim 1, in the genome of which at least one nucleic acid encoding an aspartate transaminase is overexpressed and/or is under the control of an inducible or repressible promoter.

3. The recombinant yeast according to claim 1, in the genome of which at least one nucleic acid encoding an homoserine dehydrogenase is overexpressed.

4. The recombinant yeast according to claim 1, in the genome of which:
   a) at least one endogenous nucleic acid encoding an homoserine-O-acetyltransferase has been deleted, and/or
   b) at least one nucleic acid encoding an homoserine-O-acetyltransferase is under the control of an inducible or repressible promoter and/or is in a destabilized form.

5. The recombinant yeast according to claim 1, in the genome of which:
   a) at least one endogenous nucleic acid encoding a methionine synthase has been deleted, and/or
   b) at least one nucleic acid encoding a methionine synthase is under the control of an inducible or repressible promoter and/or is in a destabilized form.

6. The recombinant yeast according to claim 1, in the genome of which at least one nucleic acid encoding a probable transporter is overexpressed.

7. The recombinant yeast according to claim 1, in the genome of which at least one of the following modifications has been performed:
   (A) at least one endogenous nucleic acid encoding a general amino acid permease GAP1 has been deleted from the genome of the yeast, and, optionally:
      (i) at least one nucleic acid encoding a general amino acid permease GAP1 has been inserted and is under the control of an inducible or repressible promoter, and/or
      (ii) at least one nucleic acid encoding a destabilized general amino acid permease GAP1 has been inserted;
   (B) at least one endogenous nucleic acid encoding a high-affinity glutamine permease GNP1 has been deleted from the genome of the yeast, and, optionally:
      (i) at least one nucleic acid encoding a high-affinity glutamine permease GNP1 has been inserted and is under the control of an inducible or repressible promoter, and/or
      (ii) at least one nucleic acid encoding a destabilized high-affinity glutamine permease GNP1 has been inserted;
   (C) at least one endogenous nucleic acid encoding a general amino acid permease AGP1 has been deleted from the genome of the yeast, and, optionally:
      (i) at least one nucleic acid encoding a general amino acid permease AGP1 has been inserted and is under the control of an inducible or repressible promoter, and/or
      (ii) at least one nucleic acid encoding a destabilized general amino acid permease AGP1 has been inserted.

8. The recombinant yeast according to claim 7, in the genome of which at least two of the modifications have been performed.

9. The recombinant yeast according to claim 1, wherein the nucleic acid encoding an aspartokinase, a high-affinity glutamine permease, a general amino acid permease, an homoserine-O-acetyltransferase and a methionine synthase are, independently, nucleic acid from a yeast.

10. The recombinant yeast according to claim 1, wherein the inducible or repressible promoter is, independently, selected from the group consisting of promoters inducible or repressible with copper, promoters inducible or repressible with methionine and promoters inducible or repressible with threonine.

11. The recombinant yeast according to claim 1, wherein the inducible or repressible promoter is, independently, selected from the group consisting of promoters inducible or repressible with copper, promoters inducible or repressible with lysine and promoters inducible or repressible with methionine.

12. A method for producing threonine, comprising:
   (a) culturing the recombinant yeast according to claim 1 in a culture medium to produce threonine; and
   (b) recovering the threonine from the culture medium.

13. The method according to claim 12, wherein the culture medium comprises at least a carbon source.

14. A method comprising producing threonine with the recombinant yeast according to claim 1.

15. The recombinant yeast according to claim 1, wherein the at least one nucleic acid encoding the homoserine kinase encodes an homoserine kinase THR1.

16. The recombinant yeast according to claim 1, wherein the at least one nucleic acid encoding the threonine synthase encodes a threonine synthase THR4.

17. The recombinant yeast according to claim 1, wherein the at least one nucleic acid encoding the aspartokinase and/or the at least one nucleic acid encoding the aspartate kinase encode:
   an aspartokinase HOM3; and/or
   an aspartate kinase AK.

18. The recombinant yeast according to claim 1, wherein the nucleic acids respectively encode at least the combination of:
   (A) an aspartate semi-aldehyde dehydrogenase HOM2-2 encoded by the nucleic acid sequence of SEQ ID NO:2;
   (B) an homoserine kinase THR1;
   (C) a threonine synthase THR4; and
   (D) an aspartate kinase AK.

19. The recombinant yeast according to claim 1, wherein the yeast is of the species *Saccharomyces cerevisiae, Saccharomyces boulardii, Saccharomyces douglasii, Saccharomyces bayanus* or *Kluveromyces themotolerens*.

20. The recombinant yeast according to claim 1, wherein the at least one nucleic acid encoding the aspartate semi-aldehyde dehydrogenase that can use as coenzyme both NAD and NADP is the nucleic acid of SEQ ID NO: 2.

21. The recombinant yeast according to claim 1, wherein the at least one nucleic acid encoding the aspartate semi-aldehyde dehydrogenase that can use as coenzyme both NAD and NADP is a nucleic acid sequence having at least 65% sequence identity with the nucleic acid sequence of SEQ ID NO:1.

22. The recombinant yeast according to claim 1, wherein the at least one nucleic acid encoding the aspartate semi-aldehyde dehydrogenase that can use as coenzyme both NAD and NADP is a nucleic acid sequence having at least 80% sequence identity with the nucleic acid sequence of SEQ ID NO: 1.

* * * * *